US006887844B1

(12) United States Patent
Ronn et al.

(10) Patent No.: US 6,887,844 B1
(45) Date of Patent: May 3, 2005

(54) NCAM BINDING COMPOUNDS

(76) Inventors: Lars Christian Ronn, Rektorparken 14, 3.th, DK-2450 Copenhagen SV (DK); Arne Holm, Skodsborgparken 20, 2.th, DK-2942 Skodsborg (DK); Marianne Olsen, Mosevej 5, DK-4000 Roskilde (DK); Soren Ostergaard, Borrebyvej 21, DK-2700 Bronshoj (DK); Peter H. Jensen, Ahlefeldsgade 18A, 1.th., DK-1359 Copenhagen K (DK); Flemming M. Poulsen, C.F. Richsvej 99A, 1. tv., DK-2000 Frederiksberg (DK); Vladislav Soroka, Tuborovej 58, 1.tv., DK-2900 Hellerup (DK); Igor Ralets, Norre Alle 8, 111, DK-2200 Copenhagen N (DK); Vladimir Berezin, Norrebrogade 223, 1.th., DK-2200 Copenhagen N (DK); Elisabeth Bock, Tonysvej 20, DK-2920 Charlottenlund (DK)

( * ) Notice: Subject to any disclaimer, the term of this patent is extended or adjusted under 35 U.S.C. 154(b) by 0 days.

(21) Appl. No.: 09/787,443

(22) PCT Filed: Sep. 23, 1999

(86) PCT No.: PCT/DK99/00500

§ 371 (c)(1),
(2), (4) Date: Jul. 30, 2001

(87) PCT Pub. No.: WO00/18801

PCT Pub. Date: Apr. 6, 2000

(30) Foreign Application Priority Data

Sep. 29, 1998 (DK) .......................................... 1998 01232
Apr. 29, 1999 (DK) .......................................... 1999 00592

(51) Int. Cl.[7] .......................... A61K 38/00; A61K 38/04; C07K 7/00

(52) U.S. Cl. ............................ 514/2; 514/15; 530/300; 530/327

(58) Field of Search ............................ 514/2, 15, 4, 8, 514/14; 530/300, 327, 328, 329, 330

(56) References Cited

PUBLICATIONS

Doherty et al. (Mar. 1995) "The Neural Cell Adhesion Molecule and Synaptic Plasticity." J. Neurobiol. 26(3):437–446.*
Wells, 1990, Biochemistry 29:8509–8517.*
Ngo et al.. 1994, The Protein Folding Problem and Tertiary Structure Prediction. pp. 492–495.*
Bork. 2000, Genome Research 10:398–400.*
Skolnick et al., 2000, Trends in Biotech. 18(1): 34–39.*
Doerks et al., 1998, Trends in Genetics 14:248–250.*
Smith et al., 1997, Nature Biotechnology 15:1222–1223.*
Brenner, 1999, Trends in Genetics 15:123–133.*
Bork et al., 1996, Trends in Genetics 12:425–427.*

Andersson et al.; "Age–related changes in expression of the neural cell adhesion molecule in skeletal muscle: a comparative study of newborn, adult and aged rats"; Biochemical Journal 1993; 290: 641–648.
Beggs et al.; "NCAM140 Interacts with the Focal Adhesion Kinase p125$^{fak}$ and the SRC–related Tyrosine Kinase p59$^{fyn}$"; Journal of Biological Chemistry 1997; 272, No. 13: 8310–8319.
Carenini et al.; "Absence of the myelin–associated glycoprotein (MAG) and the neural cell adhesion molecule (N–CAM) interferes with the maintenance, but not with the formation of peripheral myelin"; Cell and Tissue Research 1997; 287: 3–9.
Cremer et al.; "NCAM Is Essential for Axonal Growth and Fasciculation in the Hippocampus"; Molecular & Cellular Neurosciences 1997; 8: 323–335.
Cremer et al.; "Inactivation of the N–CAM gene in mice results in size reduction of the olfactory bulb and deficits in spatial learning"; Nature 1994; 367: 455–459.
Daniloff et al.; "Altered Expression of Neuronal Cell Adhesion Molecules Induced by Nerve Injury and Repair"; Journal of Cell Biology 1986; 103: 929–945.
Daston et al.; "Spatially Restricted Increase in Polysialic Acid Enhances Corticospinal Axon Branching Related To Target Recognition and Innervation"; Journal of Neuroscience 1996; 16: 5488–5497.
Doherty et al.; "The vase exon downregulates the neurite growth–promoting activity of NCAM 140"; Nature 1992; 356: 791–793.
Doherty et al.; "Review CAM–FGF Receptor Interactions: A Model for Axonal Growth"; Molecular and Cellular Neuroscience 1996; 8: 99–111.
Doyle et al.; "Hippocampal NCAM180 Transiently Increases Sialylation During the Acquisition and Consolidation of a Passive Avoidance Response in the Adult Rat"; Journal of Neuroscience Research 1992; 31: 513–523.
Edelman et al.; "Place–dependent Cell Adhesion, Process Retraction, and Spatial Signaling in Neural Morphogenesis"; Cold Spring Harbor Symposia on Quantitative Biology, Cold Spring Harbor Laboratory Press, 1990: 303–318.
Fazeli et al.; "The role of cell adhesion molecules during the development and regeneration of the neuromuscular system"; Seminars in the Neurosciences 1996; 8: 367–377.
Fields et al.; "Neural cell Adhesion molecules in activity–dependent development and synaptic plasticity"; Trends in Neurosciences 1996; 19: 473–480.

(Continued)

Primary Examiner—Gary Kunz
Assistant Examiner—Christopher James Nichols
(74) Attorney, Agent, or Firm—Iver P. Cooer

(57) ABSTRACT

The invention provides novel compounds which are capable to stimulate the proliferation or/and the outgrowth from cells presenting the neural cell adhesion molecule (NCAM). Additionally, the invention relates to pharmaceutical compositions, medicaments and methods for treatment of normal, degenerated and damaged NCAM presenting cells.

21 Claims, 27 Drawing Sheets

OTHER PUBLICATIONS

Frei et al.; "Different Extracellular Domains of the Neural Cell Adhesion Molecule (N–CAM) Are Involved in Different Functions"; Journal of Cell Biology 1992; 118: 177–194.

Furka et al.; "General method for rapid synthesis of multicomponent peptide mixtures"; International Journal of Peptide and Protein Research 1991; 37: 487–493.

Gaardsvoll et al.; "Age–related changes in expression of neural cell adhesion molecule (NCAM) in heart: a comparative study of newborn, adult and aged rats"; European Journal of Cell Biology 1993; 61: 100–107.

Horstkorte et al.; "The Fourth Immuneoglobulin–like Domain of NCAM Contains a Carbohydrate Recognition Domain for Oligomannosidic Glycans Implicated in Association with L1 and Neurite Outgrowth"; The Journal of Cell Biology 1993; vol. 121, No. 6, 1409–1421.

Jucker et al.; "Transient upregulation of NCAM mRNA in astrocytes in response to entorhinal cortex lesions and ischemia"; Brain Research 1995; Molecular Brain Rese.: 149–156.

Kasper et al.; "Functional Characterization of NCAM Fibronectin Type III Domains: Demonstration of Modulatory Effects of the Proline–Rich Sequence Encoded by Alternatively Spliced Exons a and AAG"; Journal of Neuroscience Research 1996; 46: 173–186.

Kiselyov et al.; "The First Immunoglobulin–like Neural Cell Adhesion Molecule (NCAM) Domain Is Involved in Double–reciprocal Interaction with the Second Immunoglobulin–like NCAM Domain and in Heparin Binding"; Journal of Biological Chemistry 1997; 272: 10125–10134.

Knittel et al.; "Cell–Type–Specific Expression of Neural Cell Adhesion Molecule (N–CAM) in Ito Cells of Rat Liver, Up–Regulation during in Vitro Activation and in Hepatic Tissue Repair"; American Journal of Pathology 1996; 149: 449–462.

Krushel et al.; "Neural cell adhesion molecule (N–CAM) domains and intracellular signaling pathways involved in the inhibition of astrocyte proliferation"; Proceedings of the National Academy Of Science of the United States of America 1998; 95: 2592–2596.

Lackie et al.; "Polysialic acid and N–CAM localisation in embryonic rat kidney: mesenchymal and epithelial elements show different patterns of expression"; Development 1990; 110: 933–947.

Lahrtz et al.; "Vase–Encoded Peptide Modifies NCAM–and L1–Mediated Neurite Outgrowth"; Journal of Neuroscience Research 1997; 50: 62–68.

Lam et al.; "A new type of synthetic peptide library for identifying ligand–binding activity"; Nature 1991; 354:82–84.

Lam et al.; "Streptavidin and Avidin Recognize Peptide Ligands with Different Motifs"; Immunomethods 1992; 1: 11–15.

Landsmesser et al.; "Polysialic Acid As a Regulator of Intramuscular Nerve Branching during Embryonic Development"; Neutrone 1990; 4–655–667.

Lüthl et al.; "Hippocampal long–term potentiation and neural cell adhesion molecules L1 and NCAM"; Nature 1994; 372:777–779.

Maar et al.; "Characterization of Microwell Cultures of Dissociated Brain Tissue for Studies of Cell–Cell Interactions"; Journal of Neuroscience Research 1997; 47: 163–172.

Massaro et al.; "N–CAM in cerebrospinal fluid: a marker of synaptic remodelling after acute phases of multiple sclerosis?"; Italian Jorunal of Neurological Sciences 1987; Suppl. 6:85–88.

Møller et al.; "NCAM in developing mouse gonads and ducts"; Anatomy and Embryology 1991; 184: 541–548.

Møller et al.; "Differential Expression of Neural Cell Adhesion Molecule and Cadherins in Pancreatic Islets, Glucagonomas, and Insulinomas"; Molecular Endocrinology 1992; 6: 1332–1342.

Nieke et al.; "Expression of the neural cell adhesion molecules L1 and N–CAM and their common carbohydrate epitope L2/HNK–1 during development and after transection of the mouse sciatic nerve"; Differentation 1985; 30: 141–151.

Olsen et al.; "The Ability to Re–Express Polysialylated NCAM In Soleus Muscle After Denervation is Reduced In Aged Rats Compared To Young Adult Rats"; Int J Devl Neuroscience 1995; 13: 97–104.

Ono et al.; "N–CAM Mutation Inhibits Tangential Neuronal Migration and Is Phenocopied by Enzymatic Removal of Polysialic Acid"; Neurone 1994; 13: 595–609.

Pollerberg et al.; "A Functional Role for the Middle Extracellular Region of the Neural Cell Adhesion Molecule (NCAM) in Axonal Fasciculation and Orientation"; Developmental Biology 1993; 156(2): 324–340.

Rabinowitz et al.; "Targeted mutation of Ncam to produce a secreted molecule results in a dominant embryonic lethality"; Proceedings of the National Academy of Science of the United States of America 1996; 93: 6421–6424.

Ranheim et al.; "Homophilic adhesion mediated by the neural cell adhesion molecule involves multiple immunoglobulin domains"; Proceedings of the National Academy of Science of the United States of America 1996; 93: 4071–4075.

Rao et al.; "Identification of a peptide Sequence Involved in Homophilic Binding in the Neural Cell Adhesion Molecule NCAM"; Journal of Cell Biology 1992; 118: 937–949.

Rao et al.; "Mechanism of Homophilic Binding Mediated by the Neural Cell Adhesion Molecule NCAM"; Journal of Biological Chemistry 1994; 269: 27540–27548.

Romanska et al.; "Neural Cell Adhesion Molecule (NCAM) Expression in Nerves and Muscle of Developing Human Large Bowel"; Journal of Pediatric Gastroenterology and Nutrition 1996; 22: 351–358.

Rønn et al.; "NCAM–antibodies modulate induction of long–term potentiation in rat hippocampal CA1"; Brain Research 1995; 677: 145–151.

Rønn; Ph.D. Thesis; The Protein Laboratory and The Division of Neurophysiology, University of Copenhagen 1997.

Rutishauser et al.; "Polysialic acid in the vertebrate nervous system: a promoter of plasticity in cell–cell interactions"; Trends in Neurosciences 1996; 19: 422–427.

Sandig et al.; "The Homophilic Binding Site of the Neural Cell Adhesion Molecule NCAM Is Directly Involved in Promoting Neurite Outgrowth from Cultured Neural Retinal Cells"; Journal of Biological Chemistry 1994; 269: 14841–14848.

Sanes et al.; "Expression of Several Adhesive Macromolecules (N–CAM, L1, J1, NILE, Uvomorulin, Laminin, Fibronectin, and a Heparan Sulfate Proteoglycan) In Embryonic, Adult and Denervated Adult Skeletal Muscle"; Journal of Cell Biology 1986; 102:420–431.

Schmid et al.; "NCAM Stimulates the Ras–MAPK Pathway and CREB Phosphorylation in Neuronal Cells"; Journal of Neurobiology 1999; 38: 542–558.

Scholey et al.; "A Role for the Neural Cell Adhesion Molecule in a Late, Consolidating Phase of Glycoprotein Synthesis Six Hours Following Passive Avoidance Training of the Young Chick"; Neuroscience 1993; 55: 499–509.

Schuch et al.; "Neural Cell Adhesion Molecules Influence Second Messenger Systems"; Neurone 1989; 3: 13–20.

Shen et al.; "Role of Neural Cell Adhesion Molecule and Polysialic Acid in Mouse Circadian Function"; Journal of Neuroscience 1997; 17: 5221–5229.

Stahlhut et al.; "NCAM–Fibronectin–Type–III–Domain Substrata With and Without a Six–Amino–Acid–Long Proline–Rich Insert Increase the Dendritic and Axonal Arborization of Spinal Motoneurons"; Journal of Neuroscience Research 1997; 48: 112–121.

Stork et al.; "Increased Intermale Aggression and Neuroendocrine Response in Mice Deficient for the Neural Cell Adhesion Molecule (NCAM)"; European Journal of Neuroscience 1997; 9: 1117–1125.

Thomsen; "The three–dimensional structure of the first domain of neural cell adhesion molecule"; Nature Structural Biology 1996; 3: 581–585.

van Kammen et al.; "Further Studies of Elevated Cerebrospinal Fluid Neuronal Cell Adhesion Molecule in Schizophrenia"; Biological Psychiatry 1998; 43: 680–686.

Walsh et al.; "Expression of Cell Adhesion Molecule, N–CAM, in Diseases of Adult Human Skeletal Muscle"; Neuroscience Letters 1985; 59: 73–78.

Zhang et al.; "Polysialic Acid is Required for Optimal Growth of Axons on a Neuronal Substrate"; Journal of Neuroscience 1992; 12: 3107–3114.

Rønn et al.; A simple procedure for quantification of neurite outgrowth based on sterological principles; Journal of Neuroscience Methods; 2000; 20(6); 25–32.

Rønn et al.; Neurite Outgrowth Induced by a Synthetic Peptide Ligand of Neural Cell Adhesion Molecule Requires Fibroblast Growth Factor Receptor Activation; Journal of Neurochemistry; 2000, 75; 665–671.

Kolkova et al.; Neural Cell Adhesion Molecule–Stimulated Neurite Outgrowth Depends on Activation of Protein Kinase C and the Ras–Mitoger–Activated Protein Kinase Pathway; The Journal of Neuroscience, 2000; 20(6); pp. 2238–2246.

Foley et al.; A Synthetic Peptide Ligand of Neural Cell Adhesion Molecule (NCAM) IgI Domain prevents NCAM Internalization and Disrupts Passive Avoidance Learning; Journal of Neurochemistry; 2000; 74(6); pp. 2607–2613.

Rønn et al.; Increased intracellular calcium is required for neurite outgrowth induced by a synthetic peptide ligand of NCAM; FEBS Letters 518 (2002) 60–66.

* cited by examiner

Fig. 2
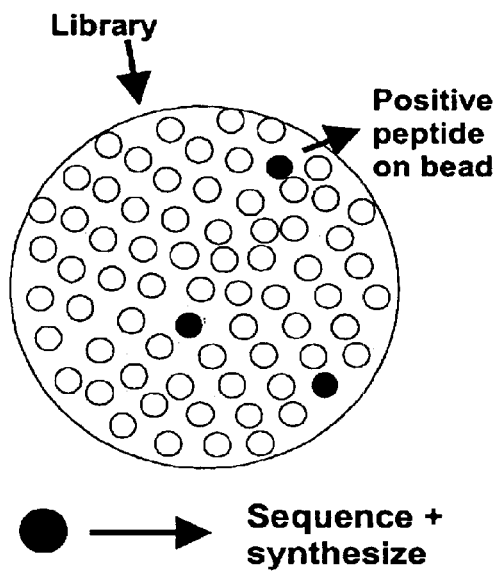
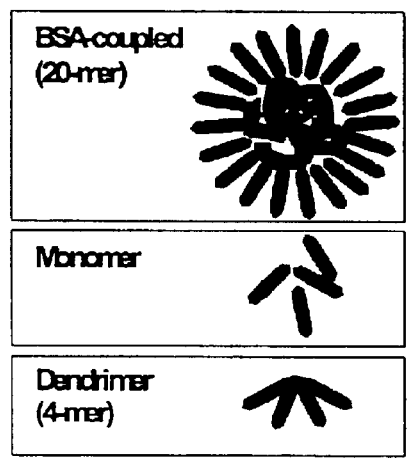
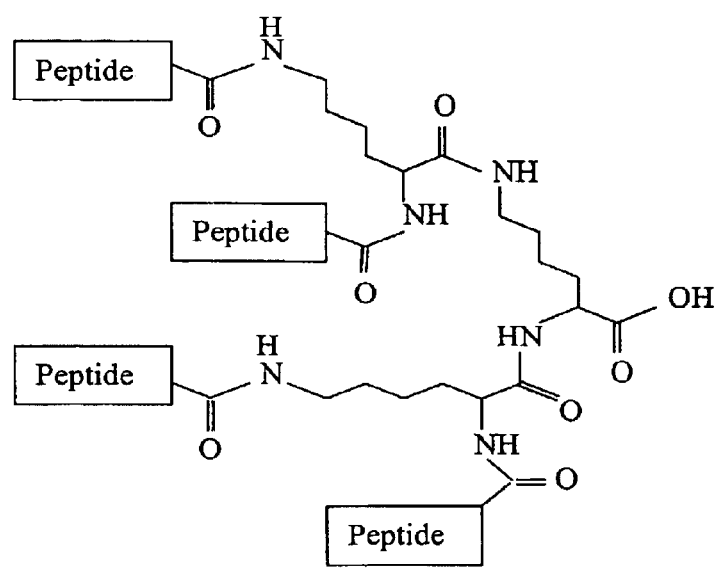

Fig. 3
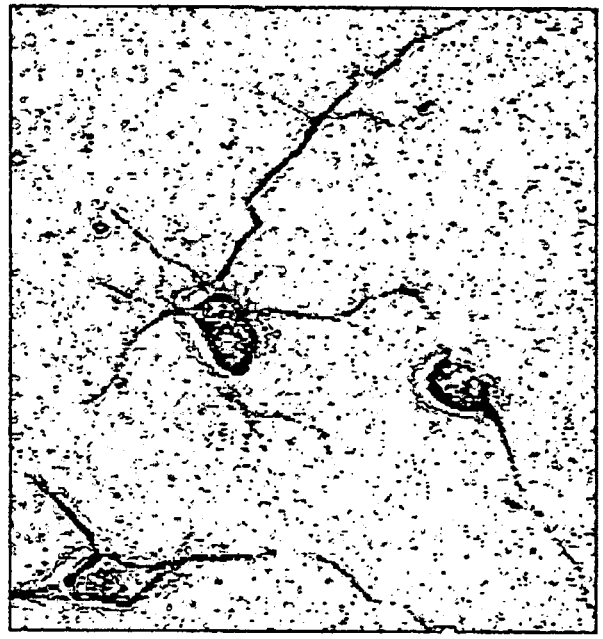
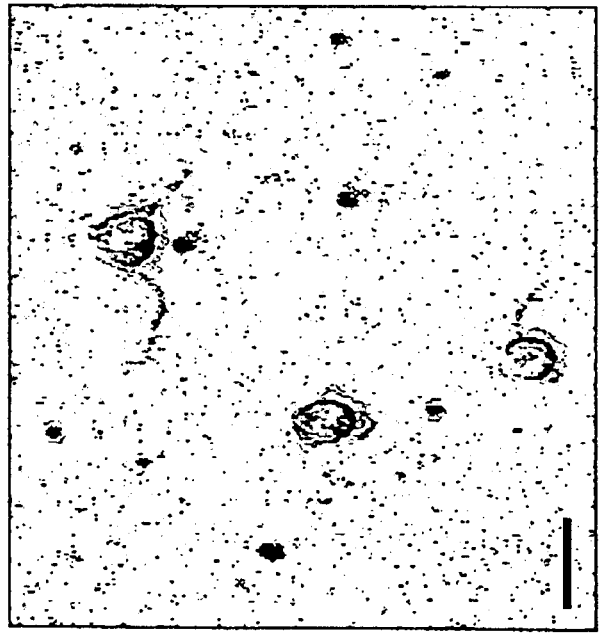

Fig. 4

| | | | SEQ ID NO.: |
|---|---|---|---|
| A | | A R A L N W G A K P K | 3 |
| | | A G S A V K L K K K A | 4 |
| | | A K Y V L I P I R I S | 5 |
| | | A S T K R S M Q G I | 6 |
| | | A R R A I L M$^{QTN}$ A L | 7 |
| | | A Y Y L I V R V N R I | 8 |
| | | A T N K K T G R R P R | 9 |
| | | A K R N G P L I N R I | 10 |
| | | A K R S V Q K L D G Q | 11 |
| | | A R Q K T M K P R R S | 12 |
| | | A G D Y N P D L D R | 13 |
| | | A S K K P K R N I K A | 1 |
| | | A R K T R E R K S K D | 14 |
| | | A S Q A K R R K G P R | 15 |
| | | A P K L D R M L T K K | 16 |
| | | A K K E K P N K P N D | 17 |
| | | A Q M G R Q S I D R N | 18 |
| | | A E G G K K K K M R A | 19 |
| | | A K K E R Q R K D T Q | 2 |
| | | A K K K E Q K Q R N A | 20 |
| | | A K S R K G N S S L M | 21 |
| | | A R K S R D M T A I K | 22 |
| B | C3 | A S K K P K R N I K A | 1 |
| | | A K R N G P L I N R I | 39 |
| | | A K R S V Q K L D G Q | 40 |
| | | A S T K R S M Q G I | 41 |
| | | A T N K K T G R R P R | 42 |
| | | A R A L N W G A K P K | 43 |
| | | A R Q K T M K P R R S | 44 |
| C | D3 | A K K E R Q R K D T Q | 2 |
| | | A K K E K P N K P N D | 45 |
| | | A R K T K S R E R K D | 46 |
| D | D4 | A R A L N W G A K P K | 3 |
| | | A T N K K T G R R P R | 47 |

Fig. 7

| NO.: | Peptide | | | | Sequence | | | | | | | | Effect* Neur | Agg |
|------|---------|---|---|---|---|---|---|---|---|---|---|---|------|-----|
| 1 | C3 | A | S | K | K | P | K | R | N | H | I | K | A | ++ | – |
| 2 | C3dacetyl.K(120) | A | S | K# | K# | P | K# | R | N | | I | K# | A | + | – |
| 3 | Ala subst K/R 116 | A | S | K | K | P | K | A | N | H | I | K | A | ++ | – |
| 4 | 117 | A | S | K | K | P | A | A | N | H | I | K | A | 0 | 0 |
| 5 | 118 | A | S | K | A | P | A | A | N | H | I | K | A | 0 | 0 |
| 6 | 119 | A | A | K | A | P | A | A | N | H | I | K | A | 0 | 0 |
| 7 | P→A 122 | A | S | K | K | A | K | R | N | I | I | K | A | ++ | – |
| 8 | Scrambled C3 120 | A | K | K | K | A | K | R | I | S | A | N | P | ++ | – |
| 9 | 114 | P | N | A | S | P | R | I | S | K | K | K | A | ++ | – |
| 10 | C3scr | K | N | K | P | A | Q | K | K | I | K | A | K | ++ | – |
| 11 | D3 | A | K | K | E | R | R | A | Q | D | K | A | Q | ++ | – |
| 12 | scrambled D3 | R | T | Q | D | K | A | K | E | R | R | K | T | + | – |
| 13 | D4 | A | R | A | L | N | W | A | P | R | P | A | | + | – |
| 14 | scrambled D4 | G | L | K | R | W | A | P | K | R | A | | | | – |
| 15 | K6 (dendrimer 115) | K | K | K | K | K | K | | | | | | | | – |

* effect on neurite extension (neur) and aggregation (agg)
acetylation on lysine 1. – SEQ ID NO.: 1
2. – SEQ ID NO.: 27
3. – SEQ ID NO.: 28
4. – SEQ ID NO.: 29
5. – SEQ ID NO.: 30
6. – SEQ ID NO.: 31
7. – SEQ ID NO.: 32
8. – SEQ ID NO.: 33
9. – SEQ ID NO.: 34
10. – SEQ ID NO.: 35
11. – SEQ ID NO.: 2
12. – SEQ ID NO.: 36
13. – SEQ ID NO.: 3
14. – SEQ ID NO.: 37
15. – SEQ ID NO.: 38

FIG. 17

```
  1 MLQTKDLIWT LFFLGTAVSL QVDIVPSQGE ISVGESKFFL CQVAGDAKDK DISWFSPNGE
 61 KLTPNQQRIS VVWNDDSSST LTIYNANIDD AGIYKCVVTG EDGSESEATV NVKIFQKLMF
121 KNAPTPQEFR EGEDAVIVCD VVSSLPPTII WKHKGRDVIL KKDVRFIVLS NNYLQIRGIK
181 KTDEGTYRCE GRILARGEIN FKDIQVIVNV PPTIQARQNI VNATANLGQS VTLVCDAEGF
241 PEPTMSWTKD GEQIEQEEDD EKYIFSDDSS QLTIKKVDKN DEAEYICIAE NKAGEQDATI
301 HLKVFAKPKI TYVENQTAME LEEQVTLTCE ASGDPIPSIT WRTSTRNISS EEKTLDGHMV
361 VRSHARVSSL TLKSIQYTDA GEYICTASNT IGQDSQSMYL EVQYAPKLQG PVAVYTWEGN
421 QVNITCEVFA YPSATISWFR DGQLLPSSNY SNIKIYNTPS ASYLEVTPDS ENDFGNYNCT
481 AVNRIGQESL EFILVQADTP SSPSIDQVEP YSSTAQVQFD EPEATGGVPI LKYKAEWRAV
541 GEEVWHSKWY DAKEASMEGI VTIVGLKPET TYAVRLAALN GKGLGEISAA SEFKTQPVQG
601 EPSAPKLEGQ MGEDGNSIKV NLIKQDDGGS PIRHYLVRYR ALSSEWKPEI RLPSGSDHVM
661 LKSLDWNAEY EVYVVAENQQ GKSKAAHFVF RTSAQPTAIP ANGSPTSGLS TGAIVGILIV
721 IFVLLLVVVD ITCYFLNKCG LFMCIAVNLC GKAGPGAKGK DMEEGKAAFS KDESKEPIVE
781 VRTEEERTPN HDGGKHTEPN ETTPLTEPEK GPVEAKPECQ ETETKPAPAE VKTVPNDATQ
841 TKENESKA
```

Fig. 19
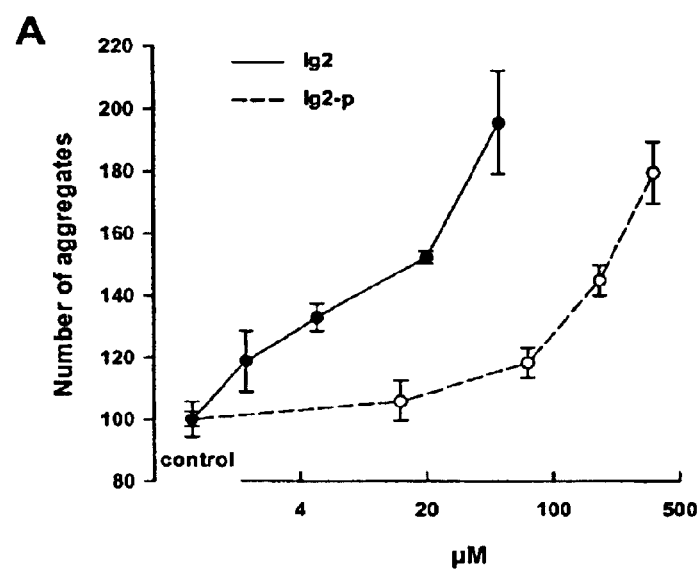
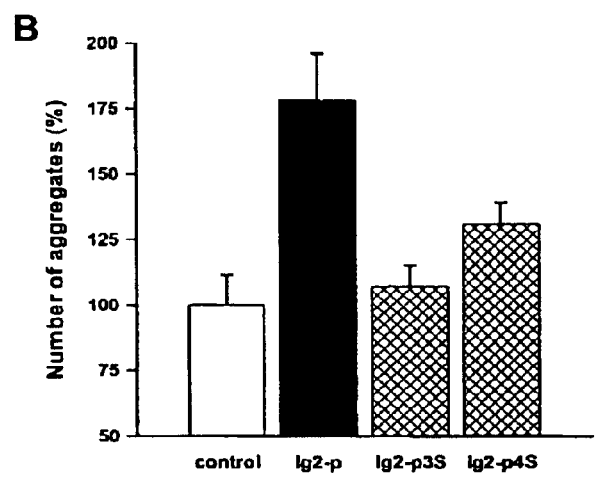

SEQUENCE LISTING

<160> NUMBER OF SEQ ID NOS: 50

<210> SEQ ID NO 1
<211> LENGTH: 11

```
<212> TYPE: PRT
<213> ORGANISM: Artificial sequence
<220> FEATURE:
<223> OTHER INFORMATION: peptide fragment

<400> SEQUENCE: 1

Ala Ser Lys Lys Pro Lys Arg Asn Ile Lys Ala
1               5                   10

<210> SEQ ID NO 2
<211> LENGTH: 11
<212> TYPE: PRT
<213> ORGANISM: Artificial sequence
<220> FEATURE:
<223> OTHER INFORMATION: peptide fragment

<400> SEQUENCE: 2

Ala Lys Lys Glu Arg Gln Arg Lys Asp Thr Gln
1               5                   10

<210> SEQ ID NO 3
<211> LENGTH: 11
<212> TYPE: PRT
<213> ORGANISM: Artificial sequence
<220> FEATURE:
<223> OTHER INFORMATION: peptide fragment

<400> SEQUENCE: 3

Ala Arg Ala Leu Asn Trp Gly Ala Lys Pro Lys
1               5                   10

<210> SEQ ID NO 4
<211> LENGTH: 11
<212> TYPE: PRT
<213> ORGANISM: Artificial sequence
<220> FEATURE:
<223> OTHER INFORMATION: peptide fragment

<400> SEQUENCE: 4

Ala Gly Ser Ala Val Lys Leu Lys Lys Lys Ala
1               5                   10

<210> SEQ ID NO 5
<211> LENGTH: 11
<212> TYPE: PRT
<213> ORGANISM: Artificial sequence
<220> FEATURE:
<223> OTHER INFORMATION: peptide fragment

<400> SEQUENCE: 5

Ala Lys Tyr Val Leu Ile Pro Ile Arg Ile Ser
1               5                   10

<210> SEQ ID NO 6
<211> LENGTH: 10
<212> TYPE: PRT
<213> ORGANISM: Artificial sequence
<220> FEATURE:
<223> OTHER INFORMATION: peptide fragment

<400> SEQUENCE: 6

Ala Ser Thr Lys Arg Ser Met Gln Gly Ile
1               5                   10

<210> SEQ ID NO 7
<211> LENGTH: 10
<212> TYPE: PRT
```

```
<213> ORGANISM: Artificial sequence
<220> FEATURE:
<223> OTHER INFORMATION: peptide fragment
<220> FEATURE:
<221> NAME/KEY: MISC_FEATURE
<222> LOCATION: (8)..(8)
<223> OTHER INFORMATION: Q, T or N

<400> SEQUENCE: 7

Ala Arg Arg Ala Ile Leu Met Xaa Ala Leu
1               5                   10

<210> SEQ ID NO 8
<211> LENGTH: 11
<212> TYPE: PRT
<213> ORGANISM: Artificial sequence
<220> FEATURE:
<223> OTHER INFORMATION: peptide fragment

<400> SEQUENCE: 8

Ala Tyr Tyr Leu Ile Val Arg Val Asn Arg Ile
1               5                   10

<210> SEQ ID NO 9
<211> LENGTH: 11
<212> TYPE: PRT
<213> ORGANISM: Artificial sequence
<220> FEATURE:
<223> OTHER INFORMATION: peptide fragment

<400> SEQUENCE: 9

Ala Thr Asn Lys Lys Thr Gly Arg Arg Pro Arg
1               5                   10

<210> SEQ ID NO 10
<211> LENGTH: 11
<212> TYPE: PRT
<213> ORGANISM: Artificial sequence
<220> FEATURE:
<223> OTHER INFORMATION: peptide fragment

<400> SEQUENCE: 10

Ala Lys Arg Asn Gly Pro Leu Ile Asn Arg Ile
1               5                   10

<210> SEQ ID NO 11
<211> LENGTH: 11
<212> TYPE: PRT
<213> ORGANISM: Artificial sequence
<220> FEATURE:
<223> OTHER INFORMATION: peptide fragment

<400> SEQUENCE: 11

Ala Lys Arg Ser Val Gln Lys Leu Asp Gly Gln
1               5                   10

<210> SEQ ID NO 12
<211> LENGTH: 11
<212> TYPE: PRT
<213> ORGANISM: Artificial sequence
<220> FEATURE:
<223> OTHER INFORMATION: peptide fragment

<400> SEQUENCE: 12

Ala Arg Gln Lys Thr Met Lys Pro Arg Arg Ser
1               5                   10
```

```
<210> SEQ ID NO 13
<211> LENGTH: 10
<212> TYPE: PRT
<213> ORGANISM: Artificial sequence
<220> FEATURE:
<223> OTHER INFORMATION: peptide fragment

<400> SEQUENCE: 13

Ala Gly Asp Tyr Asn Pro Asp Leu Asp Arg
1               5                   10

<210> SEQ ID NO 14
<211> LENGTH: 11
<212> TYPE: PRT
<213> ORGANISM: Artificial sequence
<220> FEATURE:
<223> OTHER INFORMATION: peptide fragment

<400> SEQUENCE: 14

Ala Arg Lys Thr Arg Glu Arg Lys Ser Lys Asp
1               5                   10

<210> SEQ ID NO 15
<211> LENGTH: 11
<212> TYPE: PRT
<213> ORGANISM: Artificial sequence
<220> FEATURE:
<223> OTHER INFORMATION: peptide fragment

<400> SEQUENCE: 15

Ala Ser Gln Ala Lys Arg Arg Lys Gly Pro Arg
1               5                   10

<210> SEQ ID NO 16
<211> LENGTH: 11
<212> TYPE: PRT
<213> ORGANISM: Artificial sequence
<220> FEATURE:
<223> OTHER INFORMATION: peptide fragment

<400> SEQUENCE: 16

Ala Pro Lys Leu Asp Arg Met Leu Thr Lys Lys
1               5                   10

<210> SEQ ID NO 17
<211> LENGTH: 11
<212> TYPE: PRT
<213> ORGANISM: Artificial sequence
<220> FEATURE:
<223> OTHER INFORMATION: peptide fragment

<400> SEQUENCE: 17

Ala Lys Lys Glu Lys Pro Asn Lys Pro Asn Asp
1               5                   10

<210> SEQ ID NO 18
<211> LENGTH: 11
<212> TYPE: PRT
<213> ORGANISM: Artificial sequence
<220> FEATURE:
<223> OTHER INFORMATION: peptide fragment

<400> SEQUENCE: 18

Ala Gln Met Gly Arg Gln Ser Ile Asp Arg Asn
1               5                   10

<210> SEQ ID NO 19
```

```
<211> LENGTH: 11
<212> TYPE: PRT
<213> ORGANISM: Artificial sequence
<220> FEATURE:
<223> OTHER INFORMATION: peptide fragment

<400> SEQUENCE: 19

Ala Glu Gly Gly Lys Lys Lys Met Arg Ala
1               5                   10

<210> SEQ ID NO 20
<211> LENGTH: 11
<212> TYPE: PRT
<213> ORGANISM: Artificial sequence
<220> FEATURE:
<223> OTHER INFORMATION: peptide fragment

<400> SEQUENCE: 20

Ala Lys Lys Lys Glu Gln Lys Gln Arg Asn Ala
1               5                   10

<210> SEQ ID NO 21
<211> LENGTH: 11
<212> TYPE: PRT
<213> ORGANISM: Artificial sequence
<220> FEATURE:
<223> OTHER INFORMATION: peptide fragment

<400> SEQUENCE: 21

Ala Lys Ser Arg Lys Gly Asn Ser Ser Leu Met
1               5                   10

<210> SEQ ID NO 22
<211> LENGTH: 11
<212> TYPE: PRT
<213> ORGANISM: Artificial sequence
<220> FEATURE:
<223> OTHER INFORMATION: peptide fragment

<400> SEQUENCE: 22

Ala Arg Lys Ser Arg Asp Met Thr Ala Ile Lys
1               5                   10

<210> SEQ ID NO 23
<211> LENGTH: 12
<212> TYPE: PRT
<213> ORGANISM: Artificial sequence
<220> FEATURE:
<223> OTHER INFORMATION: peptide fragment

<400> SEQUENCE: 23

Gly Arg Ile Leu Ala Arg Gly Glu Ile Asn Phe Lys
1               5                   10

<210> SEQ ID NO 24
<211> LENGTH: 12
<212> TYPE: PRT
<213> ORGANISM: Artificial sequence
<220> FEATURE:
<223> OTHER INFORMATION: peptide fragment

<400> SEQUENCE: 24

Gly Ser Ile Leu Ala Ser Gly Glu Ser Asn Phe Lys
1               5                   10

<210> SEQ ID NO 25
<211> LENGTH: 12
```

```
<212> TYPE: PRT
<213> ORGANISM: Artificial sequence
<220> FEATURE:
<223> OTHER INFORMATION: peptide fragment

<400> SEQUENCE: 25

Gly Arg Ile Leu Ala Arg Gly Ser Ser Asn Phe Lys
1               5                   10

<210> SEQ ID NO 26
<211> LENGTH: 12
<212> TYPE: PRT
<213> ORGANISM: Artificial sequence
<220> FEATURE:
<223> OTHER INFORMATION: peptide fragment

<400> SEQUENCE: 26

Gly Glu Ile Ser Val Gly Glu Ser Lys Phe Phe Leu
1               5                   10

<210> SEQ ID NO 27
<211> LENGTH: 11
<212> TYPE: PRT
<213> ORGANISM: Artificial sequence
<220> FEATURE:
<223> OTHER INFORMATION: peptide fragment
<220> FEATURE:
<221> NAME/KEY: MOD_RES
<222> LOCATION: (3)..(3)
<223> OTHER INFORMATION: ACETYLATION
<220> FEATURE:
<221> NAME/KEY: MOD_RES
<222> LOCATION: (4)..(4)
<223> OTHER INFORMATION: ACETYLATION
<220> FEATURE:
<221> NAME/KEY: MOD_RES
<222> LOCATION: (6)..(6)
<223> OTHER INFORMATION: ACETYLATION
<220> FEATURE:
<221> NAME/KEY: MOD_RES
<222> LOCATION: (8)..(8)
<223> OTHER INFORMATION: ACETYLATION
<220> FEATURE:
<221> NAME/KEY: MOD_RES
<222> LOCATION: (10)..(10)
<223> OTHER INFORMATION: ACETYLATION

<400> SEQUENCE: 27

Ala Ser Lys Lys Pro Lys Arg Asn Ile Lys Ala
1               5                   10

<210> SEQ ID NO 28
<211> LENGTH: 11
<212> TYPE: PRT
<213> ORGANISM: Artificial sequence
<220> FEATURE:
<223> OTHER INFORMATION: peptide fragment

<400> SEQUENCE: 28

Ala Ser Lys Lys Pro Lys Ala Asn Ile Lys Ala
1               5                   10

<210> SEQ ID NO 29
<211> LENGTH: 11
<212> TYPE: PRT
<213> ORGANISM: Artificial sequence
<220> FEATURE:
<223> OTHER INFORMATION: peptide fragment

<400> SEQUENCE: 29
```

```
Ala Ser Lys Lys Pro Ala Ala Asn Ile Lys Ala
1               5                   10
```

<210> SEQ ID NO 30
<211> LENGTH: 11
<212> TYPE: PRT
<213> ORGANISM: Artificial sequence
<220> FEATURE:
<223> OTHER INFORMATION: peptide fragment

<400> SEQUENCE: 30

```
Ala Ser Lys Ala Pro Ala Ala Asn Ile Lys Ala
1               5                   10
```

<210> SEQ ID NO 31
<211> LENGTH: 11
<212> TYPE: PRT
<213> ORGANISM: Artificial sequence
<220> FEATURE:
<223> OTHER INFORMATION: peptide fragment

<400> SEQUENCE: 31

```
Ala Ser Ala Ala Pro Ala Ala Asn Ile Lys Ala
1               5                   10
```

<210> SEQ ID NO 32
<211> LENGTH: 11
<212> TYPE: PRT
<213> ORGANISM: Artificial sequence
<220> FEATURE:
<223> OTHER INFORMATION: peptide fragment

<400> SEQUENCE: 32

```
Ala Ser Lys Lys Ala Lys Arg Asn Ile Lys Ala
1               5                   10
```

<210> SEQ ID NO 33
<211> LENGTH: 11
<212> TYPE: PRT
<213> ORGANISM: Artificial sequence
<220> FEATURE:
<223> OTHER INFORMATION: peptide fragment

<400> SEQUENCE: 33

```
Ala Lys Lys Lys Lys Arg Ile Ser Ala Asn Pro
1               5                   10
```

<210> SEQ ID NO 34
<211> LENGTH: 11
<212> TYPE: PRT
<213> ORGANISM: Artificial sequence
<220> FEATURE:
<223> OTHER INFORMATION: peptide fragment

<400> SEQUENCE: 34

```
Pro Asn Ala Ser Ile Arg Lys Lys Lys Lys Ala
1               5                   10
```

<210> SEQ ID NO 35
<211> LENGTH: 11
<212> TYPE: PRT
<213> ORGANISM: Artificial sequence
<220> FEATURE:
<223> OTHER INFORMATION: peptide fragment

<400> SEQUENCE: 35

```
Lys Asn Ser Pro Lys Ala Arg Ile Lys Ala Lys
```

```
<210> SEQ ID NO 36
<211> LENGTH: 11
<212> TYPE: PRT
<213> ORGANISM: Artificial sequence
<220> FEATURE:
<223> OTHER INFORMATION: peptide fragment

<400> SEQUENCE: 36

Arg Thr Lys Gln Asp Lys Ala Gln Glu Arg Lys
1               5                   10

<210> SEQ ID NO 37
<211> LENGTH: 11
<212> TYPE: PRT
<213> ORGANISM: Artificial sequence
<220> FEATURE:
<223> OTHER INFORMATION: peptide fragment

<400> SEQUENCE: 37

Gly Leu Lys Arg Trp Ala Pro Asn Lys Ala Ala
1               5                   10

<210> SEQ ID NO 38
<211> LENGTH: 6
<212> TYPE: PRT
<213> ORGANISM: Artificial sequence
<220> FEATURE:
<223> OTHER INFORMATION: peptide fragment

<400> SEQUENCE: 38

Lys Lys Lys Lys Lys Lys
1               5

<210> SEQ ID NO 39
<211> LENGTH: 11
<212> TYPE: PRT
<213> ORGANISM: Artificial sequence
<220> FEATURE:
<223> OTHER INFORMATION: peptide fragment

<400> SEQUENCE: 39

Ala Lys Arg Asn Gly Pro Leu Ile Asn Arg Ile
1               5                   10

<210> SEQ ID NO 40
<211> LENGTH: 11
<212> TYPE: PRT
<213> ORGANISM: Artificial sequence
<220> FEATURE:
<223> OTHER INFORMATION: peptide fragment

<400> SEQUENCE: 40

Ala Lys Arg Ser Val Gln Lys Leu Asp Gly Gln
1               5                   10

<210> SEQ ID NO 41
<211> LENGTH: 10
<212> TYPE: PRT
<213> ORGANISM: Artificial sequence
<220> FEATURE:
<223> OTHER INFORMATION: peptide fragment

<400> SEQUENCE: 41

Ala Ser Thr Lys Arg Ser Met Gln Gly Ile
1               5                   10
```

```
<210> SEQ ID NO 42
<211> LENGTH: 11
<212> TYPE: PRT
<213> ORGANISM: Artificial sequence
<220> FEATURE:
<223> OTHER INFORMATION: peptide fragment

<400> SEQUENCE: 42

Ala Thr Asn Lys Lys Thr Gly Arg Arg Pro Arg
1               5                   10

<210> SEQ ID NO 43
<211> LENGTH: 11
<212> TYPE: PRT
<213> ORGANISM: Artificial sequence
<220> FEATURE:
<223> OTHER INFORMATION: peptide fragment

<400> SEQUENCE: 43

Ala Arg Ala Leu Asn Trp Gly Ala Lys Pro Lys
1               5                   10

<210> SEQ ID NO 44
<211> LENGTH: 11
<212> TYPE: PRT
<213> ORGANISM: Artificial sequence
<220> FEATURE:
<223> OTHER INFORMATION: peptide fragment

<400> SEQUENCE: 44

Ala Arg Gln Lys Thr Met Lys Pro Arg Arg Ser
1               5                   10

<210> SEQ ID NO 45
<211> LENGTH: 11
<212> TYPE: PRT
<213> ORGANISM: Artificial sequence
<220> FEATURE:
<223> OTHER INFORMATION: peptide fragment

<400> SEQUENCE: 45

Ala Lys Lys Glu Lys Pro Asn Lys Pro Asn Asp
1               5                   10

<210> SEQ ID NO 46
<211> LENGTH: 11
<212> TYPE: PRT
<213> ORGANISM: Artificial sequence
<220> FEATURE:
<223> OTHER INFORMATION: peptide fragment

<400> SEQUENCE: 46

Ala Arg Lys Thr Lys Ser Arg Glu Arg Lys Asp
1               5                   10

<210> SEQ ID NO 47
<211> LENGTH: 11
<212> TYPE: PRT
<213> ORGANISM: Artificial sequence
<220> FEATURE:
<223> OTHER INFORMATION: peptide fragment

<400> SEQUENCE: 47

Ala Thr Asn Lys Lys Thr Gly Arg Arg Pro Arg
1               5                   10
```

<210> SEQ ID NO 48
<211> LENGTH: 848
<212> TYPE: PRT
<213> ORGANISM: Homo sapiens
<220> FEATURE:
<223> OTHER INFORMATION: NCAM-140

<400> SEQUENCE: 48

```
Met Leu Gln Thr Lys Asp Leu Ile Trp Thr Leu Phe Phe Leu Gly Thr
1               5                   10                  15

Ala Val Ser Leu Gln Val Asp Ile Val Pro Ser Gln Gly Glu Ile Ser
            20                  25                  30

Val Gly Glu Ser Lys Phe Phe Leu Cys Gln Val Ala Gly Asp Ala Lys
        35                  40                  45

Asp Lys Asp Ile Ser Trp Phe Ser Pro Asn Gly Glu Lys Leu Thr Pro
50                  55                  60

Asn Gln Gln Arg Ile Ser Val Val Trp Asn Asp Asp Ser Ser Ser Thr
65                  70                  75                  80

Leu Thr Ile Tyr Asn Ala Asn Ile Asp Asp Ala Gly Ile Tyr Lys Cys
                85                  90                  95

Val Val Thr Gly Glu Asp Gly Ser Glu Ser Glu Ala Thr Val Asn Val
            100                 105                 110

Lys Ile Phe Gln Lys Leu Met Phe Lys Asn Ala Pro Thr Pro Gln Glu
        115                 120                 125

Phe Arg Glu Gly Glu Asp Ala Val Ile Val Cys Asp Val Val Ser Ser
130                 135                 140

Leu Pro Pro Thr Ile Ile Trp Lys His Lys Gly Arg Asp Val Ile Leu
145                 150                 155                 160

Lys Lys Asp Val Arg Phe Ile Val Leu Ser Asn Asn Tyr Leu Gln Ile
                165                 170                 175

Arg Gly Ile Lys Lys Thr Asp Glu Gly Thr Tyr Arg Cys Glu Gly Arg
            180                 185                 190

Ile Leu Ala Arg Gly Glu Ile Asn Phe Lys Asp Ile Gln Val Ile Val
        195                 200                 205

Asn Val Pro Pro Thr Ile Gln Ala Arg Gln Asn Ile Val Asn Ala Thr
210                 215                 220

Ala Asn Leu Gly Gln Ser Val Thr Leu Val Cys Asp Ala Glu Gly Phe
225                 230                 235                 240

Pro Glu Pro Thr Met Ser Trp Thr Lys Asp Gly Glu Gln Ile Glu Gln
                245                 250                 255

Glu Glu Asp Asp Glu Lys Tyr Ile Phe Ser Asp Asp Ser Ser Gln Leu
            260                 265                 270

Thr Ile Lys Lys Val Asp Lys Asn Asp Glu Ala Glu Tyr Ile Cys Ile
        275                 280                 285

Ala Glu Asn Lys Ala Gly Glu Gln Asp Ala Thr Ile His Leu Lys Val
290                 295                 300

Phe Ala Lys Pro Lys Ile Thr Tyr Val Glu Asn Gln Thr Ala Met Glu
305                 310                 315                 320

Leu Glu Glu Gln Val Thr Leu Thr Cys Glu Ala Ser Gly Asp Pro Ile
                325                 330                 335

Pro Ser Ile Thr Trp Arg Thr Ser Thr Arg Asn Ile Ser Ser Glu Glu
            340                 345                 350

Lys Thr Leu Asp Gly His Met Val Val Arg Ser His Ala Arg Val Ser
        355                 360                 365
```

```
Ser Leu Thr Leu Lys Ser Ile Gln Tyr Thr Asp Ala Gly Glu Tyr Ile
    370                 375                 380

Cys Thr Ala Ser Asn Thr Ile Gly Gln Asp Ser Gln Ser Met Tyr Leu
385                 390                 395                 400

Glu Val Gln Tyr Ala Pro Lys Leu Gln Gly Pro Val Ala Val Tyr Thr
                405                 410                 415

Trp Glu Gly Asn Gln Val Asn Ile Thr Cys Glu Val Phe Ala Tyr Pro
            420                 425                 430

Ser Ala Thr Ile Ser Trp Phe Arg Asp Gly Gln Leu Leu Pro Ser Ser
        435                 440                 445

Asn Tyr Ser Asn Ile Lys Ile Tyr Asn Thr Pro Ser Ala Ser Tyr Leu
    450                 455                 460

Glu Val Thr Pro Asp Ser Glu Asn Asp Phe Gly Asn Tyr Asn Cys Thr
465                 470                 475                 480

Ala Val Asn Arg Ile Gly Gln Glu Ser Leu Glu Phe Ile Leu Val Gln
                485                 490                 495

Ala Asp Thr Pro Ser Ser Pro Ser Ile Asp Gln Val Glu Pro Tyr Ser
            500                 505                 510

Ser Thr Ala Gln Val Gln Phe Asp Glu Pro Glu Ala Thr Gly Gly Val
        515                 520                 525

Pro Ile Leu Lys Tyr Lys Ala Glu Trp Arg Ala Val Gly Glu Glu Val
    530                 535                 540

Trp His Ser Lys Trp Tyr Asp Ala Lys Glu Ala Ser Met Glu Gly Ile
545                 550                 555                 560

Val Thr Ile Val Gly Leu Lys Pro Glu Thr Thr Tyr Ala Val Arg Leu
                565                 570                 575

Ala Ala Leu Asn Gly Lys Gly Leu Gly Glu Ile Ser Ala Ala Ser Glu
            580                 585                 590

Phe Lys Thr Gln Pro Val Gln Gly Glu Pro Ser Ala Pro Lys Leu Glu
        595                 600                 605

Gly Gln Met Gly Glu Asp Gly Asn Ser Ile Lys Val Asn Leu Ile Lys
    610                 615                 620

Gln Asp Asp Gly Gly Ser Pro Ile Arg His Tyr Leu Val Arg Tyr Arg
625                 630                 635                 640

Ala Leu Ser Ser Glu Trp Lys Pro Glu Ile Arg Leu Pro Ser Gly Ser
                645                 650                 655

Asp His Val Met Leu Lys Ser Leu Asp Trp Asn Ala Glu Tyr Glu Val
            660                 665                 670

Tyr Val Val Ala Glu Asn Gln Gln Gly Lys Ser Lys Ala Ala His Phe
        675                 680                 685

Val Phe Arg Thr Ser Ala Gln Pro Thr Ala Ile Pro Ala Asn Gly Ser
    690                 695                 700

Pro Thr Ser Gly Leu Ser Thr Gly Ala Ile Val Gly Ile Leu Ile Val
705                 710                 715                 720

Ile Phe Val Leu Leu Leu Val Val Asp Ile Thr Cys Tyr Phe Leu
                725                 730                 735

Asn Lys Cys Gly Leu Phe Met Cys Ile Ala Val Asn Leu Cys Gly Lys
            740                 745                 750

Ala Gly Pro Gly Ala Lys Gly Lys Asp Met Glu Glu Gly Lys Ala Ala
        755                 760                 765

Phe Ser Lys Asp Glu Ser Lys Glu Pro Ile Val Glu Val Arg Thr Glu
    770                 775                 780

Glu Glu Arg Thr Pro Asn His Asp Gly Gly Lys His Thr Glu Pro Asn
```

-continued

```
                785                 790                 795                 800
Glu Thr Thr Pro Leu Thr Glu Pro Glu Lys Gly Pro Val Glu Ala Lys
                    805                 810                 815

Pro Glu Cys Gln Glu Thr Glu Thr Lys Pro Ala Pro Ala Glu Val Lys
            820                 825                 830

Thr Val Pro Asn Asp Ala Thr Gln Thr Lys Glu Asn Glu Ser Lys Ala
        835                 840                 845

<210> SEQ ID NO 49
<211> LENGTH: 76
<212> TYPE: DNA
<213> ORGANISM: Artificial sequence
<220> FEATURE:
<223> OTHER INFORMATION: PCR primer

<400> SEQUENCE: 49
ctgcaggtag atattgttcc cagccaagga gccatcagcg ttggagcctc ccgccttctt      60
cctgtgtcaa gtggca                                                     76

<210> SEQ ID NO 50
<211> LENGTH: 72
<212> TYPE: DNA
<213> ORGANISM: Artificial sequence
<220> FEATURE:
<223> OTHER INFORMATION: PCR primer

<400> SEQUENCE: 50
attcacaatg acctgaatgt ccttgaagtt gatggccccg gcggccagga tggcgccgtg      60
acagcggtaa gt                                                         72
```

NCAM BINDING COMPOUNDS

The present invention relates to treatment of diseases and conditions of the central and peripheral nervous system, treatment of diseases and conditions of muscles and treatment of diseases and conditions of various organs. In particular, the present invention concerns new compounds which are capable of stimulating proliferation of and/or neurite outgrowth from cells presenting the neural cell adhesion molecule (NCAM), such as neurones. In a further aspect, the present invention relates to compositions, and medicaments as well as methods for treating normal, degenerated or damaged NCAM presenting cells.

BACKGROUND OF THE INVENTION

The brain and thus nerve cells and their function have during the last decades become an increasing subject of scientific investigations. Without doubt, the proper function of this complex system is extremely important for the proper function of the body and mind. It has been found that physical and mental malfunction can be related to i.a. abnormalities in level of signalling compounds, including neurotransmitters. Some malfunctions can be related to decay of nerve cells (neurones), connections between nerve cells and connections between muscle cells and nerve cells. This is e.g. the case in neurodegenerative diseases such as Alzheimer's Disease, where death of nerve cells leads to senility.

During the development of the brain, connections between nerve cells (neurones) are formed. Such connections are necessary for communication between neurones to occur, allowing individual neurones to function together as a whole. In the mature brain, connections between neurones are constantly remodulated to accommodate new demands from a changing environment. The ability to remodulate neural connections is crucial in learning and memory and in regeneration, e.g. after damage to the brain or in neurodegenerative diseases.

It is believed that the mechanisms controlling the formations of neural contacts are generally similar in the developing and the mature. Several mechanisms are involved in the formation of contacts between neurones including cell adhesion, the formation of nerve cell extensions (neurites), fasciculation (bundling of individual neurites) and formation of contact points (synapses).

Cell adhesion molecules (CAMs) constitute a group of proteins mediating adhesion between cells. A major group of CAMs belongs to the immunoglobulin (Ig) superfamily characterised by the presence of immunoglobulin domains. The neural cell adhesion molecule (NCAM) is such a cell adhesion molecule of the Ig superfamily that is particularly abundant in the nervous system. NCAM is expressed in the outer membrane of nerve cells. When one NCAM molecule binds to another NCAM molecule on another cell, the binding between the two cells is strengthened. NCAM not only binds to NCAM but also to other proteins found on nerve cells or in the extracellular substance of the brain (the extracellular matrix). By mediating adhesion between nerve cells—or between nerve cells and the extracellular matrix—NCAM influences migration of cells, extension of neurites, fasciculation of neurites and formation of synapses.

NCAM expression is correlated with morphogenic events suggesting that NCAM is important during development (Edelman 90). Thus, NCAM as believed to be important for the development of the nervous system (Daston et al 1996) and various organs including the kidney (Lackie et al 1990), the liver (Knittel et al 1996), the bowel (Romanska et al 1996), the heart (Gaardsvoll et al 1993), the gonads (Møller et al 1991), the pancreas (Møller et al 1992), and the muscles (Landmesser et al 1990). Therefore, ligands capable of influencing NCAM function may potentially be beneficial in conditions of impaired development of these organs by inducing appropriate differentiation of target cells (Walsh et al 1990). In the brain, the role of NCAM has been supported by knock out mice which have altered development of certain brain regions, including the olfactory system, the hippocampus, the cerebellum and the retina (Cremer et al 1994). In these tissues, the lack of NCAM expression impairs migration of cells (Ono et al 1994) and outgrowth and fasciculation of neurites (Cremer et al 1997) which in turn leads to altered synaptogenesis and morphological and functional changes. Transgenic mice with a change in the NCAM gene to produce only soluble NCAM forms die before birth further indicating that NCAM functions have great potential to interfere with development (Rabinowitz et al 1996).

In the mature nervous system, NCAM have been shown to be important for the plasticity of neuronal connections associated with regeneration, learning and memory (Fields et al 1996). In the peripheral nervous system, NCAM is believed to be necessary for outgrowth of nerve fibres and formation of nerve-muscle connections in regeneration after damage including lesions (Nieke et al 1985) and stroke (Jucker et al 1995).

Moreover, NCAM is presumably involved in ageing-related impairments in the ability to regenerate peripheral nerves and nerve-muscle connections (Olsen et al 1995) as well as in a number of degenerative muscle diseases (Walsh et al 1985). A similar role of NCAM has been observed in the central nervous system where NCAM is believed to be important for neuritic outgrowth, fasciculation, branching and probably target recognition associated with regeneration (Daniloff et al 1986). In addition, NCAM-MAG double knock out mice have shown that NCAM is also necessary for myelination of neuronal fibres which is of crucial importance for neuronal function (Carenini et al 1997). In learning, subtle remodelling of neuronal connections is necessary for the stabilisation of a memory trace and it has been shown that NCAM expression changes concomitant with such changes (Doyle et al 1992). Moreover, interference with NCAM function by antibodies or in knock out mice impairs the ability to learn (Luthi et al., 1994; Rønn et al., 1995; Scholey et al 1993). From knock out mice, it has become evident that NCAM is also involved in other behavioural phenomena. Thus, NCAM knock out mice have altered circadian rhythm (Shen et al 1997) and males shown increased aggression (Stork et al 1997). In humans, elevated levels of soluble NCAM forms have been shown in schizophrenia (van Kammen et al 1998) and sclerosis (Massaro et al 1987) suggesting that NCAM could be of importance for these diseases.

NCAM is found in three main forms of which two are transmembrane forms while the third form is attached to the membrane by a lipid anchor (see FIG. 1) All three forms have the same structure extracellularly consisting of five immunoglobulin domains (Ig domains) and two fibronectin like domains (FnIII domains). A precursor form of the NCAM contains a signal sequence. The amino acid sequence of 140 Kd isoform precursor of human NCAM, is shown in FIG. 17. The Ig domains are numbered one to five from the N-terminal, that is Ig1 to Ig5. The fibronectin domains are likewise called FnIII1 and FnIII2. In addition to mediating cell adhesion, NCAM affect signal transduction in cells (Schuch et al 1989). When an NCAM molecule at the cell surface binds to another cell, a signal is transmitted to the interior of the cell (transmembrane signalling). Within the cell, a signalling cascade is activated that subsequently influences the behaviour of the cell it has been shown that signalling initiated by NCAM binding can stimulate neurite extension (Doherty et al., 1996).

It is unclear, which of the NCAM domains mediate cell adhesion and signal transduction. The generally accepted hypothesis predicts that homophilic NCAM adhesion is mediated by a transreciprocal interaction between the Ig3 domains of two opposing NCAM molecules. Considerable evidence supports this notion and a putative binding site has been identified (Rao et al 1992, Rao et al 1994, Sandig et al 1994). Also ligands affecting the Ig3 domain have been shown to inhibit NCAM mediated cell adhesion. A recent hypothesis predicts that not only the Ig3 but all five Ig-domains mediate homophilic NCAM binding (Ranheim 96). According to this hypothesis, Ig1 of one NCAM molecule binds to Ig5 of another NCAM molecule, Ig2 binds Ig4 and Ig3 binds to Ig3. Thus these two theories of NCAM binding are partially overlapping. The present inventors and their colleagues have recently proposed that a double reciprocal interaction between Ig1 and Ig2 domains of two opposing NCAM molecules may mediate homophilic NCAM binding (Thomsen et al. (1996), Kiselyov et al. (1997), Rønn (1997). Rønn observed an inhibition of aggregation of neurones in a culture of hippocampal cells when adding small peptides which were previously identified as capable of binding to the NCAM Ig1 domain. An additional stimulation of neurite outgrowth was also seen. Rønn neither disclosed the sequence of the peptides studies nor suggested an exploitation of his observations in medical treatment. In conclusion, the mechanism of homophilic NCAM binding is still a matter of debate although most researchers in the field favour the hypothesis of a an reciprocal interaction between all five Ig domains or at least between the Ig3 domains of two opposing NCAM molecules.

Antibodies against NCAM, purified NCAM protein and recombinant NCAM domains have been shown to induce signal transduction in certain cells. High concentrations of NCAM antibody can induce a transient calcium increase as well as a pH change in some but not all neuronal cells. (Schuch et al 1989). The recombinant NCAM domains Ig1 and Ig2 and the combined domains Ig1–5 can induce a similar transient calcium increase and change in pH in certain cells (Frei et al 1992). When used as a substrate or expressed by a monolayer of cells, the NCAM protein can stimulate neurite extension. The response depends on an interaction between the FnIII domains of NCAM with fibroblast growth factor (FGF)-receptors (Doherty et al 1996). In addition, an interaction between the cytoplasmic part of NCAM with the tyrosine kinase fyn is of importance for neurite outgrowth (Beggs et al 1997).

This interaction is believed to activate the Ras-MAP-Kinase pathway (Schmid, R-S et al 1999).

Also, recombinant NCAM domains immobilised to the substratum can stimulate neurite extension, branching of neurites or fasciculation of neurites. Thus the FnIII domains of NCAM can increase branching of neurites when used as a substratum (Stahlhut et al 1997, Kasper et al 1996). Moreover, the FnIII domains have been reported to be the most potent NCAM, domains to influence cell spreading and neurite outgrowth. Ig 1–5 also influenced these processes but less potently than the FnIII domains (Frei et al 1992). In contrast, Ig1 and Ig2 most potently promoted cell adhesion and cell migration in this study (Frei et al 1992). Frei et al also observed stimulation of neurite outgrowth by the isolated NCAM domains Ig3, Ig4, Ig5, FnIII,1 and FnIII,2, but not by Ig1 and Ig2. A sequence located between the Ig5 and the FnIII,1 domains have been shown to be important for fasciculation of neurites (Pollerberg et al 1993). The Ig5 domain, of NCAM is of major importance for neurite outgrowth due to the presence or absence of the sugar chains polysialic acid (PSA) on this domain (Rutishauser et al 1996). Likewise, the Ig4 domain is important due to the presence or absence of the alternatively spliced domain VASE (Doherty et al 1992). Synthetic peptides corresponding to the VASE sequence have been shown to interfere with NCAM stimulated neurite outgrowth (Lahrtz et al 1997). Moreover, the NCAM Ig4 domain is presumed to bind another cell adhesion molecule, L1, and thereby to influence neurite outgrowth (Horstkorte et al 1993). In contrast to the effect of immobilised reagents, NCAM antibodies or recombinant domains inhibit neurite outgrowth when added in solution. Peptides corresponding to the presumed homophilic binding site in Ig3 or mutations in this sequence in the Ig3 domain have been shown to inhibit neurite outgrowth stimulated by NCAM (Sandig et al 1994).

However, an antibody against NCAM has recently been shown to stimulate neurite outgrowth (U.S. Pat. No. 5,667,978). This antibody recognises the Ig3 domain of NCAM. All NCAM domains have moreover been shown to influence proliferation of glial cells, neuroblastoma cells and fibroblasts, the Ig3 domain being the most potent. This function has been shown to require interaction with MAP kinase activity (Krushel 1998). It has been shown that various inhibitory ligands of the NCAM Ig3 domain, including small peptides corresponding to parts of the Ig3 domain sequence, can inhibit glial proliferation (WO 96/18103).

These data suggest, that the NCAM protein or NCAM ligands could potentially influence functions of the nervous system and other tissues. Inhibiting glial proliferation would potentially be beneficial in degenerative conditions (WO 96/18103, U.S. Pat. No. 5,625,040, U.S. Pat. No. 5,667, 978). Alternatively, if NCAM functions, particularly the induction of neurite outgrowth, could be stimulated, a beneficial effect on brain function would be possible. A stimulation of certain in vitro NCAM functions has been described for an antibody against NCAM Ig3 (U.S. Pat. No. 5,667,978). However, no small ligands of NCAM with significant stimulatory effect on NCAM functions has been described. Moreover, it is not evident to which NCAM domain such a ligand should be targeted. Most evidence points at the NCAM Ig3 domain as the crucial domain for homophilic binding while the cytoplasmic part of NCAM together with the FnIII domains are presumed to be most important for interactions with signalling molecules.

In the Ph.D. thesis "NCAM and Neural Plasticity" (Rønn 1997), the role of NCAM in neural plasticity was studied. Different assays (test systems), including aggregation of neural cells, neurite extension and long-term potentiation (LTP) were used to study how the role or effect of NCAM was influenced by NCAM antibodies, NCAM fusion proteins and other NCAM ligands. Presumed NCAM ligands selected from a random peptide library were studied. The peptides were found to be able to bind Ig1. One specific peptide, which is not characterised further in the thesis, was shown to inhibit aggregation of neural cells and to stimulate neurite outgrowth. It is concluded that such ligands might be a valuable tool in the continued attempts to clarify the role of NCAM in the developing nervous system as well as in synaptic plasticity. A possible medical use of the investigated peptides is neither an object of the thesis nor suggested therein. Furthermore, the thesis does not disclose the sequences of the investigated peptides.

U.S. Pat. No. 5,625,040 relates to chondroitin sulphate proteoglycan (Phosphacan) and its use in enhancing regeneration of nerves by binding to NCAM. The Phosphacan sequence is 1616 amino acid residues long. Recombinant Phosphacan was obtained by cloning the encoding gene in a suitable vector. The gene was isolated using primers chosen in accordance with the identified amino acid sequences of some proteolytic fragments of Phosphacan. None of the fragments was suggested to possess a biological effect per se.

A stimulatory effect on the potential for neurite extension may be expected to have a beneficial effect in functions of the nervous system requiring plasticity of connections between nerve cells. Such functions include learning and memory and regeneration. It is therefore of considerable interest to identify substances with the capability to influence NCAM mediated signalling.

SUMMARY OF THE INVENTION

In accordance with the present invention, novel compounds are provided, which promote extension of neurites in the central and peripheral nervous system.

More specifically, the invention concerns compounds which (a) bind to the NCAM Ig1 domain and/or (b) bind to the NCAM to the NCAM Ig2 domain and are capable of stimulating neurite outgrowth from and/or proliferation of NCAM presenting cells. By the NCAM Ig1 domain and the NCAM Ig2 domain are understood the NCAM Ig1 polypeptide and the NCAM Ig2 polypeptide. These compounds include a) the group comprising the NCAM Ig2 polypeptide and fragments and mimics thereof and b) the group comprising the NCAM Ig1 polypeptide and fragments and mimics thereof.

Such compounds may be composed of natural occurring as well as synthetic amino acids, peptide nucleic, acids (PNA) monomers and/or peptidomimetics.

The present invention discloses a homophilic binding site in the NCAM molecule constituted by the combined (unified) Ig1 and Ig2 domain, which combination of domains hereinafter be notifiable as NCAM Ig1–Ig2 or as NCAM Ig1–Ig2 domains.

The invention includes thus compounds that bind to either the NCAM Ig1 domain (which corresponds to the above (a)) or the NCAM Ig2 domain (which corresponds to the above (b)). These two domains form together the herein disclosed homophilic binding site.

According to the present invention said compounds within (a) and (b) may respectively belong to three below disclosed groups of compounds (the compound groups I, II and III) which are capable of activating neurite outgrowth.

As to the compound group I, the compound may in particular be a peptide which binds to the 1st domain of NCAY. (NCAM Ig1) through a binding motif which comprises at least 2 basic amino acid residues, preferably at least 2 basic amino acid residues within a sequence of 10 amino acid residues and more preferably at least 2 basic amino acid residues within a sequence of 3 amino acid residues.

Interesting peptides comprise the sequence:

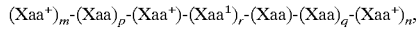

wherein Xaa$^+$ is a basic amino acid residue,
 Xaa$^1$ is any amino acid residue,
 Xaa is any amino acid residue, and m,n,p,q and r independently are 0 or 1, and wherein the basic amino acid residues preferably are lysine or arginine and r preferably is 1.

The nature of the amino acid residues Xaa and Xaa$^1$ does not seem to be important. It appears that they may be any amino acid residue. However, Xaa$^1$ is preferably proline (P) or glutamic acid (E).

In even more preferred peptides r is 1 and at least one of m and n is 1.

Preferred peptides of the invention comprise the sequence (K/R)$_{0-1}$-K/R-X-K/R), wherein X has the same meaning as Xaa$^1$, suitably the sequence K/R-K/R-X-K/R or K/R-X-K/R, more suitably the sequence K/R-P-K/R, K/R-K/R-P-K/R, K/R-K/R-E-K/R or K/R-K/R-E-K/R most suitably the sequence K-P-K, K-K-P-K, K-K-E-K or K-K-E-R. Examples are the sequences A-S-K-K-P-K-R-N-I-K-A (SEQ ID NO:1), A-K-K-E-R-Q-R-K-D-T-Q (SEQ ID NO:2), and A-R-A-L-N-W-G-A-K-P-K (SEQ ID NO:3).

As to the compound group II, the compound may be a peptide that binds to that part of the homophilic binding site of NCAM Ig1–Ig2 which is constituted by the Ig1 domain.

The binding motif comprises at least 2 basic amino acid residues and at least 1 apolar amino acid, preferably at least 2 basic amino acid residues and 1 apolar amino acid residue within a sequence of 12 amino acid residues. More preferably, the binding motif comprises at least 2 basic amino acid residues and at least 1 apolar amino acid within a sequence of 8 amino acid residues. Most preferably, the binding motif comprises at least 2 basic amino acid residues separated by 3 amino acids in addition to 1 apolar amino acid with 1 adjacent acid amino acid separated by 1 of the basic amino acid residues by 1 amino acids. Such peptides comply with the general sequence.

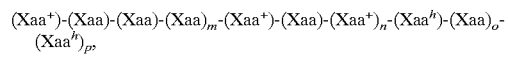

wherein Xaa$^+$ is a basic amino acid residue,
 Xaa$^-$ is a an acidic amino acid residue,
 Xaa$^h$ is a apolar amino acid residue,
 Xaa is any amino acid residue, and
 m,n,o and p independently are 0 or 1, and wherein the basic amino acid residues preferably are lysine or arginine, the acidic amino acids preferably are glutamic acid or aspartic acid, the apolar amino acids are preferably leucine, isoleucine, valine or phenylalanine, and r preferably is 1.

Preferred peptides of the invention comprise the sequence (K/R)-X-X-X-(K/R)-X-(E/D)-(L/I/V/F)-X-(L/I/V/F), wherein X is any amino acid residue, suitably the sequence (K/R)-X-(E/D)-(L/I/V/F)-X-(L/I/V/F), (K/R)-X-X-X-(K/R)-X-(E/D), (K/R)-X-X-(K/R)-X-(E/D) or (K/R)-X-(L/I/V/F)-X-(L/I/V/F), more suitably the sequences (K/R)-X-X-X-(K/R)-X-(E/D)-(L/I/V/F), (K/R)-X-X-(K/R)-X-(E/D)-(L/I/V/F) or (K/R)-X-X-X-(K/R)-X-(L/I/V/F), even more suitably the sequences (K/R)-X-X-(K/R)-X-(E/D)-(L/I/V/F), (K/R)-X-X-X-(K/R)-X-(L/I/V/F)-X-(L/I/V/F) or (K/R)-X-X-X-(K/R)-X-(E/D)-(L/I/V/F)-(L/I/V/F) and most suitably the sequence GRILARGEINFK (SEQ ID NO: 23).

As to the compound group III, the compound may be a peptide, that binds to that part of the homophilic binding site of NCAM Ig1–Ig2 which is constituted by the Ig2 domain.

The binding motif comprises at least 2 acidic amino acid residues and at least 1 apolar amino acid, preferably at least 2 acidic amino acid residues and 2 apolar amino acid residue within a sequence of 10 amino acid residues. More preferably, the binding motif comprises at least 2 acidic amino acid residues and at least 1 apolar amino acid within a sequence of 9 amino acid residues. Most preferably, the binding motif comprises at least 2 acidic amino acid residues separated by 4 amino acids, one of the acidic amino acids being separated by 1 amino acid from a basic amino acid and 2 adjacent apolar amino acids. Such peptides comply with the general sequence.

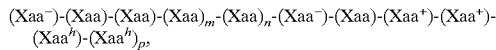

wherein Xaa⁺ is a basic amino acid residue,

Xaa⁻ is a an acidic amino acid residue,

Xaa$^h$ is an apolar amino acid residue,

Xaa is any amino acid residue, and m,n,o and p independently are 0 or 1, and wherein the basic amino acid residues preferably are lysine or arginine, the acidic amino acids preferably are glutamic acid or aspartic acid, the apolar amino acids are preferably leucine, isoleucine, valine or phenylalanine, and r preferably is 1.

Preferred peptides of the invention comprise the sequence (E/D)-X-X-X-(E/D)-X-(K/R)-(L/I/V/F)-X-(L/I/V/F), wherein X is any amino acid residue, suitably the sequence (E/D)-X-(K/R)-(L/I/V/F)-X-(L/I/V/F), (E/D)-X-(K/R)-(L/I/V/F)-(L/I/V/F), (E/D)-X-X-X-X-(E/D)-X-(K/R)-(L/I/V/F), (E/D)-X-X-X-(E/D)-X-(K/R)-(L/I/V/F) or (E/D)-X-X-(E/D)-X-(K/R)-(L/I/V/F), more suitably E/D)-X-X-(E/D)-X-(K/R)-(L/I/V/F)-X-(L/I/V/F/) or (E/D)-X-X-(E/D)-X-(K/R)-(L/I/V/F)-(L/I/V/F), even more suitably the sequences (E/D)-X-X-X-X-(E/D)-X-(K/R)-(L/I/V/F)-(L/I/V/F), (E/D-X-X-X-(E/D)-X-(K/R)-(L/I/V/F)-X-(L/I/V/F) or (E/D)-X-X-X-(E/D)-X-(K/R)-(L/I/V/F)-(L/I/V/F), and most suitably the sequence GEJSVGESKFFL (SEQ ID NO: 26).

The abbreviations of the amino acids follow the normal three and one letter codes: alanine (Ala,A), arginine (Arg,R), asparagine (Asn,N), aspartic acid (Asp,D), cysteine (Cys,C), glutamic acid (Glu,E), glutamine (Gln,Q), glycine (Gly,G), histidine (His,H), Isoleucine (Ile,I), leucine (Leu,L), lysine (Lys,K), methionine (Met,M), phenylalanine (Phe,F), proline (Pro,P), serine (Ser,S), threonine (Thr,T), tryptophan (Trp,W), tyrosine (Tyr,Y) and valine (Val,V).

In the present context, the term "amino acid" is intended to comprise naturally occurring amino acids as well as non-natural occurring amino acids. Non-natural occurring amino acids are i.a. modified naturally occurring amino acids.

The peptides may be modified, for example by acetylation.

The invention also concerns compounds which are anti-NCAM Ig1 antibodies, which mimic the binding of the NCAM Ig2 domain to the Ig1 domain. Such non-peptide molecules are e.g. PNAs or peptidomimetics. Examples of peptidomimetics are given in Marshall, G. R., Tetrahedron 49, 3547–3558 (1993), and include oligo(N-substituted glycines), oligocarbamates, oligosulphones and oligosulfoxides.

The invention further concerns compounds which are non-peptide molecules, which mimic the binding of the NCAM Ig2 domain to the Ig1 domain.

The invention even further concerns the NCAM Ig2 polypeptide, fragments or mimics thereof for use in the treatment of normal, degenerated or damaged NCAM presenting cells, said treatment consisting of stimulating neurite outgrowth from and/or proliferation of NCAM presenting cells.

The treatment may be a treatment of diseases and conditions of the central and peripheral nervous system, the muscles or various organs. The treatment may also be a stimulation of learning and memory.

In the present context, the term "conditions" is intended to cover any condition in need of treatment, whatever the need is in connection with a damage, disease or expected disease or in connection with a stimulation and/or improvement of normal conditions.

The invention also concerns the use of the NCAM Ig2 polypeptide or fragments or mimics thereof in the manufacture of a medicament for the treatment of normal, degenerated or damaged NCAM presenting cells.

The invention further concerns pharmaceutical compositions comprising one or more of the compounds according to the invention.

Further, the invention concerns a method of treating normal, degenerated or damaged. NCAM presenting cells which method comprises administration of an effective amount of one or more of the compounds according to the invention.

The treatment may be a treatment of diseases or conditions of the central and peripheral nervous system, such as postoperative nerve damage, traumatic nerve damage, impaired myelination of nerve fibers, postischaemic, e.g. resulting from a stroke, Parkinsons disease, Alzheimers disease, dementias such as multiinfarct dementia, sclerosis, nerve degeneration associated with diabetes mellitus, disorders affecting the circadian clock or neuro-muscular transmission, and schizophrenia; of diseases or conditions of the muscles including conditions with impaired function of neuro-muscular connections, such as genetic or traumatic atrophic muscle disorders; of diseases or conditions of various organs, such as degenerative conditions of the gonads, of the pancreas such as diabetes mellitus type I and II, of the kidney such as nephrosis or of the heart, liver or bowel. The treatment may also be a stimulation of the ability to learn and/or of the memory.

The invention also concerns a prosthetic nerve guide, which guide comprises one or more of the compounds according to the invention.

BRIEF DESCRIPTION OF THE FIGURES

FIG. 2 shows an identification of bead-coupled peptides binding NCAM domains. A) Libraries of bead-coupled. decapeptides are incubated with the recombinant NCAM Ig1domain. Beads that bind NCAM Ig1 are visualised by a staining reaction. Stained beads are isolated and microsequenced (Example 3 and 4). B) After evaluation of binding sequences, peptides corresponding to these sequences are synthesised as monomers, dendrimers (4-mers) or BSA-coupled 20-mers (Example S). C) Structure of peptide dendrimers. Four peptide-monomers ("peptide") are coupled to a backbone consisting of three lysines.

FIG. 3 shows single hippocampal cells (Example 7 (2)) maintained in the absence (A) or presence (B) of C3d (5.4*10⁻⁷ M).

FIG. 4 shows the peptide-sequences identified from combinatorial peptide libraries. A) 22 sequences identified from screening a combinatorial library with NCAM Ig1. B) Peptides from A) comprising parts of the motif K/R-K/R-P-K/R-N/S emphasised in bold. The C3 peptide is underlined. C) Peptides comprising parts of the motif K/R-K/R-E-K/R-X-K/R-K/R emphasised in bold. The D3 peptide is underlined. D) Peptides containing the motif G-X-K/R-P-K/R emphasised in bold. The D4 peptide is underlined.

FIG. 7 gives a summary of the NCAM Ig1 binding peptides and their effect on neurite-outgrowth and aggregation in cell cultures of primary hippocampal neurones. Effect on neurite-outgrowth is measured in cultures of dissociated neurones as described in example 7 (2). For "neur", 0 indicates no effect, + indicates stimulatory effect, ++ indicates strong stimulatory effect on neurite outgrowth. For "agg", 0 indicates no effect, − indicates inhibitory effect, − indicates strong inhibitory effect on 3C aggregation, the inhibitory effect being reflected as an increased number of aggregates formed. The peptide names and/or numbers correspond to peptides of the sequences indicated in the figure. The peptides are all tested as dendrimers.

FIG. 17 shows the predicted amino acid sequence of human NCAM, 140 KD isoform precursor (SWISS-PROT: locus NCA1-HUMAN, accession no. P13591).

FIG. 19. Effect of Ig domain 2, the monomeric Ig2-peptide and its derivatives on aggregations in primary cultures of dissociated hippocampal cells of rat embryos (E18). Cultures were grown for 24 h. The number of aggregates in cultures treated with compounds is expressed as a percentage of the number of aggregates in control cultures (100±10) Four individual experiments were performed. Results are given as mean ±SEM. (a) Comparison of the effects of Ig domain 2 (Ig2) and Ig2-peptide (Ig2-p), a dose-response study. (b). Comparison of the effects of Ig2-peptide (Ig2-p) and Ig2 peptides in which either Arg-2, Arg-6 and Ile-9 (P2-3S) or Arg-2, Arg-6, Glu-8 and Ile-9 (P2-4S) were substituted with Ser. The peptides were used at a concentration 180 $\mu$M.

DETAILED DESCRIPTION OF THE INVENTION

Figure 1:
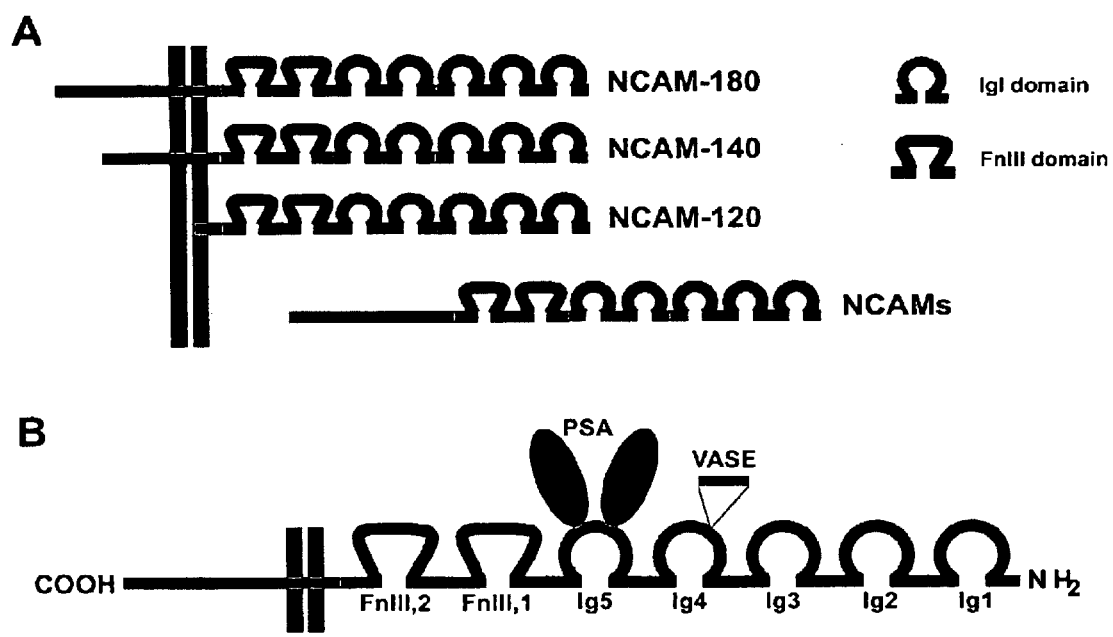
FIG. 1 shows the different forms of the neural cell adhesion molecule, NCAM. A) The main forms of NCAM all have similar extracellular parts consisting of five immunoglobulin-domains (Ig-domains) and two Fibronectin type III-domains (FnIII-domains). Three trans-membrane or membrane attached forms (NCAM-120, -140 and -180) are generated by alternative splicing. In addition, various soluble NCAM forms (NCAMs) exist. B) Individual NCAM-domains are numbered from the N-terminal (NH2), the most N-terminal domain being termed. NCAM Ig1. An important alternatively spliced exon is the VASE exon that can be inserted in the region encoding the Ig4 domain of NCAM. The Ig5 domain can be glycosylated with polysialic acid. (PSA).

In the nervous system, the ability to remodel connections between nerve cells is of major importance in the regeneration and well as in learning. Therefore, it is of considerable interest to identify substances that promote such processes. Much effort has been concentrated on identifying substances that stimulate neuronal survival and neuritic outgrowth in vitro as such substances will be expected to possess a potential to stimulate regeneration and learning. The neural cell adhesion molecule (NCAM) is believed to be important for the development and remodelling of neuronal connections and it is therefore of interest to identify ligands capable of stimulating NCAM-functions. It has previously been shown that antibodies against the Ig3 domain of NCAM can stimulate neurite outgrowth.

The present invention is based on the surprising finding that the NCAM Ig2 domain strongly stimulates the outgrowth of neurites from NCAM present cells. Thus, it has been found that NCAM Ig2 is a ligand of the NCAM Ig1 domain. It has further been found that the NCAM Ig2 domain stimulates neurite outgrowth by activation of specific signal transduction pathways.

Likewise, the present invention discloses the NCAM Ig1 domain as a ligand of the NCAM Ig2 domain and being capable of strong stimulation of the outgrowth of neurites from NCAM presenting cells by activation of specific signal transduction pathways.

The inventors have also, by means of combinatorial chemistry, identified small peptides which stimulate neurite outgrowth. Active peptides selected from a peptide library have been identified, and a putative motif comprising two or more basic amino acid residues has been identified. The peptides have been shown to stimulate the same specific signal transduction pathways as the NCAM Ig2 domain.

The results show that ligands of NCAM Ig1, either the NCAM Ig2 domain or small functional mimics hereof, which are capable of activating specific signalling pathways, can promote neurite outgrowth and thereby be of benefit in regeneration and learning. Other functional mimics of the NCAM Ig2 domain, such as antibodies and non-peptide molecules may be beneficial in the same way. Therefore, the present invention provides compounds and compositions which are or comprise small peptides, polypeptides which are or comprise small peptides, polypeptides, antibodies and non-peptide molecules recognizing the NCAM Ig1 domain. When applied to tissue containing NCAM-expressing cells these compounds and compositions will promote NCAM function. The compounds and the compositions can be applied to promote functions of the nervous system, the muscles and any other NCAM-expressing tissues, including various organs.

In its broadest aspect, the present invention relates to compounds which bind to the NCAM Ig1-domain and/or the NCAM, Ig2 domain and which are capable of stimulating neurite outgrowth from and/or proliferation of NCAM presenting cells. Such compounds may be a peptide or PNA sequence constituting the NCAM Ig2 domain, a fragment thereof or a mimic thereof.

Also, such compounds may be a peptide or PNA sequence constituting the NCAM Ig1 domain, a fragment thereof or a mimic thereof.

In the present context, a mimic of the Ig2 domain and the NCAM Ig1 domain should be understood to be any compound which binds to the NCAM Ig1 domain or the Ig2 domain, and through said binding stimulates neurite outgrowth from and/or proliferation of NCAM presenting cells. Mimics may be peptides, peptide derivatives, antibodies and non-peptide compounds such as small organic compounds, sugars and fats, as well as peptidomimetics.

In accordance with the present invention, novel compounds are provided, which promote extension of neurites in the central and peripheral nervous system. Surprisingly, it has been found that the compounds of the invention are able to promote formation and plasticity of neural connections.

It appears from the above, that the compounds of the present invention belong to three disclosed groups of compound (the compound groups I, II and III) which are capable of binding to the NCAM Ig1–Ig2 domains and thereby activate neurite outgrowth.

Further to compound group II, 22 peptides which were able to bind to recombinant, labelled neural cell adhesion compound Ig1 (NCAM Ig1) in vitro have been identified from a peptide library.

The 22 sequences are ASKKPKRNIKA (SEQ ID NO:1), AKKERQRKDTQ (SEQ ID NO:2), ARALNWGAKPK (SEQ ID NO:3), AGSAVKLKKKA (SEQ ID NO:4), AKYVLIPIRIS (SEQ ID NO:5), ASTKRSMQGI (SEQ ID NO:6), ARRAILM(Q/T/N)-AL (SEQ ID NO:7), AYYLIVRVNRI (SEQ ID NO:8), ATNKKTGRRPR (SEQ ID NO:9), AKRNGPLINRI (SEQ ID NO:10), AKRSVQKLDGQ (SEQ ID NO:11), ARQKTMKPRRS (SEQ ID NO:12), AGDYNPDLDR (SEQ ID NO:13), ARKTRERKSKD (SEQ ID NO:14), ASQAKRRKGPR (SEQ ID NO:15), APKLDRMLTKK (SEQ ID NO:16), AKKEKPNKPND (SEQ ID NO:17), AQMGRQSIDRN (SEQ ID NO:18), AEGGKKKKMRA (SEQ ID NO:19), AKKKEQKQRNA (SEQ ID NO:20), AKSRKGNSSLM (SEQ ID NO:21), ARKSRDMTAIK (SEQ ID NO:22).

Three peptides, C3 (SEQ ID NO:1), D3 (SEQ ID NO:2) and D4 (SEQ ID NO:3) (FIG. 4) were further investigated for their ability to bind the NCAM Ig1 domain using plasmon surface resonance analysis and selected according to their ability to inhibit aggregation of neurones and stimulate neurite outgrowth. By sequence analysis of these peptides and scrambled peptides, a motif for binding to NCAM Ig1 could surprisingly be identified. The motif includes positively charged amino acids in a relatively loose sequence-order, K/R (aa)$_{0-8}$ K/R, preferably K/R (aa)$_{0-1}$ K/R, wherein K and R designate lysine and arginine respectively and the positively charged amino acids are separated by up to 8 amino acid (aa) residues. Preferably, however, the positively charged amino acids are adjacent or separated by only one amino acid residue.

Analysis of the active peptides isolated from the peptide library suggests that the motif may comprise more than two positively charged amino acids, for example three or four basic amino acids.

Preferred peptides comprise the sequence:

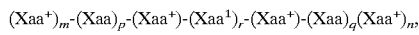

$(Xaa^+)_m\text{-}(Xaa)_p\text{-}(Xaa^+)\text{-}(Xaa^1)_r\text{-}(Xaa^+)\text{-}(Xaa)_q(Xaa^+)_n$, wherein $Xaa^+$ is a basic amino acid residue, $Xaa^1$ is any amino acid residue, Xaa is any amino acid residue, and m,n,p,q and r independently are 0 or 1.

and wherein the basic amino acid residues preferably are lysine or arginine and r preferably is 1.

The nature of the amino acid residues Xaa and $Xaa^1$ does not seem to be important. It appears that they may be any amino acid residue. However, $Xaa^1$ is preferably proline (P) or glutamic acid (E).

In even more preferred peptides r is 1 and at least one of m and n is 1.

Preferred peptides of the invention comprise the sequence $(K/R)_{0-1}\text{-}K/R\text{-}X\text{-}K/R)$, wherein X has the meaning of $Xaa^1$, suitably the sequence K/R-K/R-X-K/R or K/R-X-K/R, more suitably the sequence K/R-P-K/R, K/R-K/R-P-K/R, K/R-K/R-E-K/R or K/R-K/R-E-K/R and most suitably K-P-K, K-K-P-K, K-K-E-K or K-K-E-R. Examples are the sequences A-S-K-K-P-K-R-N-I-K-A (SEQ ID NO:1), A-K-K-E-R-Q-R-K-D-T-Q (SEQ ID NO:2), and A-R-A-L-N-W-G-A-K-P-K (SEQ ID NO:3).

According to the invention, peptides comprising the above sequence may be a part (hereinafter called a fragment) of the NCAM Ig2 domain or a mimic of the NCAM Ig2 domain. Furthermore, the peptides may bind to the Ig2 binding site of the Ig1 domain or to a different binding site on the Ig1 domain. If the binding site is not the "normal" Ig2 binding site, the binding will mimic the normal binding and result in neurite outgrowth and/or proliferation of NCAM presenting cells in the same way.

It is clear that the peptides of the invention are not limited to the decapeptides identified and selected from the synthetic peptide library. These peptides only served as tools for identifying a motif in peptide ligands expected to bind to the NCAM Ig1 domain.

Figure 18:
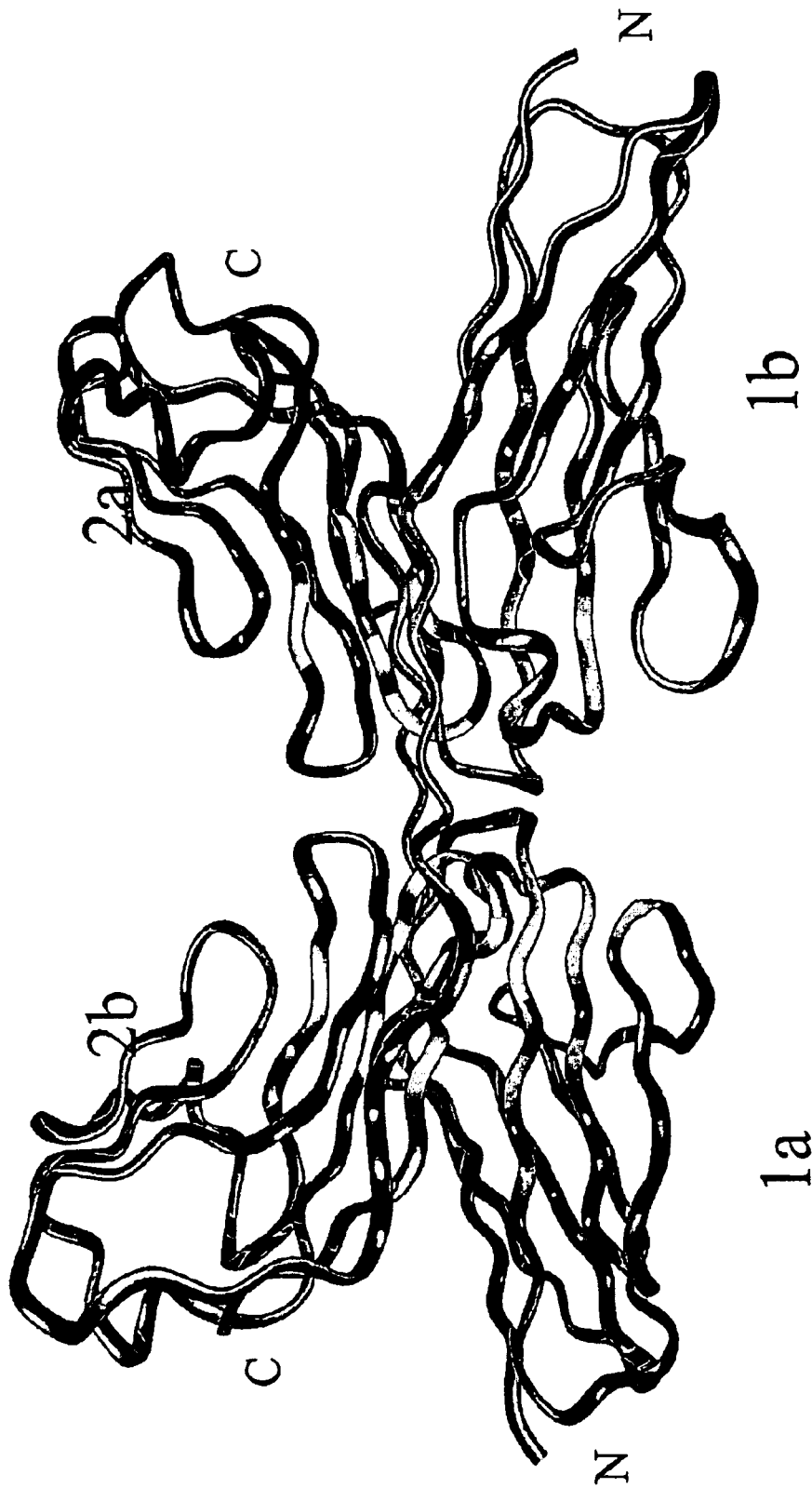
FIG. 18. The dimer of the first two domains of NCAM, (Ig1–Ig2). A) Ribbon presentation of the dimer light grey marks the binding site residues in Ig1 and Ig2. B) Space filling model of the two first domains of NCAM the dimer of the first two domains of NCAM, (Ig1–Ig2). The residues of the binding sites in the two domains are light grey. Key residues in the binding between Ig1 and Ig2 are marked with numbers corresponding to their position in the NCAM sequence. C) Ribbon presentation of the dimer showing the key electrostatic and hydrophobic interactions used in the modeling of the dimer structure.
Figure 18:
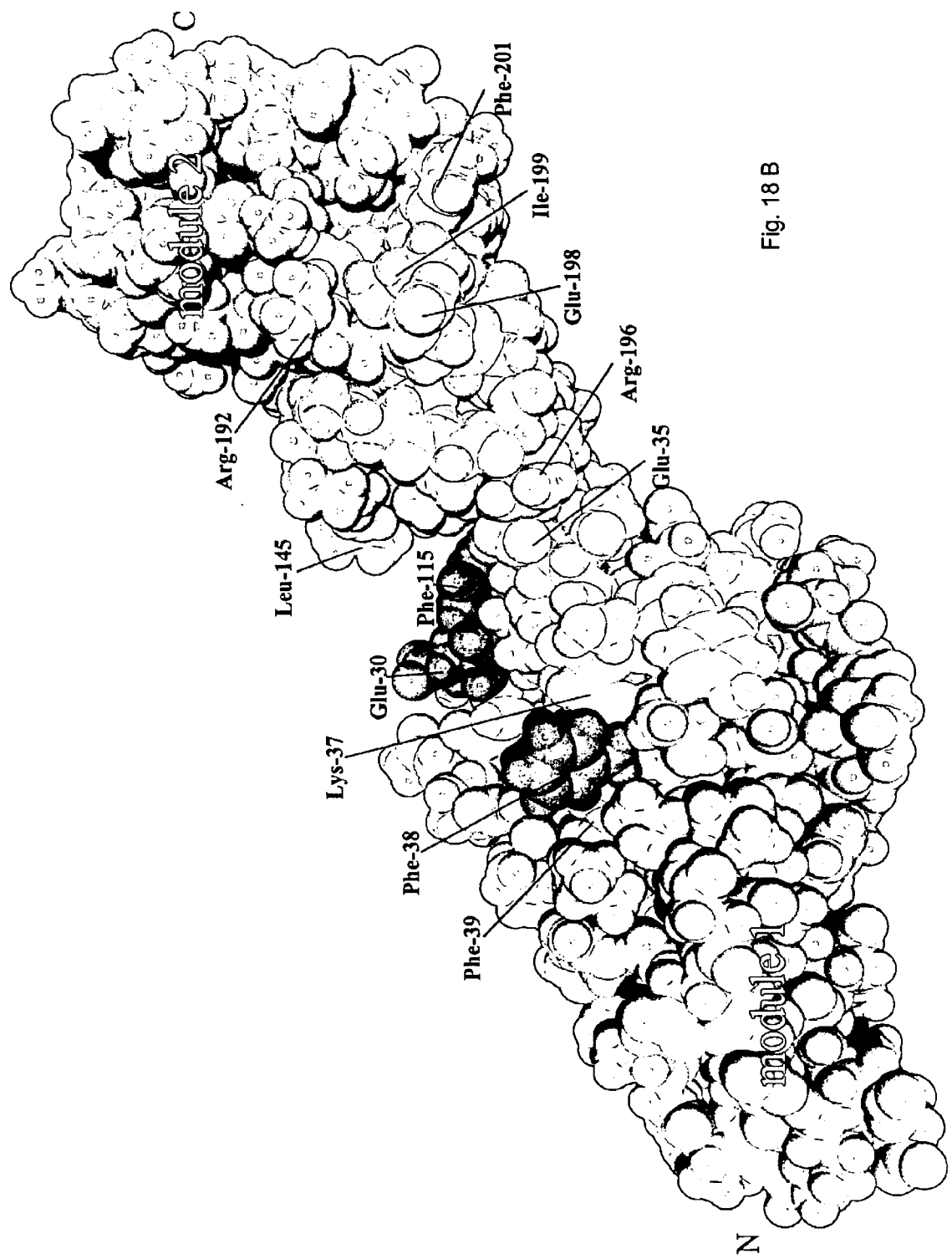
Figure 18:
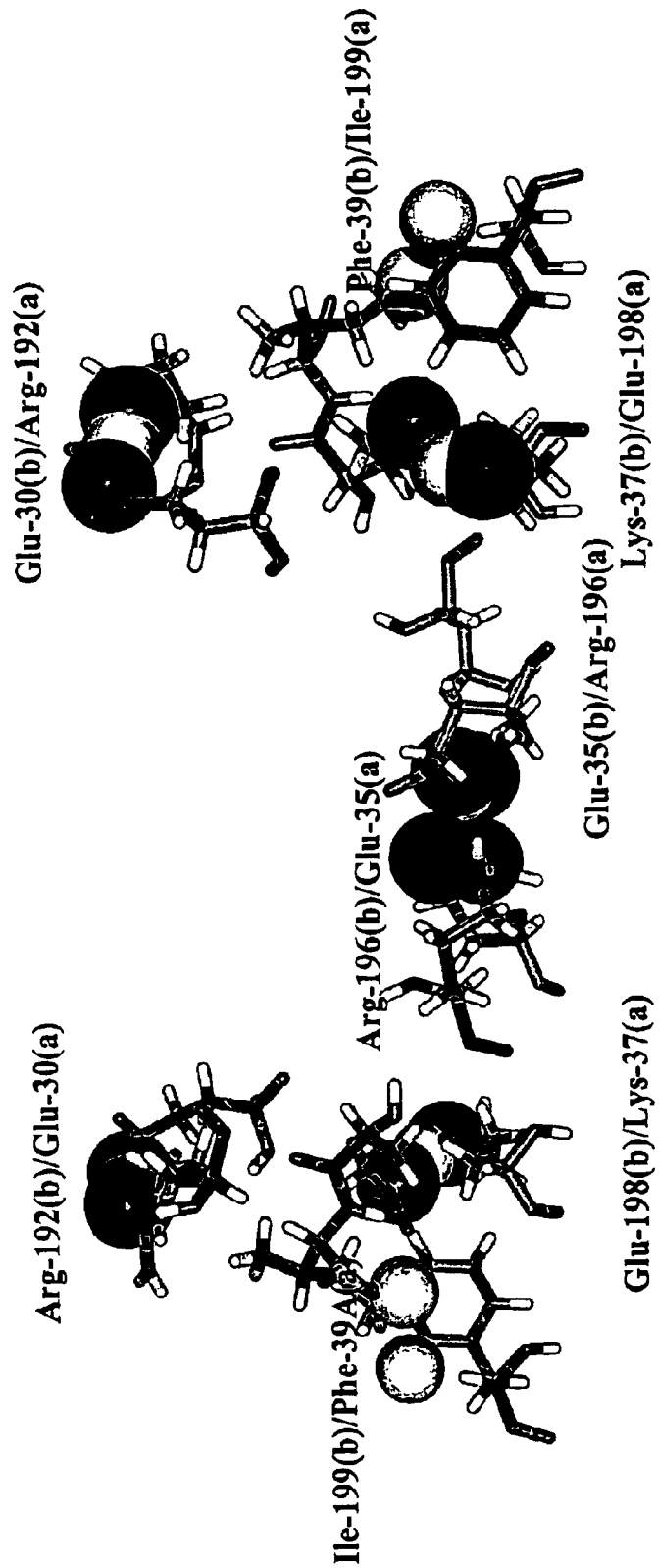
Figure 20:
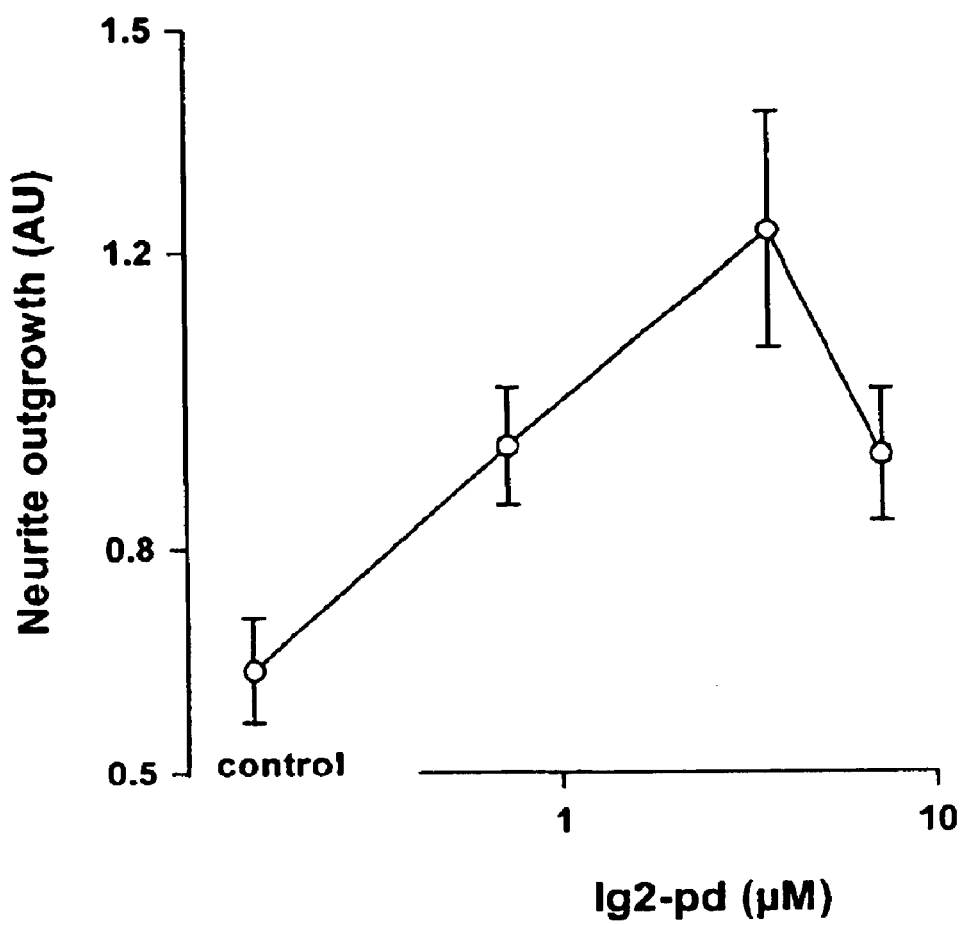
FIG. 20. Effect of Ig domain 2 (Ig2) and Ig2-peptide (Ig2-p) on neurite outgrowth from hippocampal neurons grown for 24 h. The length of neurites in treated cultures is expressed as a percentage of the length of neurites in control cultures. Four individual experiments were performed. Results are given as mean ±SEM.
Figure 21:
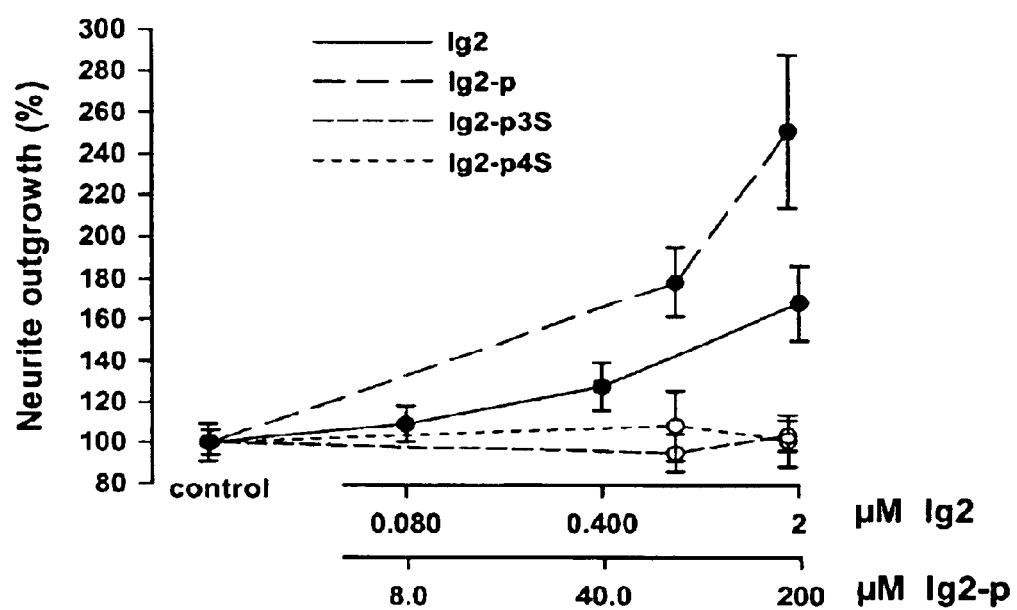
FIG. 21. Effect of Ig2-peptide (Ig2-p) and its derivatives (P2-3S and P2-4S) on neurite outgrowth from hippocampal neurons grown for 24 h. The length of neurites in treated cultures is expressed as a percentage of the length of neurites in control cultures. Four individual experiments were performed. Results are given as mean ±SEM.
Figure 22A:
FIG. 22. Phase contrast micrographs of a 24 h low-density culture of dissociated cells from hippocampus grown in the absence (a) or presence (b) of 3.6 $\mu$M Ig2-peptide (dendrimer) encompassing residues 191–202 of the Ig domain 2.
Figure 22B:
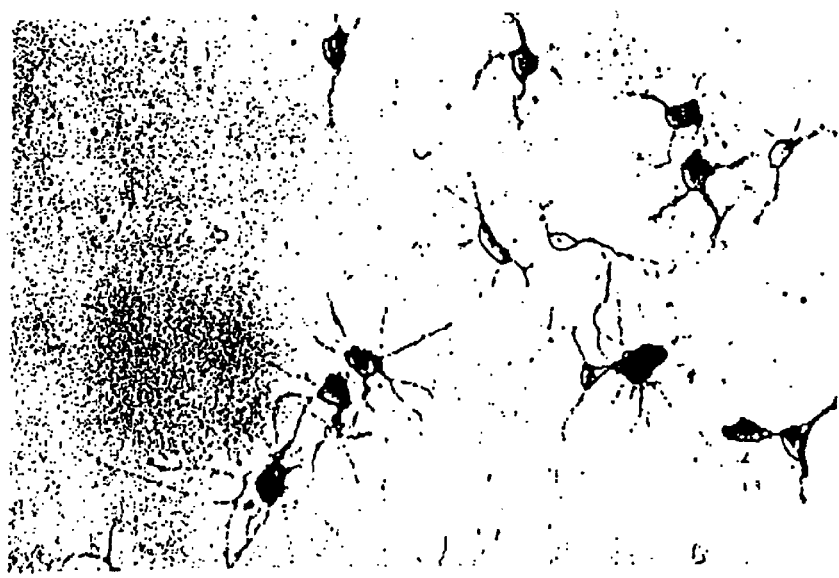
Figure 23:
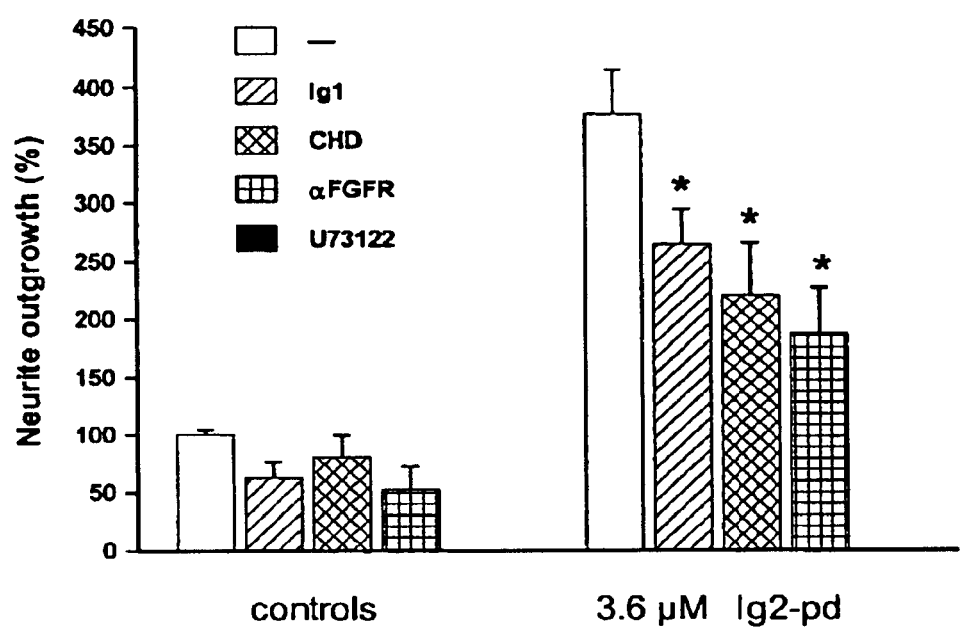
FIG. 23. Effect of Ig domain 1 of NCAM (Ig1, 25 $\mu$M), FGFR antibodies ($\alpha$-FGFR, diluted 1:2000), CAM homology domain peptide (CHD, 200 $\mu$M) and U-73122, an inhibitor of hospholipaseC$\gamma$ (5 $\mu$M), on neurite outgrowth from hippocampal neurons. Cultures were grown in the absence or in the presence of 3.6 $\mu$M Ig2-peptide (dendrimer, Ig-pd). The length of neurites in treated cultures is expressed as a percentage of the length of neurites in control cultures. Four individual experiments were performed. Results are given as mean ±SEM.
Figure 24:
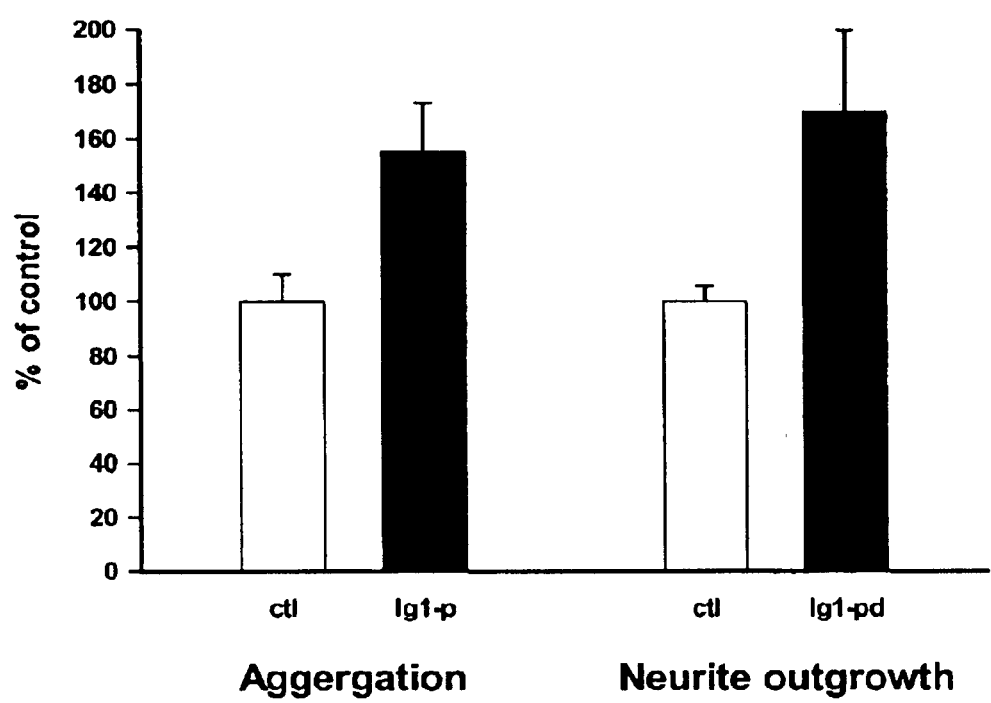
FIG. 24. Effect of Ig1-peptide (Ig1-p) on aggregation (left, 250 μg/ml) and neurite outgrowth (rigth, 5 μg/ml) from hippocampal neurons grown for 24 h. The number of aggregates and the length of neurites is expressed normalised relative to control cultures. Three individual experiments were performed. Results are given as mean ±SEM.
Figure 25:
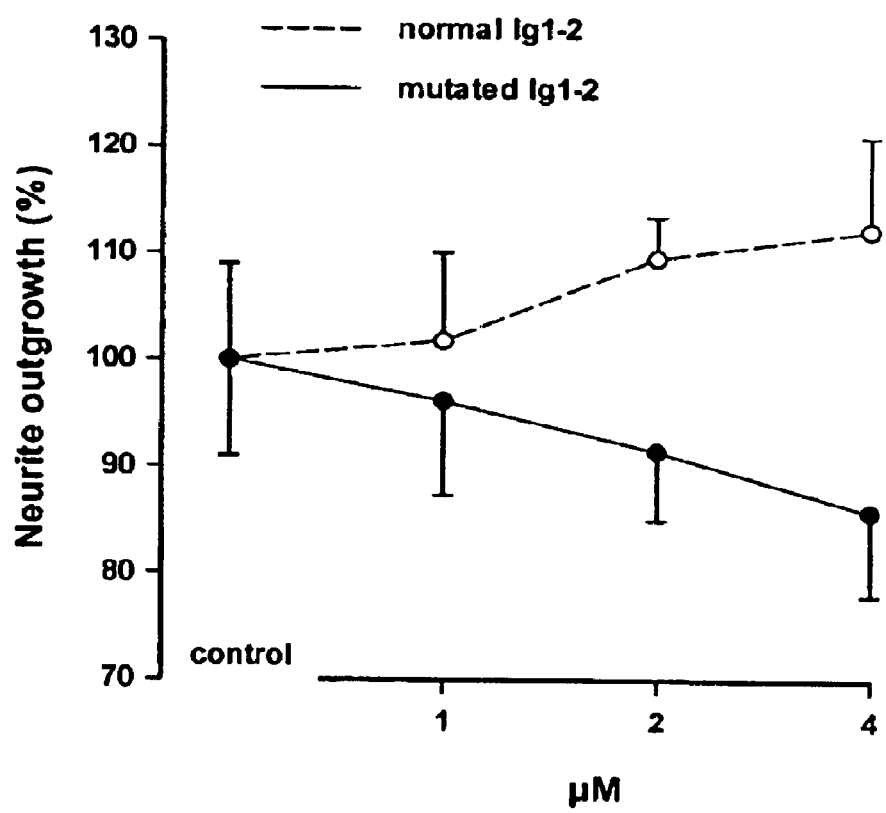
FIG. 25. Effect of mutations in a double Ig domain (Ig1–2) of NCAM on neurite outgrowth from hippocampal neurons. The following mutations were made in NCAM (20-208): R192A, R196A, and E198A. The length of neurites in treated cultures is expressed as a percentage of the length of neurites in control cultures. Five individual experiments were performed. Results are given as mean ±SEM.

The inventors have further disclosed a small synthetic peptide, called IG2-P and it is surprisingly shown, that this strongly stimulates neurite outgrowth (see FIGS. 20–21). By means of nuclear magnetic resonance (NMR) (see FIG. 18), the NCAM Ig2 domain was shown to belong to the I-set of Ig-domains (ref) as does the NCAM Ig1 domain that may be capable of binding to the NCAM Ig2 domain. By analysing the chemical shifts of the individual amino acid residues a distinct interaction site between the Ig1 and the Ig2 domain was surprisinly found. It was strikingly found that the total interaction site consisted of residues from both the Ig1 and the Ig2 domain of NCAM. Thus, parts of these two domains together formed one distinct interaction site. In the Ig2 domain, the amino acids Arg-192, Arg-196, Glu-198, Ile-199 and Phe-201 were particularly important for the binding according to the chemical shift studies and the indicated model. Similarly, in the Ig1 domain, the amino acids Glu-30, Glu-35 and Lys-37, Phe-38 and Phe-39 appeared to be particularly important for the binding (see FIG. 18).

Further investigations with mutations of the amino acids Arg-192, Arg-196, Glu-198, Glu-30, Glu-35 and Lys-37 showed that these mutations inhibited the binding function of the NCAM Ig2 domain. From investigation of the Ig2 and the Ig1 structure solved by NMR two peptides were then constructed by the inventors and two particular regions in the three dimensional structure of the entire domain were revealed as being of particular and surprising importance.

Thereafter, a presumingly corresponding sequence of 12 amino acids from the two-dimensional amino acid sequence of the entire Ig2 domain of NCAM (residues 191–202) (see FIG. 17) and a sequence of 12 amino acids from the Ig1 domain (residues 29–40) were identified. Two peptides corresponding to these short sequences were then synthesised and shown to promote neurite outgrowth from neurons in cell cultures and thereby to, posses a potential to promote regeneration and other forms of structural plasticity of cells and tissues expressing NCAM.

The identified Ig2-peptide, called IG2-P, was demonstrated to have the sequence GRILARGEINFK (SEQ ID NO:23) and thus shares no similarity to other neuritogenic peptides, either derived from the entire. NCAM-sequence or found to bind the NCAM-molecule. In addition, for control purposes, the invention provides 2 peptides sequences (SEQ ID NO:24 and SEQ ID NO:25), derived from the Ig2-p sequence, which peptides do not promote neurite outgrowth. The use of these polypeptides for control purposes are explained in more detail in example 5. The Ig1-peptide, called IG1-P, appeared to have the sequence GEIS-VGESKFFL (SEQ ID NO:26) sharing no homology to known neuritogenic factors. The four sequences found were GRILARGEINFK (SEQ ID NO:23)
GSILASGESNFK (SEQ ID NO:24)
GRILARGSSNFK (SEQ ID NO:25)
GEISVGESKFFL (SEQ ID NO:26)

The present invention provides thus compounds or compositions comprising the IG1-P-peptide and/or the IG2-P-peptide or derivatives hereof, such as peptide-analogues, peptide-fragments, polypeptides comprising the IG1-P-sequence or the IG2-P-sequence or analogues hereof and non-peptide molecules derived from the herein presented IG1-P-peptide and IG2-P-peptide, which are capable of stimulating neurite outgrowth from neurons, neuronal cell lines or tissues.

These mentioned compounds and compositions can be used to treat degenerative conditions affecting the peripheral or central nervous system, muscle and other tissues expressing NCAM as well as other conditions in which a stimulation of NCAM function is beneficial.

The present invention also includes an additional and surprising finding to the above disclosure, that the specific signal transduction pathways of neurite outgrowth appears to be stimulated by the NCAM Ig2 domain and fragments and mimics thereof furthermore the NCAM Ig1 domain and fragments and mimics thereof, and the small peptides comprising two or more basic amino acid residues. It was thus found that the specific signal transduction pathways were also stimulated by the Ig2-peptide, Ig2-p described above. Thus, the inventors have identified a homophilic binding site in NCAM to which the NCAM domains Ig1 and Ig2 contribute. Further it is demonstrated that four ligands binding to the binding site constituted by the NCAM Ig1–Ig2 domains, namely the NCAM Ig2 domain, the Ig2-p peptide derived from the NCAM Ig2 sequence, the Ig-1-p peptide derived from the NCAM Ig1 sequence and the C3 peptide and related peptides identified from a combinatorial peptide library, all promote neurite outgrowth. All four NCAM Ig1–Ig2 ligands belong to the same new class of compounds capable of binding the NCAM Ig1–Ig2 domains thereby activating signal transduction leading to neurite outgrowth.

In general, the present invention discloses novel compounds which are able to stimulate and promote the outgrowth of neurites from and/or NCAM presenting cells within the central and peripheral nervous system.

Furthermore, the novel compounds according to the invention appear to promote formation and plasticity og neural connections. As it appears from the above, it was revealed by the inventors, that the compounds of the invention belong to three disclosed groups of compounds (the compound groups I, II and III) and after the compound group I has been detailed, the compound group II will be described in the following.

The compound group, II contains compounds, which may be peptides which bind to that part of the homophilic binding site of NCAM Ig1–Ig2 which is constituted by the Ig1 domain. Such peptides appear to have the general sequence, including any functional derivative thereof, as follows

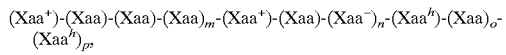

wherein Xaa$^+$ is a basic amino acid residue,

Xaa$^-$ is a an acidic amino acid residue,

Xaa$^h$ is a apolar amino acid residue,

Xaa is any amino acid residue, and m,n,o and p independently are 0 or 1, and wherein the basic amino acid residues preferably are lysine or arginine, the acidic amino acids preferably are glutamic acid or aspartic acid, the apolar amino acids are preferably leucine, isoleucine, valine or phenylalanine, and r preferably is 1.

A peptide according to group II comprises the sequence (K/R)-X-X-X-(K/R)-X-(E/D)-(L/I/V/F)-X-(L/I/V/F), wherein X is any amino acid residue, suitably the sequence (K/R)-X-(E/D)-(L/I/V/F)-X-(L/I/V/F), (K/R)-X-X-X-(K/R)-X-(E/D), (K/R)-X-X-(K/R)-X-(E/D) or (K/R)-X-(L/I/V/F)-X-(L/I/V/F), more suitably the sequences (K/R)-X-X-X-(K/R)-X-(E/D)-(L/I/V/F), (K/R)-X-X-(K/R)-X-(E/D)-(L/I/V/F) or (K/R)-X-X-X-(K/R)-X-(L/I/V/F), even more suitably the sequences (K/R)-X-X-(K/R)-X-(E/D)-(L/I/V/F)-X-(L/I/V/F), (K/R)-X-X-X-(K/R)-X-(L/I/V/F)-X-(L/I/V/F) or (K/R)-X-X-X-(K/R)-X-(E/D)-(L/I/V/F)-(L/I/V/F) and most suitably the sequence GRILARGEINFK (SEQ ID NO: 23).

Regarding the compound group III, the compounds of this group may likewise be a peptide that binds to the part of the homophilic bindingsite of NCAM Ig1–Ig2 that is constituted by the Ig2 domain. Such peptides appear to have the general sequence, including any functional derivative thereof, as follows

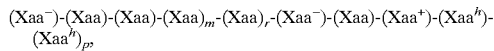

wherein Xaa$^+$ is a basic amino acid residue

Xaa$^-$ is a an acidic amino acid residue,

Xaa$^h$ is an apolar amino acid residue,

Xaa is any amino acid residue, and m,n,o and p independently are 0 or 1, and wherein the basic amino acid residues preferably are lysine or arginine, the acidic amino acids preferably are glutamic acid or aspartic acid, the apolar amino acids are preferably leucine, isoleucine, valine or phenylalanine, and r preferably is 1.

A peptide within group III comprises the sequence (E/D)-X-X-X-(E/D)-X-(K/R)-(L/I/V/F)-X-(L/I/V/F), wherein X is any amino acid residue, suitably the sequence (E/D)-X-(K/R)-(L/I/V/F)-X-(L/I/V/F), (E/D)-X-(K/R)-(L/I/V/F)-(L/I/V/F), (E/D)-X-X-X-(E/D)-X-(K/R)-(L/I/V/F), (E/D)-X-X-X-(E/D)-X-(K/R)-(L/I/V/F) or (E/D)-X-X-(E/D)-X-(K/R)-(L/I/V/F), more suitably E/D)-X-X-(E/D)-X-(K/R)-(L/I/V/F)-X-(L/I/V/F/) or (E/D)-X-X-(E/D)-X-(K/R)-(L/I/V/F,-(L/I/V/F), even more suitably the sequences (E/D)-X-X-X-X-(E/D)-X-(K/R)-(L/I/V/F)-(L/I/V/F), (E/D-X-X-X-(E/D)-X-(K/R)-(L/I/V/F)-X-(L/I/V/F) or (E/D)-X-X-X-(E/D)-X-(K/R)-(L/I/V/F)-(L/I/V/F), and most suitably the sequence GEJSVGESKFFL (SEQ ID NO: 26).

Compounds provided in the present invention also comprise peptides that bind to the NCAM Ig1 domain and stimulates neurite outgrowth.

The peptides may be modified, for example by substitution of one or more of the amino acid residues. Both L-amino acids and D-amino acids may be used. Other modification may comprise derivatives such as esters, sugars, etc. Examples are methyl and acetyl esters. Polymerisation such as repetitive sequences or attachment to various carriers well-known in the art, e.g. lysine backbones or protein moieties such as bovine serum albumin (BSA) is also an aspect of the invention.

The invention also concerns non-peptide mimics of the NCAM Ig2 domain or the peptides defined above. In the present context, such mimics should be understood to be compounds which bind to or in other ways interact with the NCAM Ig1 domain and/or the NCAM Ig2 domain and thereby stimulate neurite outgrowth from and/or proliferation of NCAM presenting cells.

In a further aspect, the present invention relates to compounds which are anti-NCAM Ig1 antibodies, or antibodies recognising the part of Ig2 contributing to the NCAM Ig1–Ig2 binding site disclosed herein.

The antibodies may be monoclonal or polyclonal. Recombinant antibodies such as chimeric and/or humanised antibodies are also a part of the invention.

In a further aspect, the present invention relates to the NCAM Ig2 polypeptide, a fragment or a mimic thereof for use in the treatment of a normal, degenerated or damaged NCAM presenting cells. The treatment is a treatment of diseases and conditions of the central and peripheral nervous system, of the muscles or of various organs. Only NCAM presenting cells may respond to such a treatment.

The invention also relates to a pharmaceutical composition and a medicament comprising one or more of the compounds defined above.

In yet a further aspect, the present invention relates to methods of treating normal, degenerated or damaged NCAM presenting cells in vitro or in vivo, the method involving administering an effective amount of one or more compounds as defined above.

The treatment comprises treatment of diseases or conditions of the central and peripheral nervous system, such as postoperative nerve damage, traumatic nerve damage, impaired myelination of nerve fibers, postischaemic, e.g. resulting from a stroke, Parkinsons disease, Alzheimers disease, dementias such as multiinfarct dementia, sclerosis, nerve degeneration associated with diabetes mellitus, disorders affecting the circadian clock or neuro-muscular transmission, and schizophrenia; of diseases and conditions of the muscles including conditions with impaired function of neuro-muscular connections, such as genetic or traumatic atrophic muscle disorders; and treatment of diseases and conditions of the organs, such as degenerative conditions of the gonads, of the pancreas such as diabetes mellitus type I and II, of the kidneys such as nephrosis and of the heart, liver and bowel.

Another aspect of the invention is the use of the compounds according to the invention in combination with a prosthetic nerve guide.

Yet another aspect of the invention is the use of the compounds according to the invention in the stimulation of the ability to learn and/or of the memory.

To be able to identify candidate ligands capable of stimulating NCAM function, the inventors have established a simple culture system (aggregate cultures) that permits a quantitative evaluation of the effect of various ligands. Hippocampal cells are provided from rat embryos. The cells are grown in a defined medium and dissociated cells are seeded in microtiter plates. After 24 h, the amount of aggregates are counted. Compounds to be tested are added to the cell suspension immediately before seeding of cells in the microwells. When NCAM Ig1 binding ligands are present during the aggregation of cells, smaller, but more numerous cell aggregates are seen when quantified 24 h after seeding of cells. The inhibiting effect of the ligands results in a blockage of the formation of large aggregates from many small aggregates as the adhesion properties of NCAM are blocked. Thus small, but more numerous cell aggregates are seen in the presence of active ligands.

Such an effect was observed when different ligands of the NCAM Ig1–Ig2 domain were present during the aggregation of cells. Thus, the entire recombinant Ig2 and a synthetic peptide derived from either the Ig2 sequence (Ig2-p) (SEQ ID NO:23) or the Ig1 sequence (Ig1-p) (SEQ ID NO:26) and peptide ligands of NCAM-Ig1 identified from libraries of synthetic peptides (SEQ ID NO:1, SEQ ID NO:2 and SEQ ID NO:3) inhibited aggregation in the described cell culture system.

The system allows the examination of cell adhesion, cell migration and formation of processes in the treated cells leading to possibly neurite outgrowth. To investigate the latter further, neurite extension from single neurones may be studied. Cells are prepared as in the aggregation study and seeded on a substrate of plastic or fibronectin. The cells are then maintained for a suitable time, whereafter the neurite outgrowth is analysed by a measurement of the neurite extension, for example by a computer-assisted image analysis program. The mean length of the longest neurite of each cell was measured for neurites longer than 10 $\mu$M(see FIG. 2). In addition, the mean number of branchpoints per neurite and the mean number of neurites per cell were determined. NCAM Ig1–Ig2 ligands to be tested are added immediately before seeding the cells. (SEQ ID NO: 1,2,3,23,26).

Similarly, peptides derived from the binding site in NCAM Ig1–Ig2 were added immediately before seeding the cells.

To investigate the mechanisms of the neuritogene effect, one of the ligands, C3 (SEQ ID NO:1) was added in combination with various compounds known to inhibit NCAM dependent signalling. The following compounds were found to inhibit the stimulatory effect of C3 on neurite extension: verapamil "ve" inhibitor of L-type voltage dependent calcium channels), omega-conotoxin GVIA ("co" inhibitor of N-type voltage dependent calcium channels), pertussis toxin ("pertus" inhibitor of certain G-proteins), an erbstatin analogue ("erb"; inhibitor of certain tyrosine kinases), antibody to an acidbox epitope in fibroblast growth factor receptors (FGF-Rs) (inhibitor of NCAM-FGF-R binding and signalling), a peptide corresponding to the so-called CAM homology domain (CHD) (inhibitor of NCAM-FGF-R binding and signalling).

In addition, the neuritogenic effect of C3 was completely abrogated by the NCAM Ig1 domain in solution. These results show that the ligands such as C3 stimulate neurite outgrowth by binding to the NCAM Ig1 domain and thereby activating signalling pathways in the neurone that are sensitive to the above mentioned inhibitor-compounds.

The endogenous ligand of NCAM Ig1, NCAM Ig2 was tested for its effect on neurite outgrowth from primary hippocampal neurones maintained on a substrate of fibronectin. NCAM Ig2 was added to the culture-wells immediately before seeding of cells. It is found that NCAM Ig2 stimulates neurite outgrowth similar to the C3 peptide. The maximal neuritogenic effect of NCAM Ig2 was found at the same concentration at which the C3 peptide had its maximal neuritogenic effect.

When the NCAM Ig2 domain was tested in combination with compounds known to inhibit NCAM dependent signalling as described for C3 above, the neuritogenic effect was inhibited in the same way. It thus appears that the endogenous ligand NCAM Ig2 and the artificial ligand C3 both bind to NCAM Ig1 and that both NCAM Ig2 and C3 stimulate neurite extension, which is believed to be due to activation of identical signal-transduction pathways.

When synthetic peptides derived from the binding site of NCAM Ig1 or NCAM Ig2 were added to the cell cultures, neurite outgrowth was stimulated. Thus, the effect of Ig2 can be mimicked by small synthetic peptides constituting fragments of the NCAM Ig1–Ig2 sequence. Hence, neurite outgrowth appeared to be promoted firstly by the intact Ig2 domain in its form of a recombinant polypeptide, secondly by fragments of the NCAM-Ig1 and NCAM-Ig2 domain and thirdly by NCAM-Ig1 binding peptides that were unrelated to the peptides derivable from the sequence. Therefore the inventors have demonstrated the novel and surprising principle that neurite outgrowth is promotable by compounds that bind to the NCAM Ig1 domain and/or to parts of the NCAM Ig1–Ig2, which are being involved in homophilic NCAM binding.

In order to control the specificity of the Ig2-peptide (Ig2-p), two control peptides, P2-3S and P2-4S, were synthesised and found to have no neuritogenic effect. Reference is made to example 5). The sequence of the P2-3s peptide, GSILASGESNFK (SEQ ID: 24) corresponds to the sequence of Ig2-p, in which Arg-2, Arg-6 and Ile-9 are substituted with serines. The sequence of P2-4S peptide, GSILASGSSNFK (SEQ ID NO: 25) corresponds to the sequence of Ig2-p, in which Arg-2, Arg-6, Glu-8 and Ile-9 are substituted with serines showing that the mutated amino acid residues are important for the neuritogenic effect of the Ig2-p peptide.

NCAM Ig2 and C3 were also tested for their effect on neurite outgrowth when added in combination. The effects were found to be non-additive. The results further indicate that NCAM Ig2 and C3 stimulate neurite extension by identical mechanisms. They both bind to the NCAM Ig1 domain and thereby activate identical signalling pathways leading to neurite outgrowth.

Putative artificial ligands may be selected and identified from peptide or non-peptide libraries. Any peptide library may be used. Synthetic peptide libraries as well as libraries containing fragmented natural occurring proteins, may be used in the search for useful peptides. Any kind of libraries comprising non-peptide compounds may similarly be used.

Peptides are short molecules consisting of amino acids in a linear sequence. Amino acids are the building blocks of naturally occurring proteins which consist of long folded chains of amino acids. Thus, peptides characterised by a certain sequence of amino acids may mimic a certain area of a protein. Naturally occurring proteins consist of L-amino acid residues. However, artificial peptides may also consist of or comprise D-amino acid residues. By combinatorial chemistry, mixtures of beads carrying peptides of equal length can be constructed, in which each bead carries peptides of a unique sequence (Lam et al., 1991). Such a mixture of peptides on beads is called a peptide library.

In the present invention, peptides were identified by screening synthetic random peptide, libraries comprising resin-bound decapeptides with purified recombinant NCAM Ig1. The synthesis of the resin-bound one-bead one-peptide library was performed using the portioning, mix procedure (Furka, À., Sebestyyén, F., Asgedom, M. And Dibó, G. (1991) Int. J. Pep. Prot. Res. 37, 487–493). Polyethylene syringes served as reaction vessels throughout the synthesis. Screenings were done by incubating the resin with biotinylated NCAM Ig1. Subsequently the resin was incubated with avidin-alkaline phosphatase. The substrates BCIP/NBT (Sigma) were added as described by the procedure by Lam et al. (1992) and stained beads removed for micro sequencing.

The most intensely stained beads were selected under stereo microscope and sequenced on an. ABI 470A equipped with an ABI 120A HPLC. 22 NCAM Ig1 binding peptide sequences were identified (FIG. 4(A); SEQ ID NO:1 to SEQ ID NO:22).

It is to be understood that the method chosen for identification and selection of interesting peptides is not critical for the identification of a putative motif.

Peptide sequences to be synthesised were chosen by aligning the obtained sequences and examining these for repeated patterns revealing putative motifs (FIGS. 4(B)–(D)).

The three peptides called C3, D3 and D4 (FIGS. 4(B)–(D)) were synthesised and their binding to the NCAM Ig1 domain evaluated by plasmon surface resonance analysis. When immobilised on a sensor chip, peptide dendrimers (4 peptides linked to a lysine backbone (FIG. 2(C)) were used in order to secure an exposure of at least one peptide for binding to NCAM Ig1 in solution. All three peptides bound the NCAM-Ig1 in solution. The three peptides were further tested for their effect on neurite outgrowth. All three peptides strongly stimulated neurite outgrowth. Moreover, the peptides inhibited aggregation of cells.

To investigate which properties of the peptides are important for the effect, various control-peptides of the C3-sequence were constructed and tested.

To investigate the role of the individual residues in the C3-sequence, so-called scrambled peptides, comprising the same residues as C3 but in a different sequence, were constructed (121, 114 and C3scr in FIG. 7). Similarly, scrambled peptides corresponding to the residues in the D3 and D4 sequences were constructed (scrambled D3 and scrambled D4 in FIG. 7). Furthermore, peptides containing the C3-sequence in which basic amino acids (Ks and Rs) were substituted with alanines were constructed (116–119 in FIG. 7) to explore the role of these particular amino acids. Likewise, a peptide corresponding to the C3-sequence in which the proline-residue (Xaa$^1$) was substituted with an alanine was constructed, as prolines are generally considered important for the structure of peptides. Substituting the proline with an alanine does not change the effect. Likewise, one basic amino acid could be alanine substituted without a change in effect. In contrast, peptides with two to four alanine substitutions of the basic residues had no effect on aggregation indicating that these residues are important for the effect of C3. To further investigate the role of the basic amino acid residues in C3, a peptide containing the C3-sequence in which the basic amino acids were modified by acetylation was constructed. The acetylation removes the charges from these residues while preserving the ability to form hydrogen bonds. A peptide in which four basic amino acids were modified by acetylation (C3dacetyl. K(120) in FIG. 7) inhibited aggregation as C3 indicating that not only the charges but also other properties of the basic amino acids such as the ability to form hydrogen bonds must be important for the effect of C3. Similar aggregate cultures were prepared in the presence of C3 as monomer, dendrimer (C3d) or as BSA-coupled 20-mer. Different forms of the C3 peptide were tested. It was found that monomeric, dendrimeric and BSA-coupled forms of C3 have similar effects on aggregation. The dendrimer of the C3 sequence is the most potent form, presumably due to the ability to link several of the receptor domains. To verity that the receptor is in fact the NCAM Ig1 domain, the cells were incubated with this domain prepared in *Pichia pastoris* in solution as described in Example 1. The presence of the NCAM Ig1 domain abrogated the effect of C3 demonstrating an interference with NCAM-mediated cell adhesion of C3. These experiments show that the here identified NCAM Ig1 binding peptides influence NCAM mediated cell adhesion and thereby increase the number of cell aggregates and neuronal processes formed in cultures of primary neurones grown at high densities.

The substitution of only two basic, amino acids in the sequence of the C3 peptide completely abolished the neuritogenic effect. Thus, when two to four lysines and arginines in the sequence were substituted by alanines, the neurite stimulatory effect was completely abrogated. This shows that the basic amino acids in the C3 sequence are crucial for its effect. Surprisingly, peptides in which the same amino acids were modified by acetylation have some effect on cell adhesion and neurite outgrowth, although not to the same extent as the intact C3 peptide, showing that not only the charges but also other properties of the basic amino acids, such as the ability to form hydrogen bonds, are of importance. In addition, the effect of the intact peptide can be blocked by equimolar concentrations of the NCAM Ig1 domain in solution. This shows that the peptide works by binding to the NCAM Ig1 domain expressed by neurones.

The effect of the ligands on proliferation and cell growth was also tested. The C3 peptide was found to initially stimulate proliferation and cell growth. After this initial promotion of proliferation, the peptides stimulate differentiation by increasing neurite outgrowth and at the same time suppressing proliferation. Thus the net effect on proliferation depends on the growth status of the cells. An effect on proliferation has been shown for primary cell cultures from the hippocampus cells and cultures of rat pheochromocytoma cell line PC12 cells. Accordingly, the ligands stimulate neurite outgrowth from and/or proliferation of NCAM presenting cells.

As it clearly has been described discloses this invention three groups, group I,II and III, of compounds, and a compound of the group I of the invention may be a peptide, which binds to the NCAM Ig1 domain through a binding motif which comprises at least 2 basic amino acid residues. Peptides comprising at least 2 basic amino acid residues within a sequence of 10 amino acid residues, suitably within a sequence of 3 amino acid residues, are believed to be very interesting compounds for the purpose of the present invention.

The analysis of the isolated peptide ligands revealed that the ligands may advantageously comprise more than two basic amino acids.

In accordance herewith, interesting peptides within group I comprise the sequence

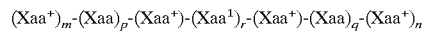

wherein

Xaa$^+$ is a basic amino acid residue,

Xaa$^1$ is any amino acid residue,

Xaa is any amino acid residue, and m,n,p,q and r independently are 0 or 1.

The basic amino acid residues are preferably selected from lysine (K) and arginine (R) and r is preferably 1.

The nature of the amino acid residues Xaa and Xaa$^1$ does not seem to be important. It appears that they may be any amino acid residue. However, Xaa¹ is preferably proline P) or glutamic acid (E).

In even more preferred peptides r is 1 and at least one of m and n is 1.

Preferred peptides of the invention comprise the sequence $(K/R)_{0-1}$-K/R-X-K/R), wherein X has the meaning Xaa¹, suitably the sequence K/R-K/R-X-K/R or K/R-X-K/R, more suitably the sequence K/R-P-K/R, K/R-K/R-P-K/R, K/R-K/R-E-K/R or K/R-K/R-E-K/R, even more suitable K-P-K, K-K-P-K, K-K-E-K or K-K-E-R and most suitable the sequences A-S-K-K-P-K-R-N-I-K-A (SEQ ID NO:1), A-K-K-E-R-Q-R-K-D-T-Q (SEQ ID NO:2), or A-R-A-L-N-W-G-A-K-P-K (SEQ ID NO:3).

It may be speculated that the reason why the distance between the basic amino acid residues is a variable factor in the deduced motif, is that one of the important properties of the ligand may be the exposure of a cluster of basic amino acid residues, i.e. an epitope comprising basic amino acids residues. Such a cluster may be created by a sequence of closely linked basic amino acids or alternatively through peptide/protein folding. Advantageously, the basic amino acid residues may be exposed on the surface of a carrier. Particularly, multimeric peptides such as dendrimers may form conformational determinants or clusters due to the presence of multiple flexible peptide monomers.

As discussed above, the analysis of the active peptides isolated from the peptide library suggests that the motif may comprise more than two positively charged amino acids, for example three or four basic amino acids. The strength of the binding and of the resulting downstream signal probably depend upon the number and/or the position of the basic amino acids in the peptide, resulting in clusters of variable functional strength. The position of other amino acids in the peptide may be of importance, especially in the case of peptide folding. The variable strength of the cluster may result in variable binding constants and thus in variable strength in signalling.

Without wishing to be bound by a certain theory, the inventors believe that active ligands to the NCAM Ig1 and/or the NCAM Ig2 domain are ligands which bind to the NCAM Ig1 domain and/or the NCAM Ig2 domain thus trigger a conformational change of the domain resulting in a signalling cascade being initiated, which signalling influences proliferation of cells and/or neurite outgrowth. Thus, a suitable ligand may be any compound which can trigger a conformational change of the NCAM Ig1domain and the NCAM Ig2 domain, resulting in a downstream signalling.

Very interesting peptides are those which correspond to a part of the NCAM Ig2 domain, are a mimic or fragment of the NCAM Ig2 domain. The peptides may bind to the Ig2 binding site on the NCAM Ig2 domain or to a binding site different from the NCAM Ig2 binding site. It is believed that the ligands C3, D3 and D4 bind to a site different from the binding site of NCAM Ig2 or fragments thereof.

Of likewise particular interest in addition to ligands of the Ig1 domain, are ligands of the Ig2 domain including the ligands of that part of the Ig1–Ig2 binding site which is constituted by the Ig2 domain.

Other compounds which are interesting compounds for the purposes of the present invention are non-peptide molecules mimicking the binding of the NCAM Ig1, the NCAM Ig2 domain or the artificial ligands. Such other compounds may be selected from small organic compounds, sugars and lipids, as well as peptidomimetics, peptoides and peptomers.

Libraries of small organic compounds may be screened to identify artificial ligands of the NCAM Ig1 domain, the NCAM Ig2 domain and artificial ligands of the Ig1–Ig2 binding site, that is constituted by the NCAM Ig1 and Ig2 domains, which ligands may stimulate NCAM activity. Such libraries or their construction are commonly known and the screening for useful ligands may follow the methods for screening disclosed in this paper, or in ways obvious to the skilled person.

Such other compound may also be an anti-NCAM Ig1 antibody, an anti-NCAM Ig2 antibody (monoclonal, polyclonal or recombinant) or another antibody recognising epitopes in or near the binding site, that is constituted by the NCAM Ig1 and Ig2 domains, which antibody further may be chimeric or humanised. The production of polyclonal as well as a) monoclonal anti-NCAM Ig1 antibodies and/or b) anti-NCAM Ig2 antibodies may follow common known procedures. Mice or rabbits may serve as the primary immunisation forum, in which antibodies to NCAM Ig1 or antibodies to NCAM Ig2 are raised. Purified polyclonal antibodies may be used without any further treatment. Alternatively, monoclonal antibodies may be produced. Methods of producing monoclonal antibodies are common in the art. Recombinant antibodies such as chimeric and humanised antibodies may also be obtained by methods common in the art. Possible active antibodies are then screened according to the methods disclosed above or in similar ways.

Substances with the potential to promote neurite outgrowth as well as survival and proliferation of neuronal cells such as certain endogenous trophic factors are prime targets in the search for compounds that facilitate neuronal regeneration and other forms of neuronal plasticity (Fu and Gordon, 1997). Peripheral nerves possess a potential to regenerate and re-establish functional connections with their targets after various injuries. However, functional recovery is rarely complete and peripheral nerve damage remains a considerable problem. In the central nervous system, the potential for regeneration is very limited. Therefore, the identification of substances with the ability to promote functional regeneration in the peripheral and the central nervous system is of great interest. To evaluate the potential of a substance to promote regeneration, the ability to stimulate neurite outgrowth and proliferation and survival of neuronal cells may be investigated. The NCAM Ig1 or NCAM Ig2 binding compounds of the present invention are shown to promote neurite outgrowth and to affect neuronal proliferation and are therefore most likely good promoters of regeneration of neuronal connections and thereby of functional recovery after damages as well as promoters of neuronal function in other conditions where such an effect is required.

Accordingly, the present invention relates to the NCAM Ig1 domain, the NCAM Ig2 domain and a fragment or a mimic thereof for use in the treatment of a normal, degenerated or damaged NCAM presenting cell. An example of a fragment of the Ig1 domain is the part of the NCAM Ig1 domain which is involved in the NCAM Ig1–Ig2 binding site. In particular, the invention relates to the NCAM Ig2 domain, a fragment or a mimic thereof for use in the treatment of normal, degenerated or damaged NCAM presenting cells, which treatment consists of stimulating outgrowth from and/or proliferation of the NCAM presenting cells.

The treatment may suitably be a treatment of diseases and conditions of the central and peripheral nervous system, of the muscles or of various organs such as treatment of diseases or conditions of the central and peripheral nervous system, such as postoperative nerve damage, traumatic nerve damage, impair myelination of nerve fibres, postischaemic, e.g. resulting from a stroke, Parkinson's disease, Alzheimer's disease, dementias such as multiinfarct dementia, sclerosis, nerve degeneration associated with diabetes mellitus, disorders affecting the circadian clock or neuro-muscular transmission, and schizophrenia, treatment of diseases of muscles including conditions with impaired function of neuro-muscular connections such as genetic or traumatic atrophic muscle disorders, a treatment of diseases of various organs, such as degenerative conditions of the gonads, of the pancreas such as diabetes mellitus type I and II, of the kidney such as nephrosis and of the heart, liver and bowel and treatment or stimulation of the ability to learn and/or of the memory.

The present invention also relates to the use of the NCAM Ig1–Ig2 domain and/or the use of that part of the NCAM Ig1 that is involved in the NCAM Ig1–Ig2 binding site, or a fragment of mimic thereof in the manufacture of a medicament for the treatment of normal, degenerated or damaged NCAM presenting cells. Thus, the present invention relates to the use of the NCAM Ig2 domain, or a fragment of mimic thereof in the manufacture of a medicament for the treatment of NCAM presenting cells, so as to provide a stimulation of neurite outgrowth from and/or proliferation of NCAM presenting cells.

In particular, the use of the NCAM Ig2 domain, or a fragment or mimic thereof in the manufacture of a medicament for the treatment of NCAM presenting cells, wherein the medicament is for treatment of diseases or conditions of the central and peripheral nervous system, such as postoperative nerve damage, traumatic nerve damage, impaired myelination of nerve fibres, postischaemic, e.g. resulting from a stroke, Parkinson's disease, Alzheimer's disease, dementias such as multiinfarct dementia, sclerosis, nerve degeneration associated with diabetes mellitus, disorders affecting the circadian clock or neuro-muscular transmission, and schizophrenia; for treatment of diseases or conditions of the muscles including conditions with impaired function of neuro-muscular connections, such as genetic or traumatic atrophic muscle disorders; or for treatment of diseases or conditions of various organs, such as degenerative conditions of the gonads, of the pancreas such as diabetes mellitus type I and II, of the kidney such as nephrosis and of the heart, or is for the stimulation of the ability to learn and/or of the memory.

The invention also relates to a pharmaceutical composition comprising one or more of the compounds as defined above. In particular, the composition of the invention may comprise a compound being the NCAM. Ig2 polypeptide, a fragment or a peptide mimic thereof. In a preferred embodiment, the peptides are formulated as is multimers, e.g. bound to carriers. The peptides may suitably be formulated as dendrimers—such as four peptides linked to a lysine backbone, or coupled to a polymer carrier, for example a protein carrier, such as BSA. Such formulations are well-known to the person skilled in the art.

The invention also concerns a method of treating normal, degenerated or damaged NCAM presenting cells in vitro or in vivo, which method involves administering, in vitro or in viva, an effective amount of one or more of the compounds described above or a composition as described above, so as to provide a stimulation of neurite outgrowth from and/or proliferation of NCAM presenting cells.

In the method of the present invention, the treatment is preferably an in vivo treatment of diseases or conditions of the central and peripheral nervous system, such as postoperative nerve damage, traumatic nerve damage, impaired myelination of nerve fibres, postischaemic, e.g. resulting from a stroke, Parkinson's disease, Alzheimer's disease, dementias such as multiinfarct dementia, sclerosis, nerve degeneration associated with diabetes mellitus, disorders affecting the circadian clock or neuro-muscular transmission, and schizophrenia; of diseases or conditions of the muscles including conditions with impaired function of neuro-muscular connections, such as genetic or traumatic atrophic muscle disorders; or of diseases or conditions of the organs, such as degenerative conditions of the gonads, of the pancreas such as diabetes mellitus type I and II, of the kidney such as nephrosis and of the heart to the central or peripheral nervous system of a patient in need of treatment, and the method is characterised in that an effective amount of one or more of the compounds or a composition as defined above is administered to said patient.

Furthermore, the method of the invention may also be such, wherein the treatment leads to regeneration of nerves. The compounds are in particular used in combination with a prosthetic device such as a prosthetic nerve guide. Thus, in a further aspect, the present invention relates to a prosthetic nerve guide, characterised in that it comprises one or more of the compounds or the composition defined above. Nerve guides are known in the art.

In a further aspect, the invention relates to a method of stimulating the ability to learn and/or the memory in a subject, which method involves administering to a subject in need thereof an effective amount of one or more of the compounds as defined above or a composition as defined above.

The invention further concerns a medicament for the treatment of diseases and conditions of the central and peripheral nervous system, of the muscles or of various organs, which medicament comprises an effective amount of one or more of the compounds as defined above or a composition as defined above in combination with pharmaceutically acceptable additives. Such method may suitably be formulated for oral, percutaneous, intramuscular, intracranial, inrranasal or pulmonal administration.

In yet another embodiment, the present invention relates to a composition for use in the stimulation of learning and/or memory in a subject, which the composition comprises an effective amount of one or more of the compounds defined above or a composition as defined above in combination with one or more pharmaceutically acceptable additives. Such composition may suitably be formulated for oral, percutaneous, intramuscular, intracranial, intranasal or pulmonal administration.

Figure 8:
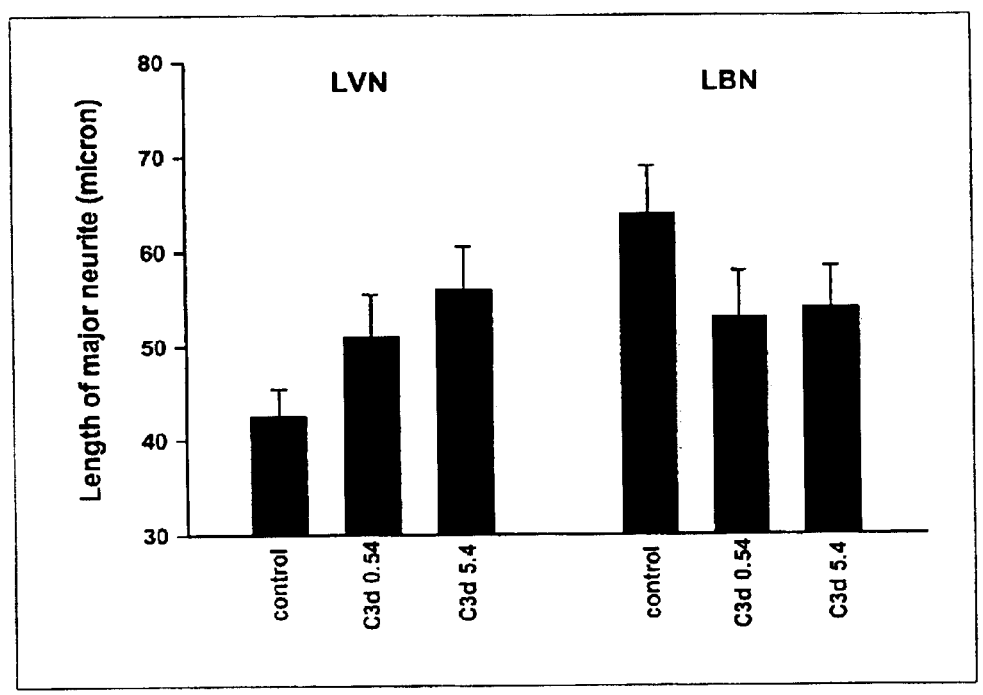
FIG. 8 shows the effect of C3 dendrimer on neurite outgrowth in cocultures of neurones and fibroblasts (Example 7). Primary hippocampal neurones were grown on monolayers of fibroblasts with (LBN) or without (LVN) NCAM-140 expression. Neurite-outgrowth was increased on LBN fibroblast-monolayers compared to LVN fibroblast monolayers. This increase was inhibited by C3d in 0.54 or 5.4 $\mu$M. On LVN monolayers, C3d stimulated neurite outgrowth.
Figure 13:
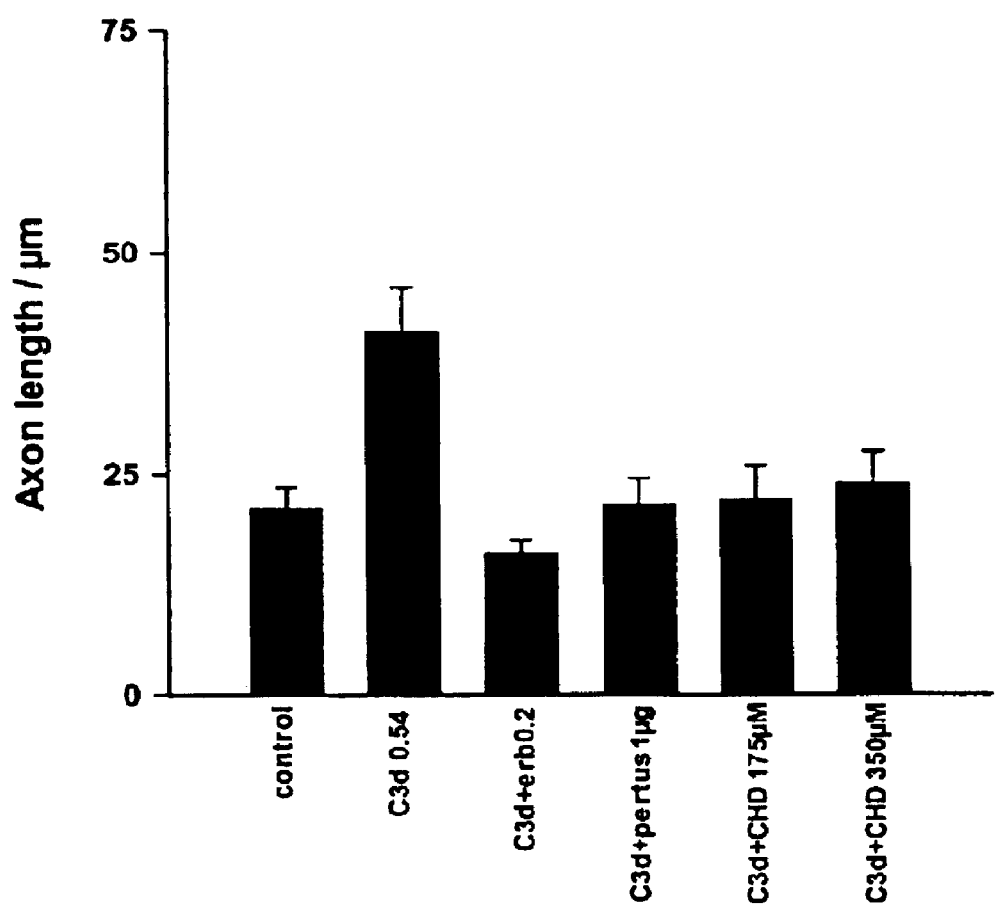
FIG. 13 shows the effect of various inhibitors of signal transduction on neurite outgrowth from primary hippocampal neurones maintained on fibronectin stimulated by C3d (0.54 $\mu$M, see Example 7). Erb: erbstatin analogue (0.2 $\mu$M), Pertus: Pertussis toxin (1 $\mu$g/ml), CHD: peptide corresponding to CAM homology domain in FGF-R (175 or 350 $\mu$M).

As appears from the above, increased plasticity is believed to be beneficial in the nervous system such as learning and regeneration and in other conditions outside the nervous system involving degenerative NCAM function. The effect of peptides of the present invention were investigated with respect to regeneration, i.e. axonal outgrowth from isolated superior cervical ganglia. It was found that peptide of the above-identified motif stimulated outgrowth as compared to a control peptide. It seems as if the observed effect is largely influenced by the dose administered, which presumably is due to the activating of signal transduction pathways by the NCAM Ig1 binding compounds resulting in a bell-shaped dose-response curve for neurite outgrowth (FIGS. 8 and 13). Thus a similar bell-shaped dose-response curve will be expected for the effect of NCAM Ig1 binding compounds on neuronal regeneration and other forms of plasticity dependent on activation of NCAM-mediated signal transduction pathways. The effect of NCAM Ig1 binding compounds on learning could be investigated in vivo by intraventricular infusion of the compounds in rodents or other animals followed by examination of the learning abilities of the animals after injections of various doses of NCAM Ig1 binding compounds. Injections should be performed before or at various time points after training as an inhibitory effect of NCAM-antibodies on certain forms of learning has been demonstrated when such injections were performed 5 to 8 hours following training (Scholey et al 1993). Useful learning models for evaluation of the effect of NCAM IG1 binding compounds on learning include passive avoidance and water maze learning in rodents or chicken. The effect of NCAM Ig1 binding compounds on synaptic plasticity associated with learning could be investigated in vitro or in vivo by measuring the induction or maintenance of long-term potentiation after application of NCAM Ig1 binding compounds, as has been done for NCAM-antibodies (Rønn et al 1995).

Surprisingly, it was found that the NCAM Ig2 domain and NCAM Ig1-binding peptide ligands displaying the characteristics of a motif as indicated above stimulate NCAM mediated signalling. In particular, the C3 peptide, Ig1-p and the Ig2-peptide, Ig2-p, stimulate NCAM functions including neurite extension by interacting with the NCAM Ig1 domain, thereby inducing signal transduction.

Accordingly, the compounds of the present invention are believed to have a beneficial effect in conditions, where which NCAM functions have been shown to be of importance.

As mentioned above, NCAM has been found to be expressed in several tissues and organs. Thus, interference with NCAM transmembrane signalling may have a beneficial influence in diseases and disorders such as 1) Diseases and conditions of the central and peripheral nervous system, in which increased potential for regeneration and synaptic plasticity is desirable such as postoperative nerve-damage; traumatic nerve damage; disorders characterised by impaired myelination of fibers; postischaemic damage, e.g. resulting from a stroke; Parkinsons disease; Alzheimers disease; other dementias including multiinfarct dementia; Sclerosis; nerve degeneration associated with diabetes mellitus; disorders affecting the circadian clock; disorders affecting neuro-muscular transmission; and Schizophrenia;

2) Diseases of the muscles including conditions with impaired function of neuro-muscular connections such as genetic atrophic muscle disorders; and traumatic atrophic muscle disorders;

3) Degenerative conditions of various organs such as degenerative conditions of the gonads; degenerative conditions of the pancreas including disorders involving β-cells; diabetes mellitus type I and II; degenerative conditions of the kidneys such as nephrosis; and degenerative conditions of the heart, liver and bowel.

As mentioned above, the present invention also relates to medicaments and compositions. Strategies in formulation development of medicaments and compositions based on the compounds of the present invention generally correspond to formulation strategies for any other protein-based drug product. Potential problems and the guidance required to overcome these problems are dealt with in several textbooks, e.g. "Therapeutic Peptides and Protein Formulation. Processing and Delivery Systems", Ed. A. K. Banga, Technomic Publishing A G, Basel, 1995.

Injectables are usually prepared either as liquid solutions or suspensions, solid forms suitable for solution in, or suspension in, liquid prior to injection. The preparation may also be emulsified. The active ingredient is often mixed with excipients which are pharmaceutically acceptable and compatible with the active ingredient. Suitable excipients are, for example, water, saline, dextrose, glycerol, ethanol or the like, and combinations thereof. In addition, if desired, the preparation may contain minor amounts of auxiliary substances such as wetting or emulsifying agents, pH buffering agents, or which enhance the effectiveness or transportation of the preparation.

Formulations of the compounds of the invention can be prepared by techniques known co the person skilled in the art. The formulations may contain pharmaceutically acceptable carriers and excipients including micropheres, liposomes, microcapsules, nanoparticles or the like.

The preparation may suitably be administered by injection, optionally at the site, where the active ingredient is to exert its effect. Additional formulations which are suitable for other modes of administration include suppositories, nasal, pulmonal and, in some cases, oral formulations. For suppositories, traditional binders and carriers include polyalkylene glycols or triglycerides. Such suppositories may be formed from mixtures containing the active ingredient(s) in the range of from 0.5% to 10%, preferably 1–2%. Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and generally contain 10–95% of the active ingredient(s), preferably 25–70%.

Other formulations are such suitable for nasal and pulmonal administration, e.g. inhalators and aerosols.

The active compound may be formulated as neutral or salt forms. Pharmaceutically acceptable salts include acid addition salts (formed with the free amino groups of the peptide compound) and which are formed with inorganic acids such as, for example, hydrochloric or phosphoric acids, or such organic acids as acetic acid, oxalic acid, tartaric acid, mandelic acid, and the like. Salts formed with the free carboxyl group may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The preparations are administered in a manner compatible with the dosage formulation, and in such amount as will be therapeutically effective. The quantity to be administered depends on the subject to be treated, including, e.g. the weight and age of the subject, the disease to be treated and the stage of disease. Suitable dosage ranges are of the order of several hundred $\mu$g active ingredient per administration with a preferred range of from about 0.1 $\mu$g to 1000 g, such as in the range of from about 1 $\mu$g to 300 $\mu$g, and especially in the range of from about 10 $\mu$g to 50 $\mu$g. Administration may be performed once or may be followed by subsequently administrations. The dosage with also depend on the route of administration and will vary with the age and weight of the subject to be treated.

Some of the compounds of the present invention are sufficiently active, but for some of the others, the effect will be enhanced if the preparation further comprises pharmaceutically acceptable additives and/or carriers. Such additives and carriers will be known in the art. In some cases, it will be advantageous to include a compound, which promote delivery of the active substance to its target.

In many instances, it will be necessary to administrate the formulation multiple times. Administration may be a continuous infusion, such as intraventricular infusion or administration in more doses such as more times a day, daily, more times a week, weekly, etc. It connection with the use in nerve guides, the administration may be continuous or in small portions based upon controlled release of the active compound(s). Furthermore, precursors may be used to control the rate of release and/or site of release. Other kinds of implants and well as oral administration may similarly be based upon controlled release and/or the use of precursors.

The treatment needs not be a treatment of an diagnosed disease, but may alternatively be a prophylactic treatment of subjects in general or of subjects known to have a high risk of getting one of the disease discussed above.

The invention is further illustrated by the non-limiting examples.

EXAMPLES

Example 1
Preparation of the Receptor Ig Domain 1 of NCAM

The Ig1 domain of NCAM was produced as a recombinant protein in Pichia pastoris. The cDNA fragment encoding amino acids 1–97 of rat NCAM was synthesised by PCR and amplified cDNA was subcloned into an XhoI/BamHI site of the pHIL-S1 plasmid (Invitrogen Corporation, San Diego, USA). An E. coli strain Top 10 F' (Invitrogen Corporation, San Diego, USA) was used for transformation. The recombinant plasmid was linearised with NsiI and used for transformation of Pichia pastoris strain His 4 GS-115 (Invitrogen Corporation, San Diego, USA). Transformation and selection was performed according to a Pichia Expression Kit manual supplied by the manufacturer. The recombinant protein was designated as Ig1 PP (Ig-like domain I produced in P. pastoris). The authenticity of Ig1 PP was secured by amino acid sequencing and MALDI-MS confirming the expected molecular weight of 11 kD. Cells were grown essentially according to the Pichia Expression Kit manual. After induction supernatant from growing cells was filtered through a 0.21 mm filter, concentrated by ultrafiltration and purified by gel filtration using a Sephadex G-50 column (Pharmacia Biotech AB, Sweden).

Example 2
Preparation of the Ig Domain 2 of NCAM

The cDNA encoding the Ig2 domain of NCAM was synthesised by PCR corresponding to residues 100 to 191. Rat NCAM-120 cDNA was used as template. The amplified cDNA fragment was subcloned into a SnaBI/AvrII site of the pPIC9K plasmid (Invitrogen). The recombinant plasmid was linearised with SacI and used for transformation of Pichia pastoris strain His 4 GS-115 (Invitrogen) according to the protocol supplied by the manufacturer. The recombinant Ig2 domain of NCAM was expressed after induction in a 2 liter fermentor (MER Mini Bioreactor, MBR Bioreactor AG). Thereafter, the expression medium was concentrated 10 times by ultra-filtration. The Ig2 domain was purified by gel-filtration by means of Sephadex G25 (Pharmacia) followed by ion exchange chromatography using a 5 ml HiTrap SP column (Pharmacia) yielding 10–15 mg per liter of expression medium. The authenticity of the NCAM Ig2 domain was confirmed by amino acid sequencing and mass spectroscopy. In the N-terminal, the original residues Lys-1 and Leu-2 were replaced with Tyr-1 and Val-2 due to cloning site considerations.

The disclosed model of dimerization of the first two domains of NCAM was experimentally demonstrated by the use of a group mutation approach as follows.

The following three mutations were made and the mutated NCAM (20-208) domains were produced as recombinant proteins: NCAM (20-208) with three mutations in the domain-1 E30A, E35A, K37A, NCAM (20-208) with three mutations in the domain-2 R192A, R196A, E198A and NCAM (20-208) with three mutations in the domain-1 E30A, E35A, K37A and three mutations in the domain-2 R192A, R196A,E198A. Mutations in the two sites of interest were introduced by PCR using 75 bp long 5' and 72 bp long 3' primers containing the mutations (5' CTG CAG GTA GAT ATT GTT CCC AGC CAA GGA GCC ATC AGC GTT GGA GCC TCC GCC TTC TTC CTG TGT CAA GTG GCA 3' (SEQ ID NO: 49) and 5' ATT CAC AAT GAC CTG AAT GTC CTT GAA GTT GAT GGC CCC GGC GGC CAG GAT GGC GCC CTC ACA GCG GTA AGT 3' (SEQ ID NO: 50)).

Three mutants of NCAM (20-208) were produced. In the first mutant residues Glu-30, Glu-35 and Lys-37 from the homophilic binding site of domain-1 were substituted with Ala. In the second mutant residues Arg-192, Arg-196 and Glu-198 from the homophilic binding site of domain 2 were substituted with Ala. The third mutant had 6 residues Glu-30, Glu-35, Lys-37, Arg-192, Arg-196 and Glu-198 substituted with Ala.

Following the confirmation of the presence of mutations by restriction analysis and DNA sequencing, it was verified that there were no significant variations in expression levels or in purification patterns for the mutants in comparison with the unmutated NCAM(20-208). By the use of gel filtration chromatography it was revealed that NCAM(20-208) elutes as a dimer at ~46 kDa, which finding provides for offering an easy and reliable way of monitoring the effects caused by mutations in the homophilic binding site when compared to the finding that the mutated proteins appeared to elute as a monomer at ~23 kDa. Thus, it was demonstrated that the mutations abolish the dimer formation, which obviously suggests that one or several pairs of the six mutated residues are involved in the dimer formation.

It was shown by the use of $^1$H NMR spectra of each of the three mutated proteins that both domain-1 and domain-2 of the mutated double domains are folded very similar to folds in the unmodified proteins.

Example 3
Synthesis and Screening of Resin-bound Decapeptide Libraries

The synthesis of the resin-bound one-bead one-peptide library was performed using the portioning, mix procedure (Furka, À. et al., (1991) Int. J. Pep. Prot. Res. 37, 487–493). Polyethylene syringes served as reaction vessels throughout the synthesis and the final TFA-deprotection. TentaGel resin (Rapp Polymere, Tübingen, Germany) was divided into 18 aliquots and the protein L-amino acids except cysteine and histidine were used. Side-chains were protected with the following protecting groups: Asp(tBu), Glu(tBu), Tyr(tBu), Ser(tBu), Thr(tBu), Asn(trt), Gln(trt), Lys(Roc), Trp(Boc), Arg(pmc). Fmoc-protected amino acids (5 eq; Milligen or Novabiochem) were coupled overnight using 5 eq DIC and 5 eq HOBt. Removal of the Fmoc group was accomplished with 25% piperidine in DMF for 20 min. The side chain protecting groups were removed with 82.5% TFA, 5% anisole, 59 H$_2$O, 5% EDT, 2.5% thioanisole at room temperature for 2.5 h followed by washing with tetrahydrofuran and 1% HOAc and the resin was subsequently lyophilised. Screenings were done by incubating 2 ml resin (equivalent to ca. 10$^6$ beads) with biotinylated receptor in Tris/HCl buffer (Tris/HCl 0.025 M, pH 7.2, 0.25 M NaCl, 0.1% (w/v) Tween 20) containing 0.1% Gelatin (Sigma) for 60 min. Subsequently the resin was washed in Tris/HCl buffer and incubated with avidin-alkaline phosphatase (diluted 1:20000) for 30 min. The substrates BCIP/NBT (Sigma) were added as described by,the procedure by Lam et al. (1992) and stained beads were removed for micro sequencing. The library was screened with the receptor NCAM Ig1-PP (10 mg/ml).

Example 4

Sequencing of Beads and Selection of Peptides to be Synthesised

The most intensely stained beads were selected under stereo microscope and sequenced on an ABI 470A equipped with an ABI 120A HPLC. The 22 peptide sequences obtained (SEQ ID NO:1 to SEQ ID NO:22) are shown in FIG. 4A. A conspicuous finding was the high prevalence of the basic amino acids lysine (K) and arginine (R) in these identified NCAM Ig1 binding sequences. Peptide sequences to be synthesised and used in the further investigations were chosen by aligning the obtained sequences and examining these for repeated patterns revealing putative motifs. Three apparent motifs were identified within the peptides. The first motif was the sequence K/R-K/R-P-K/R-K/R-N/S that was partially conserved in a group of peptides including the C3 peptide as shown in FIG. 4B. The second motif was K/R-K/R-E-K/R-X-Kv/R-K/R found partially conserved in three peptides including D3 (FIG. 4C). The third motif, G-X-K/R-P-K/R, was found in two peptides including D4 (FIG. 4D).

Example 5

Synthesis of Peptides

One peptide, Ig1-p (SEQ ID NO: 26) derived from the sequence of NCAM Ig1 was synthesised as described below. In addition, one peptide, Ig2-p 9 (SEQ ID NO: 23) derived from the sequence of NCAM Ig2 was synthesised as described below. From combinatorial libraries 22 NCAM Ig1-binding sequences (SEQ ID NO: 1–22) were identified.

Three peptides, C3 (SEQ ID NO: 1), D3 (SEQ ID NO: 2) and D4 (SEQ ID NO: 3) were selected for further analysis and synthesised on TentaGel resin with Rink amide linker (p-((R,S)-α-(1-(9H-fluoren-9-yl)-methoxyformamido)-2,4-dimethoxybenzyl)phenoxyacetic acid (Novabiochem)) using Fmoc-protected amino acids (3 eq.). Coupling was performed for >60 min. with TBTU (3 eq.), HOBt (3 eq.) And DIEA (4.5 eq.) in a manual multicolumn apparatus. Fmoc was deprotected with 20% piperidine in DMF for 10 min. Synthesis of peptide dendrimers was accomplished by coupling Fmoc-Lys (Fmoc)-OH (Novabiochem) to the linker resin followed by Fmoc-deprotection of the Fmoc group and further coupling of Fmoc-Lys (Fmoc)-OH was performed. After Fmoc-deprotection the synthesis of peptides was performed as above for the monomeric peptides. Peptidyl resins were deprotected with TFA 90%, 5% $H_2O$, 3% EDT, 2% thioanisole, precipitated in diethyl ether, washed three times in diethyl ether, solubilised in 5% AcOH and lyophilised. Amino acid analysis was performed using Waters picotag and Waters 501 pump connected to WISP 712. Waters 600E equipped with Waters 996 photodiode array detector was used for analytical and preparative HPLC on $C_{18}$ columns (Delta-Pak 100 Å 15 µm, Millipore). MALDI-MS was done on a VG TOF Spec E, Fisions Instrument. The peptides were at least 95% pure as estimated by HPLC.

To investigate the role of important residues of the Ig2-peptide, Ig2-p, two control peptides, called P2-3S and P2-4S respectively of the sequences GSILASGESNFK (P>-3S) and GSILASGSSNFK (P2-4S) were constructed. In P2-3S (SEQ ID NO: 24), the residues Arg-2, Arg-6 and Ile-9 were substituted with serines corresponding to a mutation of residues Arg-192, Arg-196 and Ile-199 of the NCAM Ig2 domain. In P2-4S (SEQ ID NO: 25), the residues Arg-2, Arg-6, Glu-8 and Ile-9 were substituted with serines corresponding to a mutation of residues Arg-192, Arg-196, Glu-198 and Ile-199 of the NCAM Ig2 domain.

To investigate the role of the individual residues in the C3-sequence, so-called scrambled peptides, comprising the same residues as C3 but in a different sequence, were constructed in the same way (121, 114 and C3scr in FIG. 7). Similarly, scrambled peptides corresponding to the residues in the D3 and D4 sequences were constructed (scrambled D3 and scrambled D4 in FIG. 7). Furthermore, peptides containing the C3-sequence in which basic amino acids (Ks and Rs) were substituted with alanines were constructed (116–119 in FIG. 7) to explore the role of these particular amino acids. Likewise, a peptide corresponding to the C3-sequence in which the proline-residue (Xaa$^1$) was substituted with an alanine was constructed. To further investigate the role of the basic amino acid residues in C3, a peptide containing the C3-sequence in which the basic amino acids were modified by acetylation was constructed b(C3dacetyl. K(120) in FIG. 7).

Example 6

Plasmon Surface Resonance Analysis

Real-time biomolecular interaction analysis was performed using a BIAlite instrument (Pharmacia Biosensor AB, Sweden). All experiments were performed at 25° C. using Hepes buffered saline (MHBS: 10 mM Hepes pH 7.4, 150 mM NaCl, 3.4 mM EDTA, 0.0059; v/v Surfactant P20 (Pharmacia Biosensor, Sweden) as running buffer. The flow rate was 5 ml/min. Dendrimer peptides C3, D3 and D4 (four peptide-monomers coupled to a backbone consisting of three lysines) were immobilised on a sensor chip CM5 (Pharmacia Biosensor AB, Sweden) using the following procedure: the chip was activated by 10 ml 0.05 M N-hydroxysuccinimide, 0.2 M N-ethyl-N'-(dimethylaminopropyl)carbodiimide; peptides were immobilised using 35 ml peptide solution in HBS at a concentration of 60 µg/ml; finally the chip was blocked by 35 µl 1 M ethanolamine hydrochloride pH 8.5. Binding of Ig1 to dendrimer peptides: 50 ml of Ig1 or Ig1I at the indicated concentrations were applied. The chip was regenerated by two 5 ml pulses of 5 mM NaOH. Two independent experiments were performed. The results confirmed that C3, D3 and D4 bind to the NCAM Ig1 domain.

Example 7

Aggregation and Neurite Outgrowth

Figure 5:
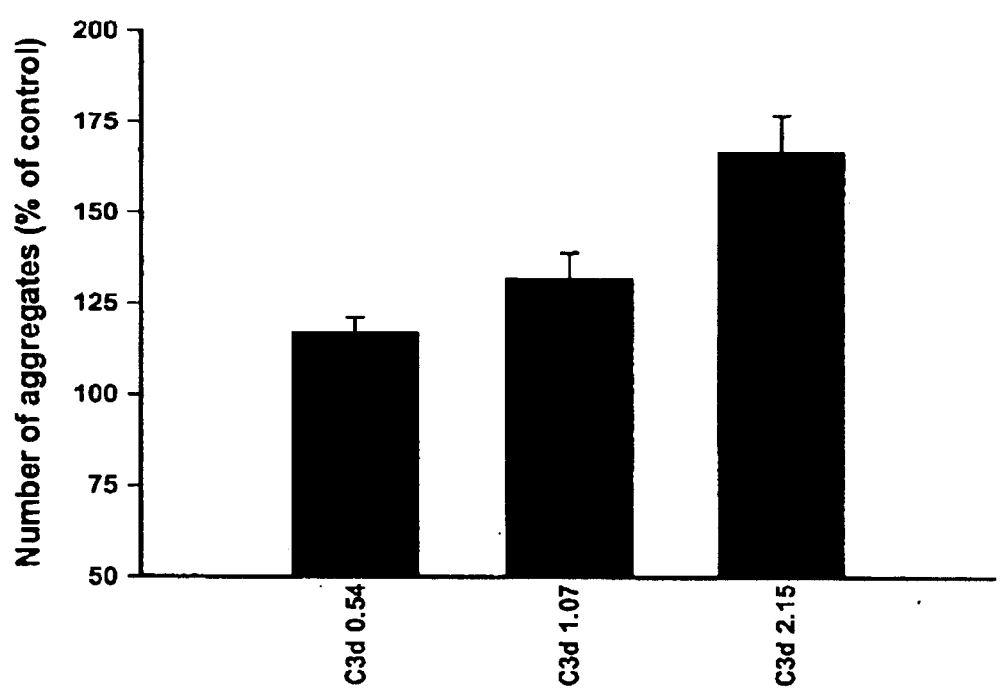
FIG. 5 shows the number of aggregates of primary hippocampal neurones formed after 24 h in culture in the presence of C3 dendrimer in concentrations of 1.07 $\mu$M and 2.15 $\mu$M (Example 7). The observed increase in the number of aggregates formed reflects an inhibition of the aggregation-process.
Figure 6:
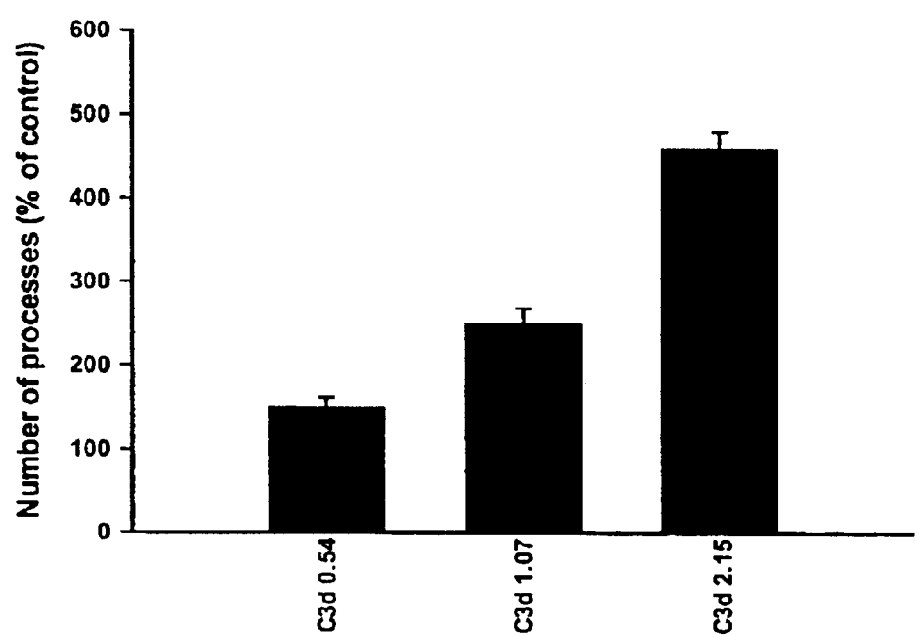
FIG. 6 shows the number of neuronal processes from primary hippocampal neurones formed after 24 h in culture in the presence of C3 dendrimer in concentrations of 1.07 $\mu$M and 2.15 $\mu$M (Example 7).

1) Influence of NCAM Ig1 binding compounds on NCAM mediated cell adhesion. Hippocampal cells were prepared from rat embryos gestational day 17–19. Cerebellar cells were prepared from postnatal day 4–7 mice. Cells were grown in a defined medium consisting of DMEM/F12 (Gibco, BRL) supplemented with N2 (Gibco, BRL) or Neurobasal supplemented with B27 (Gibco, BRL), in both cases supplemented with 20 mM HEPES (Gibco, BRL), 0,4% w/v bovine serum albumin (Sigma) and 100 iU/ml penicillin-streptomycin. Dissociated cells were seeded in 60 well microliter plates (50.000 in 15 ml per well) essentially as described (Maar et al., 1995). After 24 h, the amount of aggregates were counted. Peptides to be tested were added to the cell suspension immediately before seeding of cells in the microwells. When the NOAM Ig9 binding peptides, C3, D3 and D4 were present during the aggregation of cells, a higher number of cell aggregates resulted when quantified 24 h after seeding of cells. FIG. 5 shows the number of aggregates measured 24 h after seeding of cells in the presence of C3d in the indicated concentrations in μM (concentration calculated with respect to the amount of peptide monomers present on the peptide-dendrimers). The peptide moreover resulted in an increase in the number of neuronal processes formed (FIG. 6). D3- and D4-dendrimer likewise increased the number of aggregates formed after 24 h. Scrambled peptides based on the C3-sequence also inhibited aggregation. The effect of the various peptides tested is shown in FIG. 7. To localise the active residues of the C3-peptide, alanine substitutions were carried out. Substituting the proline with an alanine did not change the effect. Likewise, one basic amino acid could be substituted by alanine without a change in effect, thus such a peptide (termed "116" in FIG. 7) In contrast, peptides with two to four alanine substitutions of the basic residues had no effect on aggregation indicating that these basic residues are important for the effect of C3. Similar aggregate cultures were prepared in the presence of C3 as monomer, dendrimer or as BSA-coupled 20-mer. Different forms of the C3 peptide were tested it was found that monomeric, dendrimeric and BSA-coupled forms of C3 had similar effects on aggregation. However, the dendrimer of the C3 sequence was the most potent form, presumably due to the ability to link several of the receptor domains. To verify that the receptor was situated in the NCAM Ig1 domain, the cells were incubated with this domain prepared in *Pichia pastoris* as described in Example 1 in solution in a concentration of 5.4 or 54 μg/ml. The presence of the NCAM Ig1 domain abrogated the effect of C3 demonstrating an interference with NCAM-mediated cell adhesion of C3. These experiments show that the here identified NCAM Ig1 binding peptides influence NCAM mediated cell adhesion and thereby increase the number of cell aggregates and neuronal processes formed in cultures of primary neurones grown at high densities.

The effect of the NCAM Ig2 domain and the peptides Ig2-p (SEQ ID NO: 23) and Ig1-p (SEQ ID NO: 26) was tested in hippocampal aggregate cultures prepared as described above. It can be seen that the number of cellular aggregates increased in a dose-dependent manner when cultures were treated with various concentrations of the Ig domain 2. In treated cultures, aggregates were smaller when compared to control cultures, indicating that the Ig domain 2 causes a decrease in intercellular adhesion. The Ig2-peptide also inhibited aggregation of cells. By comparing the effects of the Ig domain 2 and Ig2-peptide, it can be seen that both compounds strongly inhibited aggregation in a concentration-dependent manner. To test whether inhibition of aggregation of hippocampal neurons by the Ig2-peptide was specific, peptides in which several residues involved in the binding of the Ig domain 2 to the Ig domain 1 were substituted with Ser were tested. The peptide P2-3S (SEQ ID NO: 24), in which Arg-2, Arg-6 and Ile-9 were substituted with Ser had no inhibitory effect. An Ig2-peptide, P2-4S (SEQ ID NO: 25), in which additionally Glu-8 was substituted with Ser had only a slight inhibitory effect on aggregation of hippocampal cells. These results show that amino acid residues in the Ig2 domain involved in its binding to the Ig domain 1 are important for NCAM mediated intracellular adhesion. We also tested the effect of the Ig1-P peptide in aggregate cultures as described. This peptide also inhibited aggregation of cells showing that the part of the NCAM Ig2 domain contributing to the binding site in the NCAM Ig1–Ig2 domains is important for NCAM mediated intracellular adhesion 2) NCAM Ig1 binding compounds promote neurite outgrowth Hippocampal cells were prepared from rat embryos gestational day 18. 5000 cells/well, corresponding to approximately 4000 cells/cm$^2$, were seeded in 8 well is LabTek. Tissue Culture Chamber Slides with a growth surface of Permanox plastic (NUNC A/S, Denmark) or fibronectin (cocultures) and maintained for 20 h as described in Example 7 (1).

For cocultures, neurones were seeded on monolayers of fibroblasts, either L-cells or 3T3 cells with or without NCAM-B expression. Neurones were visualised using immunohistochemical staining for growth associated protein 43 kD (GAP43). Briefly, cells were fixed 30 min in 4% paraformaldehyde in phosphate buffered saline (PBS). The primary antibody was rabbit anti-GAP43 1:100 in PBS with 1% fetal bovine serum(FBS), 0.1% bovine serum albumin (BSA), 50 mM glycine, 0.02% NaN$_3$, 2% saponine 1 h at room temperature or overnight at 4° C. The second antibody was biotinylated swine-anti-rabbit immunoglabulins 1:100 in PBS with 1% BSA 1 h at room temperature. The third "layer" was streptavidine coupled to FITC or horse radish peroxidase (HRP) 1:100 1 h at room temperature. Between layers, washings were performed 3×20 min in P3S with 1% BSA. Images of living or stained neurones were captured and analysed by the image analysis program Line Length created at the Protein Laboratory. Putative axons were identified as the longest neurite of each cell. Only neurites longer than 10 mm were considered.

FIG. 8 shows the effect of C3 added to cocultures of primary hippocampal neurones on monolayers of fibroblasts stably expressing NCAM-140 (LBN) or monolayers of fibroblasts without NCAM expression (LVN). In this model, NCAM expressed by transfected fibroblasts induce an increased neurite outgrowth from neurones. The mean length of neurites on NCAM-expressing fibroblasts was longer than the mean length of neurites on fibroblasts without NCAM expression. In the presence of C3, there was no difference between the length of neurites on fibroblasts with or without NCAM expression showing that C3 binds to NCAM (0.54 or 5.4 μM) in both cerebellar and hippocampal neurones. When neurones were maintained on fibroblasts without NCAM-expression, neurite extension was stimulated by C3 in similar concentrations when compared to controls maintained in the absence of C3. This shows that C3 stimulates neurite outgrowth.

Figure 9:
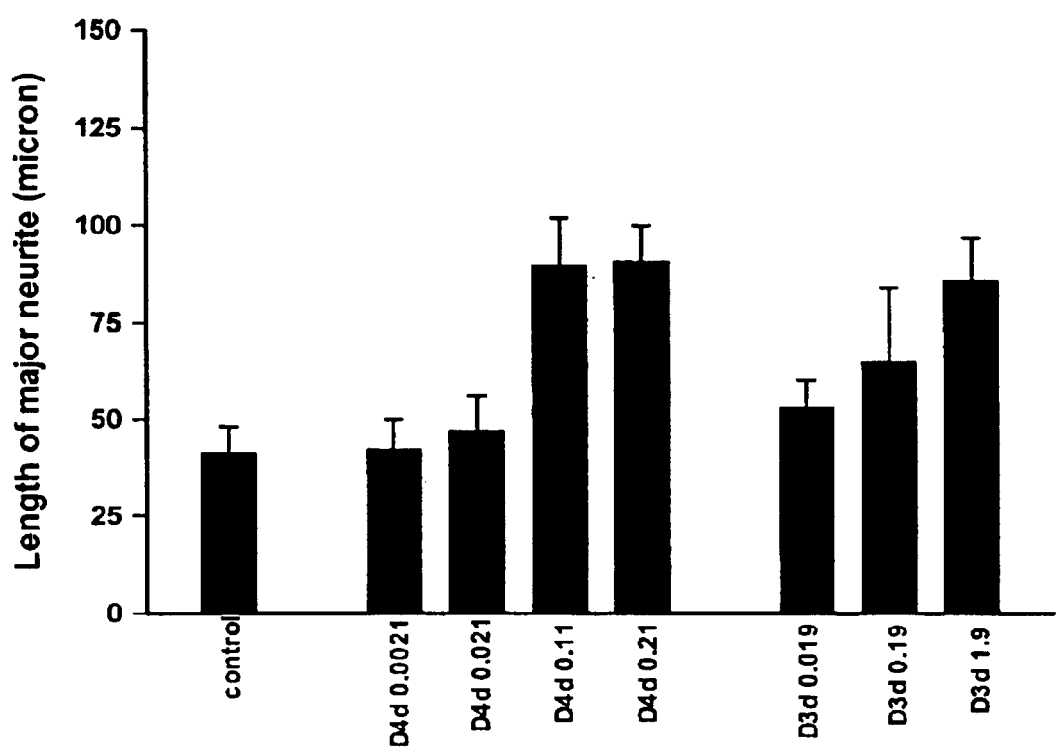
FIG. 9 shows the effect of D3 and D4 dendrimers on neurite outgrowth from primary hippocampal neurones in the indicated doses in $\mu$M.
Figure 10:
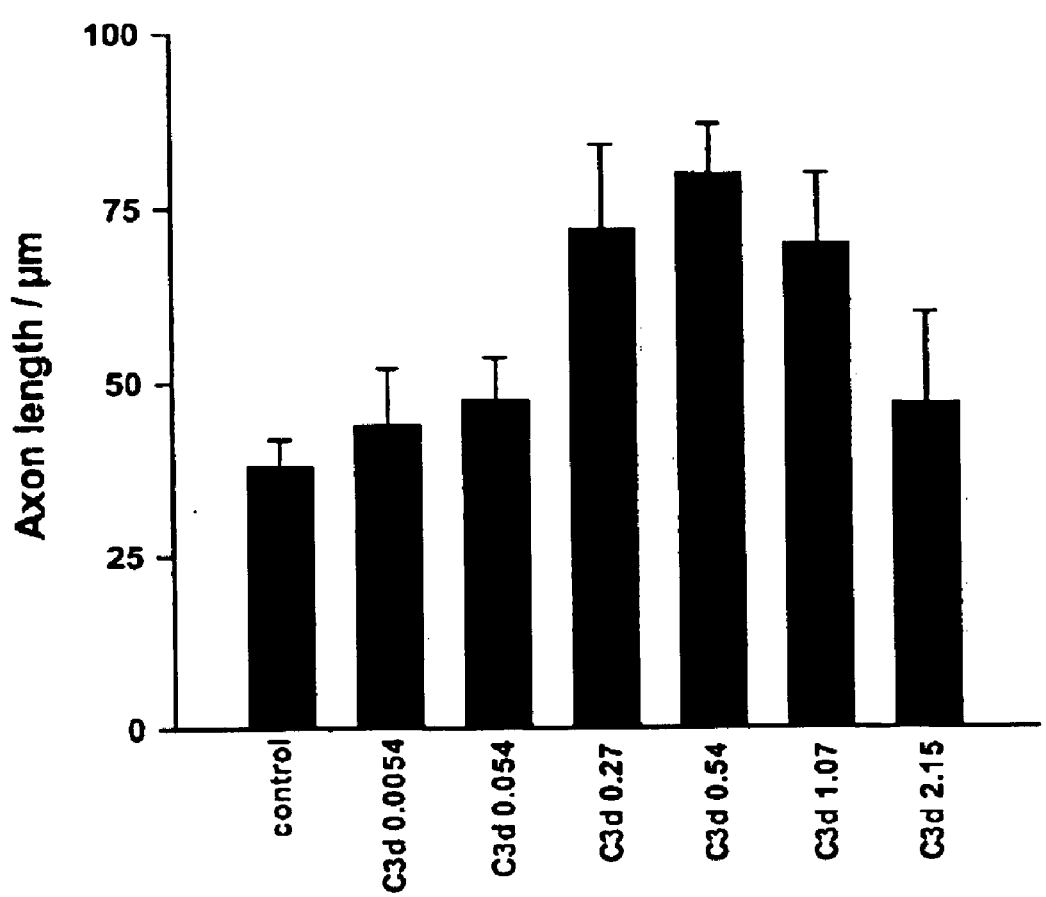
FIG. 10 shows the effect of C3 peptide dendrimer on neurite outgrowth from primary hippocampal neurones in the indicated doses in $\mu$M. Neurite outgrowth is measured as the mean length of the longest neurite ("axon length"). Primary hippocampal neurones from E18 rats were maintained for 21 h on fibronectin.

To investigate the stimulatory effect on neurite extension, cells were prepared as described and seeded on a substrate of plastic or fibronectin. Cells were then maintained for 21 h and neurite outgrowth was analysed by computer-assisted image analysis using the program Linelength. The mean length of the longest neurite of each cell was measured for neurites longer than 10 μM. In addition, the mean number of branchpoints per neurite and the mean number of neurites per cell were determined. NCAM Ig1 binding peptides C3, D3 and D4 were added immediately before seeding the cells. This resulted in an increase in neurite outgrowth. The results for the measurements of the longest neurite per cell are shown in FIG. 9 and FIG. 10 in which the concentrations are given in μM. A similar dose-response relationship was found when measuring the number of neurites per cell and the branching of neurites. Scrambled peptides with similar amino acid composition but altered sequences had similar effects as C3, D3 and D4. The effect on neurite outgrowth of the tested NCAM Ig1 binding peptides and the various control-peptides is shown in FIG. 7.

Figure 11:
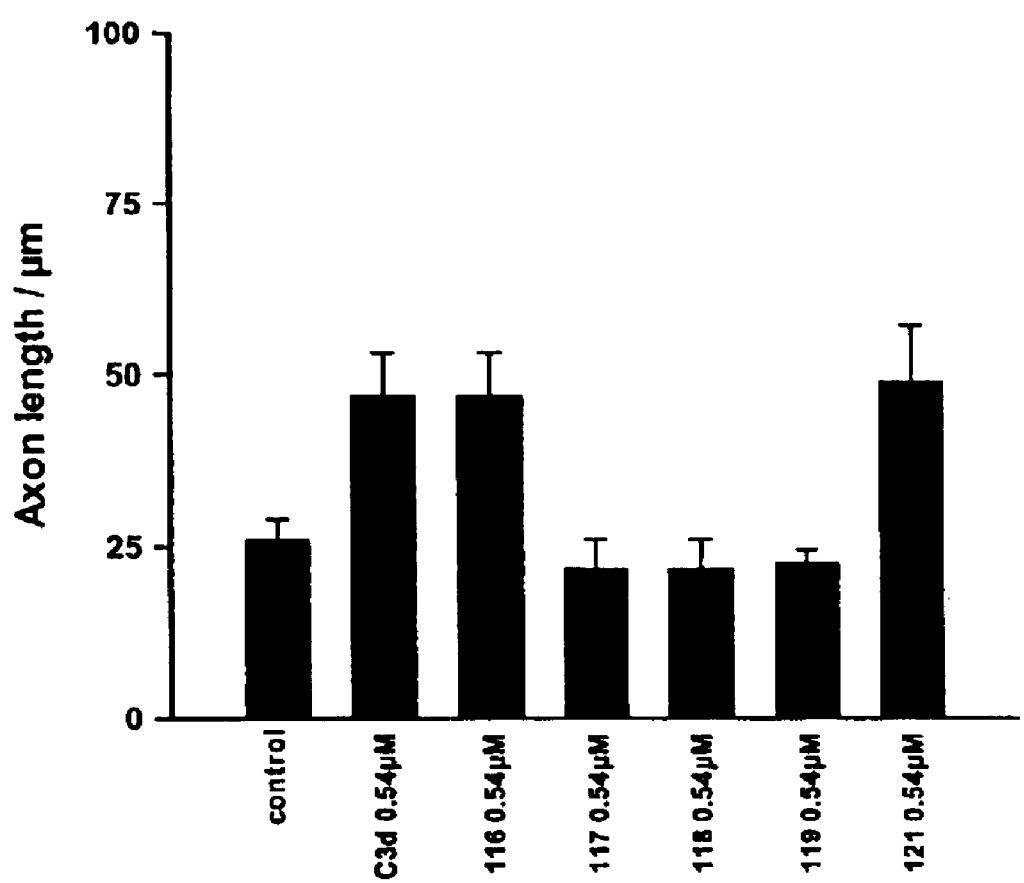
FIG. 11 shows neurite outgrowth measured from neurones maintained on plastic. Effect of C3d and control peptides (see FIG. 7) on neurite outgrowth in a concentration of 0.54 $\mu$M.
Figure 12:
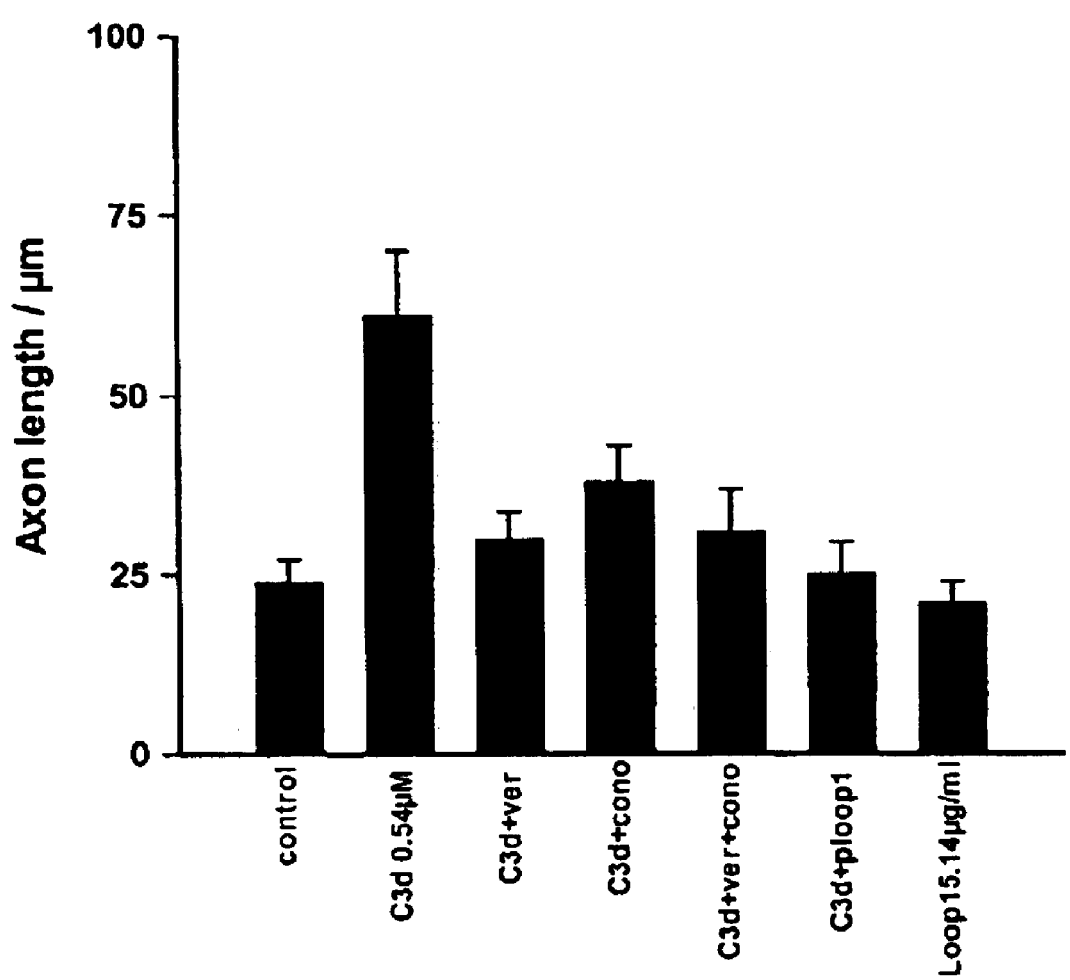
FIG. 12 shows the effect of various inhibitors of signal transduction on neurite outgrowth from primary hippocampal neurones maintained on fibronectin stimulated by C3d (0.54 $\mu$M see Example 7 2). Ver: verapamil (10 $\mu$M), Cono: omega-conotoxin GVIA (0.27 $\mu$M), ploop1: NCAM Ig1 prepared in *Pichia pastoris* as described in example 1, 0.54 $\mu$M.

To investigate which properties of the NCAM Ig1 binding peptides were important for the observed neuritogenic effect, peptides corresponding to the C3-sequence, but having alanine substitutions of basic amino acids were tested for their effect on neurite outgrowth (FIG. 11). The length of the longest neurite, the number of neurites per cell and the branching of neurites was strongly stimulated by the C3 peptide (0.54 µM). A peptide with a similar sequence apart from one alanine substitution of a basic amino acid had similar effects. In contrast, peptides with two to four alanine substitutions had no effect. To investigate the mechanisms of this effect, the C3 peptide (0.54 µM) was added in combination with various compounds known to inhibit NCAM dependent signalling (FIG. 12 and FIG. 13). The following compounds were found to inhibit the stimulatory effect of C3 on neurite extension: 10 µM verapamil ("ve" inhibitor of L-type voltage dependent calcium channels), 0.27 µM omega-conotoxin GVIA ("cot" inhibitor of N-type voltage dependent calcium channels), 1 µg/ml pertussis toxin ("pertus" inhibitor of certain G-proteins), an erbstatin analogue ("erb" 0.2 µM, inhibitor of certain tyrosine kinases), antibody to an acidbox epitope in fibroblast growth factor receptors (FGF-Rs) (1:200 inhibitor of NCAM-FGF-R binding and signalling), a peptide corresponding to the so-called CAM homology domain (CHD) (175 µM, inhibitor of NCAM-FGF-R binding and signalling). In addition, the neuritogenic effect of C3 was completely abrogated by the NCAM Ig1 domain, prepared as described in Example 1, in solution. These results show that C3 stimulates neurite outgrowth by binding to the NCAM Ig1 domain and thereby activating signalling pathways in the neurone that are sensitive to the above mentioned inhibitor-compounds.

Figure 14:
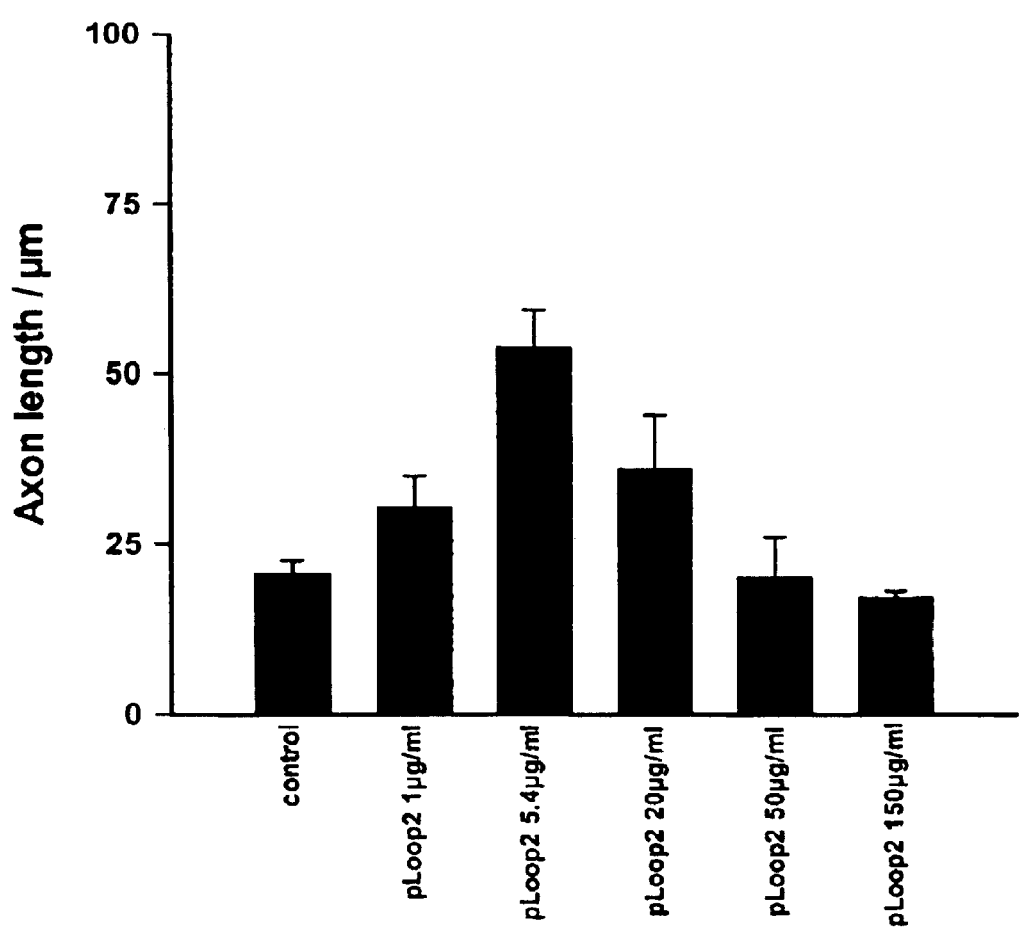
FIG. 14 shows the effect of NCAM Ig2, prepared in *Pichia pastoris* as described in example 2, on neurite outgrowth from primary hippocampal neurones maintained on fibronectin. NCAM Ig2 was added in the indicated concentrations in $\mu$g/ml (1 $\mu$g/ml corresponds to 0.1 $\mu$M) Neurite outgrowth is measured as the mean length of the longest neurite ("axon length").
Figure 15:
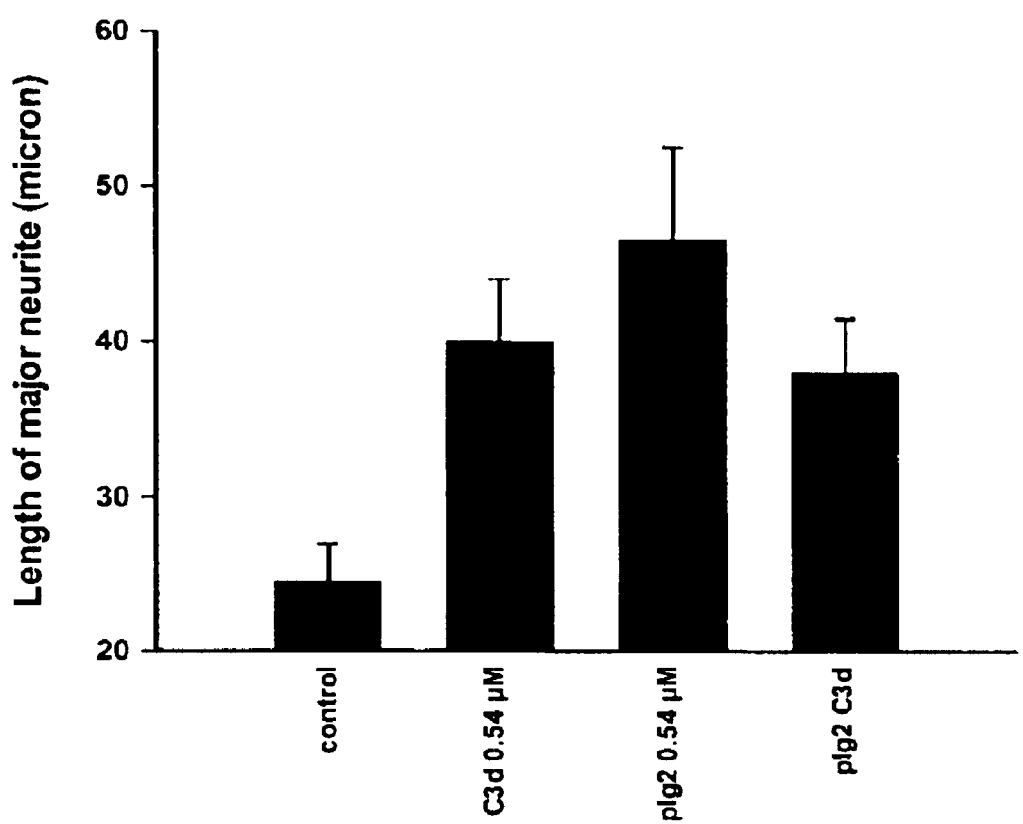
FIG. 15 shows the effect of C3d and NCAM Ig2 added in, combination on neurite outgrowth from primary hippocampal neurones maintained on fibronectin.

To investigate the endogenous ligand of NCAM Ig1, the NCAM Ig2 domain was prepared in *Pichia pastoris* (see Example 2) and tested for its effect on neurite outgrowth from primary hippocampal neurones maintained on a substrate of fibronectin. The polypeptide comprising the domain was added to the culture-wells immediate before seeding of cells. FIG. 14 shows the mean length of the longest neurite measured 21 h after seeding of primary hippocampal neurones in the presence of NCAM Ig2 polypeptide ("pLoop2") in the indicated concentrations. It shows that NCAM Ig2 stimulates neurite outgrowth with a bell-shaped dose-response relationship similar to that of the C3 peptide. The maximal neuritogenic effect of NCAM Ig2 was found at a concentration of 5.4 µg/ml which corresponds to 0.54 µM of the domain. This is the same concentration at which the C3 peptide had a maximal neuritogenic effect. The NCAM Ig2 domain was then tested in combination with compounds known to inhibit NCAM dependent signalling as described for C3 above. These compounds also inhibited the neuritogenic effect of NCAM Ig2. Thus, NCAM Ig2 and C3 both binds to NCAM Ig1 and both NCAM Ig2 and C3 stimulate neurite extension by activating identical signal transduction pathways. Therefore, NCAM Ig2 and C3 were tested for their effect on neurite outgrowth when added in combination. The effect of NCAM Ig2 was found to be non-additive to that of C3 (FIG. 15). The results shown that NCAM Ig2 and C3 stimulate neurite extension by identical mechanisms. They both bind the NCAM Ig1 domain and thereby activate identical signalling pathways leading to neurite outgrowth.

It was shown that the Ig domain 2 and a peptide encompassing residues 191–202 of the Ig domain 2 had 9 direct effect on neurite outgrowth. Hippocampal cells were grown at a low density and treated with various concentrations of the compounds as described above. To measure neurite outgrowth from hippocampal neurons a simple procedure based on stereological principles was used. Briefly, by means of the software package "ProcessLength" (Protein Laboratory, University of Copenhagen) an unbiased counting frame containing a grid with a certain number of test-lines was superimposed on images of the cell cultures. The number of intersections of cellular processes with the test-lines was counted and related to the number of cell bodies, thereby allowing quantification of the total neurite length per cell. Both the Ig domain 2 and the Ig-peptide strongly stimulated neurite outgrowth from hippocampal neurons in a dose dependent manner. Substitution of either three or four residues with Ser in the Ig2-p as described abrogated the ability of the Ig2-peptide to stimulate neurite outgrowth. In order to increase potency of the Ig2-peptide, we synthesized a dendrimer (Ig2-pd) composed of four monomers coupled to a lysine backbone. The dendrimer had a strong neuritogenic effect with a bell shaped dose-response relationship within the same range of concentrations as it was found for the stimulatory effect of the Ig domain 2. It was observed that in hippocampal cultures treated with the dendrimer at the optimal concentration 3.6 µM, neurons exhibited a much higher extend of morphological differentiation than did controls. Thus, we identified an NCAM-derived peptide ligand with a strong neuritogenic activity. Peptides, in which several residues corresponding to those involved in the binding of the Ig domain 2 to the Ig domain 1 were substituted with Ser, were tested. The peptide P2-3S, in which Arg-2, Arg-6 and Ile-9 were substituted with Ser had no stimulatory effect. An Ig2-peptide, P2-4S, in which additionally Glu-8 was substituted with Ser likewise had no stimulatory effect on neurite outgrowth from hippocampal cells. Thus these residues are important for the neuritogenic effect of the Ig2-p peptide. Accordingly, the residues Arg-192, Arg-196, Glu-198 and Ile-199 can be considered to be important for the neuritogenic effect of the NCAM Ig2 domain.

Moreover, hippocampal cell cultures were grown in the presence of the Ig2-p peptide and the first Ig domain. It was seen that the addition of the Ig domain 1 caused a decrease in the neuritogenic activity of the Ig2-peptide. In addition, antibodies against FGFR, CAM homology domain (CHD) of the receptor and a specific inhibitor of phospholipaseC-γ (PLCγ) was demonstrated to inhibit neurite outgrowth induced by the Ig2-p peptide. Indeed, both anti-FGFR and CHD inhibited, while U-73122, the inhibitor of PLCγ, completely abrogated Ig2-peptide induced neurite outgrowth. These data show that the Ig2-peptide stimulates neurite outgrowth through the NCAM-FGFR signalling pathway.

The Ig1-p peptide was further shown to promote neurite outgrowth in hippocampal cell cultures prepared as described above. This shows that a sequence corresponding to the part of the Ig1 domain involved in the NCAM Ig1–Ig2 binding can directly stimulate neurite outgrowth.

We additionally tested whether mutations in these residues change the activity of the Ig domain 1–2 with regard to neurite outgrowth. It was seen that the normal Ig domain 1–2 (Ig1–2) had only slight, if any, effect on neurite outgrowth, which is not surprising since In a dimer all potentially binding sites are blocked. In the presence of the mutated double domain, extension of neurites from hippocampal cells was inhibited in a dose dependent manner. We therefore conclude that the residues potentially involved in the binding between the first two Ig domains are important for NCAM-mediated neurite outgrowth.

Example 8

Proliferation

Figure 16:
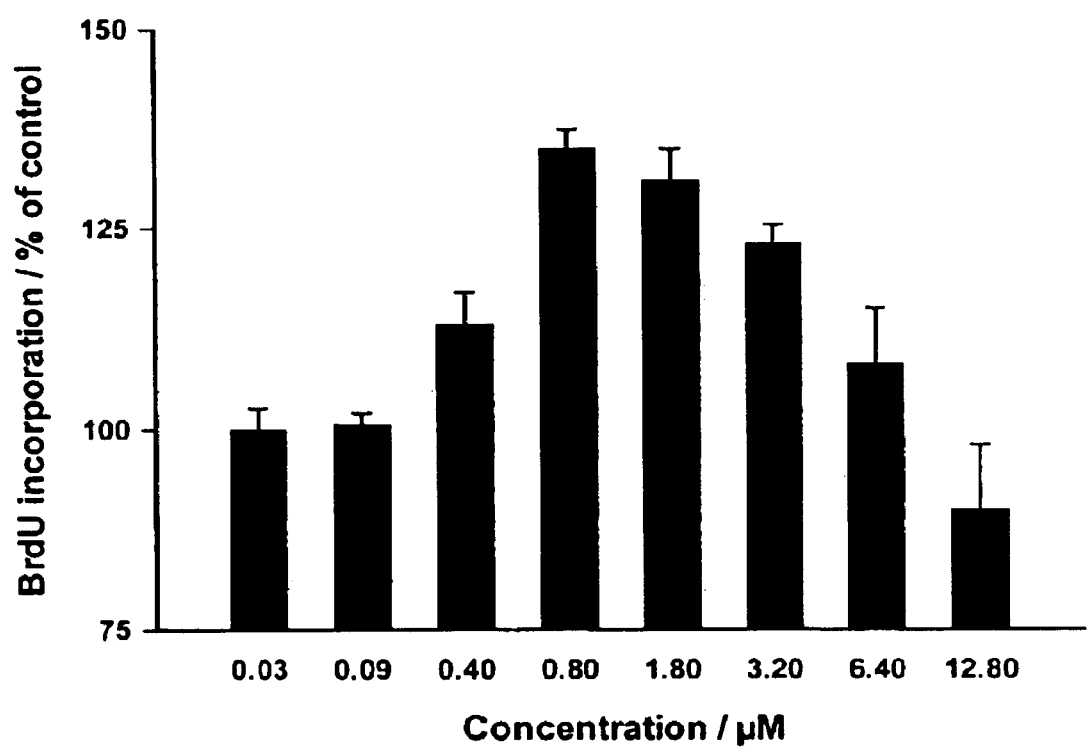
FIG. 16 shows the effect of C3d in the indicated concentrations in $\mu$M on proliferation of primary hippocampal neurones measured as incorporation of BrdU as described in example 8.

Cell proliferation was determined by incorporation of 5-bromo-2'-deoxyuridin in a cell proliferation ELISA system (Amersham Life Science) according to the procedure of the manufacturer. Primary hippocampal neurones were seeded in microtiter plates at a density of 33000 cells per well. In the presence of C3d in a concentration of 0.8 µM, an increased incorporation of BrdU was observed indicating a stimulation of neuronal proliferation. The dose-response curve was bell-shaped (FIG. 16), thus at higher concentrations, C3 inhibited proliferation. C3 also promoted proliferation of neuroblastoma cells. However, the net effect on proliferation depended on the growth status of cell. Hence in PC12 cells, an inhibitory effect on proliferation was observed concomitant with an increased neurite outgrowth indicating that the peptide stimulated differentiation of these cells. These results show that NCAM Ig1 binding compounds can influence proliferation of neurones. The net effect depends on the growth status of the cells but under the proper circumstances, a stimulation of proliferation will result.

Example 9
Cell Growth

Cell growth is another way of monitoring proliferation of the cells. Primary hippocampal cells were seeded into 96 well microtiter culture plates (Nunc A/S) at a density of 20.000 or 40.000 per well in defined medium as described above. Cells were grown for 48 h, centrifuged in order to remove medium, fixed in 3.7% formaldehyde in PBS for 15 min and stained with 0.5% Cristal Violet in 20% methanol. for 15 min. Stained cells were thoroughly washed with Milli Q purified water, thereafter residual dye was solubilised with 0.1 M sodium citrate in 50% ethanol pH 4.2 and absorbance measured at 550 nm. When added in 0.8 µM immediately preceding seeding of cells, C3 was, shown to increase cell growth.

Example 10
Structure Determination of the NCAM Ig1–Ig2 Binding Site

By means of the NMR spectra of the two domains of NCAM and their known three-dimensional structures, it was possible to locate the residues that form the binding sites on the surfaces of the two domains. In the $^{15}$N-HSQC spectrum of $^{15}$N labeled protein a signal for each amino acid residue with both a peptide nitrogen and proton can be observed. The determination of changes in chemical shifts of the signals is therefore a method to locate the sites in the protein that are perturbed for instance by the binding of another molecule. To the $^{15}$N labeled sample of domain-1 of NCAM unlabelled domain-2 was added to make an excess of two to one in domain-2. The corresponding experiment was performed with the $^{15}$N labeled domain-2 of NCAM. The recorded changes in $^1$H and $^{15}$N chemical shifts for each residue were mapped onto the structures of domain-1 and domain-2, respectively using a cut-off at 0.04 ppm and 0.2 ppm, respectively for the perturbed $^3$H and $^{15}$N chemical shift. The residues chat experience Nigh chemical shift-perturbation in domain-1 are Gly-12, Gly-17, Glu-18, Ser-19, Lys-20, Phe-22, Cys-24, Arg-51, Leu-64, Ile-66, Tyr-67, Ala-69, Ile-71, Asn-94 and Lys-96, and in domain-2 the residues are Thr-131, Ile-132, Glu-173, Gly-174, Ile-176, Leu-177, Ala-178, Gly-180, Glu-181, Ile-182, Asn-183 and Phe-184. The chemical shift changes of the peptide backbone NMR signals for these residues in the two domains report, that the presence of the other NCAM domain is changing the chemical environment at these sites, suggesting that the other NCAM domain is binding in the neighborhood of these.

The mapping of the residues perturbed by the addition of the other domain show very clearly that these residues are located in one well-defined and coherent patch on each of the domain surfaces. This is a good indication that the two patches of residues on the surface are either parts of or in the neighborhood of the binding site for the interaction between the two domains.

Three samples were used in the structure determination, (a) unlabeled NCAM domain-2 in H$_2$O, ~1 mM, (b) unlabelled NCAM domain-2 in D$_2$O, ~1 mM, and (c) $^{15}$N-labeled NCAM domain-2 in H$_2$O, ~1 mM. In all cases the buffer was 50 mM NaCl, 20 mM potassium phosphate pH 6.0. The following NMR spectra were recorded of NCAM domain-2 and used for assignment: TOCSY, respectively, in H$_2$O and in D$_2$O both using a mixing time of 70 ms; DQFCOSY, respectively, in H$_2$O and in D$_2$O; NOESY, respectively in H$_2$O and in D$_2$O using either a mixing time of 100 ms or of 200 ms; a $^{15}$N HSQC; a $^{15}$N TOCSY-HSQC with a mixing time of 70 ms; and a $^{15}$N NOESY-HSQC with a mixing time of 100 ms. The NMR experiments were performed on a Bruker AMX-600 MHz spectrometer and on a Varian Unity Inova 750 MHz spectrometer. All spectra were recorded at 298 K. The assignment of the $^1$H and $^{15}$N resonance lines from these spectra were performed using the computer program PRONTC. For structure calculations a distance geometry/simulated annealing protocol from X-PLOR was used. 100 structures were calculated, and 70 structures were accepted by X-PLOR, discriminating any structure with a NOE-violation >0.5 Å and/or an angle-violation >5°. Of these 70 structures the 20 structures with lowest energy were chosen to represent the structure of NCAM domain-2. The structure calculations used 107 intra-, 300 sequential-, 145 short- range- and 466 long range-NOEs derived from 2D-NOESY and $^{15}$N NOESY-HSQC spectra, with upper bounds of 2.7, 3.3, 4.3 and 5 Å. These were increased by 0.5 Å when the NOE restraint included a methyl group. 41$\phi$ dihedral angle restraints were applied with bounds of −120±40° and −57+40°, respectively, when the $^3J_{HNH\alpha}$ coupling constant derived from the DQFCOSY and the NOESY spectra were >8 Hz or <5 Hz, respectively. 34 $\chi^1$ dihedral angles were assigned by estimates of the $^3J_{H\alpha H\beta}$ coupling constants and the NOE intensities from, the DQFCOSY and the NOESY spectra, respectively. In the final structure calculations 78 hydrogen bond restraints were selected and applied as NOE restraints into the calculations with upper bounds of 2.1 Å for the $H^N$—O distance and 3 Å for the N—O distance. The structures of NCAM domain-2 were examined using the program PROCHECK_NMR. The elements of secondary structure were identified using MOLMOL and PROCHECK_NMR. For the binding studies of domain-1 and domain-2 Six $^{15}$N HSQC spectra of the following samples were recorded: a) $^{15}$N-HSQC of $^{15}$N-labeled domain-1 (1 mM and 0.5 mM); b) $^{15}$N-HSQC of $^{15}$N-labeled domain-2 (1 mM and 0–5 mM); c) $^{15}$N-HSQC of $^{15}$N-labeled domain-1 added unlabeled domain-2 (ratio 0.5 mM:1 mM); d) $^{15}$N-HSQC of 15N-labeled domain-2 added unlabeled domain-1 (ratio 0.5 mM:1 mM). The titrations of domain-1 to domain-2 were performed recording the chemical shift changes in the $^{15}$N HSQC spectra. All samples were measured at pH 6.0 and 298 K, 50 mM NaCl and 20 mM potassium phosphate. The NMR experiments were performed on a Varian Unity Inova 750 MHz spectrometer. Analysis of the spectra was performed using PRONTO. The affinity of the binding between domain-1 and domain-2, was determined in a titration experiment where $^{15}$N labeled domain-2 was titrated with unlabeled domain-1. In a 14-point titration with unlabeled domain-1 the change of chemical shifts was measured for 10 residues. Fitting of the binding curves for each of these 10 residues resulted in the same dissociation constant $K_d$ of $(2.5+2)\times10^{-3}$ M. The coherence of the patches of residues perturbed on the surfaces of the two NCAM domains as well as the identical binding constants measured for the perturbed sites in domain-1 all suggest that the binding is very specific although weak under the conditions of the NMR measurements. The titration was performed adding aliquots of a 2:1 mixture of unlabelled domain-1 (2 mM) and $^{15}$N labeled domain-2 (1 mM) to a 1 mM solution of $^{15}$N labeled domain-2. In this way the concentration of $^{15}$N labeled domain-2 was maintained at 1.0 mM, and the concentration of domain-1 was gradually increased. Protein concentrations were determined by amino acid analysis. Fitting of the titration points to a binding curve of a two-component interaction was performed using the program CANOO. For model building of the dimer of the first two domains of NCAM, (Ig1–Ig2) a distance geometry/simulated annealing—and restrained dynamic—protocol from X-PLOR was used. As restraints were used the restraints obtained from NOE and coupling constant measurements of domains-1 and -2. The proposed intermolecular salt bridges were built into the model as hydrogen bond restraints and applied as NOE restraints into the calculations with upper bounds of 2.1 Å for the $H^N$—O distance and 3 Å for the N—O distance. Twenty structures were calculated and ten of these structures with the lowest energy were selected for the evaluation of the model building of (Ig1–Ig2) of NCAM.

References

Andersson A M. Biochemical Journal 1993; 290:641–8.
Beggs, H. E. N Journal of Biological.Chemistry 1997, 272, no. 13: 8310–8319.
Carenini S. Cell & Tissue Research 1997; 287:3–9.
Cremer H Molecular & Cellular Neurosciences 1997; 8:323–35.
Cremer H. Nature 1994; 367:455–9.
Daniloff J K. Journal of Cell Biology 1986; 103:929–45.
Daston M M. Journal of Neuroscience 1996; 16:5488–97.
Doherty P. Nature 1992; 356–791–3.
Doherty P. Molecular and Cellular Neuroscience 1996; 8:99–111.
Doyle E. Journal of Neuroscience Research 1992; 31:513–23.
Edelman G M Cold Spring Harbor Symposia on Quantitative Biology. Cold Spring Harbor Laboratory Press, 1990: 303–18.
Fazeli S. Seminars in the Neurosciences 1997; 8:367–77.
Fields R D. Trends in Neurosciences 1996; 19:473–80.
Frei T. Journal of Cell Biology 1992; 118:177–94.
Furka, A. International Journal of Peptide & Protein Research 1991; 37: 487–493.
Gaardsvoll H. European Journal of Cell Biology 1993; 61:100–7.
Horstkorte R. The Journal of Cell Biology 1993; 121, no 6:1409–21.
Jucker M. Brain Research 1995; Molecular Brain Rese:149–56.
Kasper C. Journal of Neuroscience Research 1996; 46:173–86.
Kiselyov V. Journal of Biological Chemistry 1997, 272: 10125–10134.
Knittel T. American Journal of Pathology 1996; 149:449–62.
Krushel L A. Proceedings of the National Academy of Sciences of the United States of America 1998; 95:2592–6.
Lackie P M. Development 1990; 110:933–47.
Lahrtz F. Journal of Neuroscience Research 1997; 50:62–8.
Lam, K S. Nature 1991, 354: 82–84.
Lam, K S. Immunomethods 1992, 1, 11–15.
Landmesser L. Neurone 1990; 4:655–67.
Luthi A. Nature 1994; 372:777–9.
Maar, T E. Journal of Neuroscience Research 1997, 47: 163–172.
Massaro A R. Italian Journal of Neurological Sciences 1987; Suppl 6:85–8.
Moller C J. Anatomy & Embryology 1991; 184:541–8.
Moller C J. Molecular Endocrinology 1992; 6:1332–42.
Nieke J. Differentiation 1985; 30:141–51.
Olsen M. Int J Devl Neuroscience 1995; 13:97–104.
Ono K. Neurone 1994; 13:595–609.
Pollerberg G E. Developmental Biology 1993; 156(2) :324–40.
Rabinowitz J E. Proceedings of the National Academy of Sciences of the United States of America 1996; 93:6421–4.
Ranheim, T. S. Proceedings of the National Academy of Sciences of the United States of America 1996, 93: 4071–4075.
Rao Y. Journal of Cell Biology 1992; 118:937–49.
Rao Y. Journal of Biological Chemistry 1994; 269:27540–8.
Romanska H M, Journal of Pediatric Gastroenterology & Nutrition 1996; 22:351–8.
Rønn L C. Brain Research 1995; 677:145–51.
Rønn L C. Ph.D.thesis; The Protein Laboratory and The Division of Neurophysiology, University of Copenhagen 1997.
Rutshauser U. Trends in Neurosciences 1996; 19:422–7.
Sandig M. Journal of Biological Chemistry 1994; 269:14841–8.
Sanes J R. Journal of Cell Biology 1986; 102:420–31.
Schmid R-S. Journal of Neurobiology 1999; 38:542–558.
Scholey A B. Neuroscience 1993; 55:499–509.
Schuch U. Neurone 1989; 3:13–20.
Shen H. Journal of Neuroscience 1997; 17:5221–9.
Stahlhut M. Journal of Neuroscience Research 1997; 48:112–21.
Stork O. European Journal of Neuroscience 1997; 9:1117–25.
Thomsen N K. Nature Structural Biology 1(996; 3:581–5.
van Kammen D P. Biological Psychiatry 1998; 43:680–6.
Walsh F S. Neuroscience Letters 1985; 59:73–8.
Zhang H. Journal of Neuroscience 1992; 12:3107–14.

What is claimed is:

1. A compound which is (1) a peptide consisting of an amino acid sequence selected from the group consisting of SEQ ID NOs: 1–4, 9, 12, 14, 15, 17, and 19–22, or (2) a compound consisting of four peptides covalently linked to a backbone consisting of three lysines, said peptides each consisting of the same amino acid sequence, said sequence being selected from the group consisting of SEQ ID NOs: 1–4, 9, 12, 14, 15, 17, and 19–22, and wherein said compound is capable of binding to neural cell adhesion molecule (NCAM) or its isolated Ig1 or Ig2 domain.

2. The compound according to claim 1 consisting of the sequence ASKKPKRNIKA (SEQ ID NO: 1).

3. The compound according to claim 1 consisting of the sequence AKKERQRKDTQ (SEQ IN NO: 2).

4. The compound according to claim 1 consisting of the sequence ARALNWGAKPK (SEQ IN NO: 3).

5. The compound according to claim 1 consisting of the sequence AGSAVKLKKKA (SEQ IN NO: 4).

6. The compound according to claim 1 consisting of the sequence ATNKKTGRRRR (SEQ IN NO: 9).

7. The compound according to claim 1 consisting of the sequence ARQKTMKPRRS (SEQ IN NO: 12).

8. The compound according to claim 1 consisting of the sequence ARKTRERKSKD (SEQ IN NO: 14).

9. The compound according to claim 1 consisting of the sequence ASQAKRRRKGPR (SEQ IN NO: 15).

10. The compound according to claim 1 consisting of the sequence AKKEKPNKPND (SEQ IN NO: 17).

11. The compound according to claim 1 consisting of the sequence AEGGKKKKMRA (SEQ IN NO: 19).

12. The compound according to claim 1 consisting of the sequence AKKKEQKQRNA (SEQ IN NO: 20).

13. The compound according to claim 1 consisting of the sequence AKSRKGNSSLM (SEQ IN NO: 21).

14. The compound according to claim 1 consisting of the sequence ARKSRDMTAIK (SEQ IN NO: 22).

15. The compound (2) of claim 1, where each peptide consists of SEQ ID NO: 1.

16. The compound (2) of claim 1, where each peptide consists of SEQ ID NO:2.

17. The compound (2) of claim 1, where each peptide consists of SEQ ID NO:3.

18. The compound of claim 1 which binds the NCAM Ig1 domain.

19. The compound of claim 18 which stimulates or promotes neurite outgrowth from NCAM presenting cell and/or proliferation thereof.

20. A pharmaceutical composition, comprising one or more of the compounds according to claim 19.

21. A method of stimulating or promoting neurite outgrowth from NCAM presenting cells and/or proliferation thereof in an individual comprising administering to said individual an effective amount of a compound as defined in claim 19.

* * * * *